US012440579B2

(12) United States Patent
Staal et al.

(10) Patent No.: US 12,440,579 B2
(45) Date of Patent: Oct. 14, 2025

(54) OPTIMISED RAG1 DEFICIENT GENE THERAPY

(71) Applicant: ACADEMISCH ZIEKENHUIS LEIDEN (H.O.D.N. LUMC), Leiden (NL)

(72) Inventors: Frank J. T. Staal, Leiden (NL); Karin Pike-Overzet, Leiden (NL); Laura Garcia-Perez, Leiden (NL); Marja C. J. A. Van Eggermond, Leiden (NL); Arjan C. Lankester, Leiden (NL)

(73) Assignee: ACADEMISCH ZIEKENHUIS LEIDEN (H.O.D.N. LUMC), Leiden (NL)

( * ) Notice: Subject to any disclaimer, the term of this patent is extended or adjusted under 35 U.S.C. 154(b) by 1016 days.

(21) Appl. No.: 17/438,135

(22) PCT Filed: Mar. 6, 2020

(86) PCT No.: PCT/NL2020/050152
§ 371 (c)(1),
(2) Date: Sep. 10, 2021

(87) PCT Pub. No.: WO2020/185073
PCT Pub. Date: Sep. 17, 2020

(65) Prior Publication Data

US 2022/0160894 A1 May 26, 2022

(30) Foreign Application Priority Data

Mar. 11, 2019 (NL) ..................................... 2022714

(51) Int. Cl.
*A61K 48/00* (2006.01)
*C12N 15/86* (2006.01)

(52) U.S. Cl.
CPC ............ *A61K 48/005* (2013.01); *C12N 15/86* (2013.01); *C12N 2740/16043* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 2011/0179506 | A1 | 7/2011 | Grizot |
| 2019/0038771 | A1 | 2/2019 | Cradick et al. |

FOREIGN PATENT DOCUMENTS

| | | | |
|---|---|---|---|
| CN | 101517071 | A | 8/2009 |
| CN | 105980568 | A | 9/2016 |
| CN | 105980569 | A | 9/2016 |
| CN | 110564773 | A | 12/2019 |
| CN | 112522309 | A | 3/2021 |
| CN | 114929289 | A | 8/2022 |
| CN | 115515606 | A | 12/2022 |
| CN | 116635523 | A | 8/2023 |
| JP | 2015-529466 | A | 10/2015 |

OTHER PUBLICATIONS

Bahner et al., Molecular Therapy, 2007, 15: 76-85.*
Aiuti et al., Science, 2002, 296: 2410-2413.*
Sequence alignment, 2024.*
International Search Report and Written Opinion for corresponding Application No. PCT/NL2020/050152 (mailed May 14, 2021).
Pike-Overzet et al., "Abstracts of the ASGCT 18th Annual Meeting," Mol. Therapy 23(1):s1-s289 (2015).
Pike-Overzet et al., "ASGCT 16th Annual Meeting Abstracts," Mol. Therapy Insert vol. s1-s258 (2013).
Pike-Overzet et al., "Correction of Murine RagI Deficiency by Self-Inactivating Lentiviral Vector-Mediated Gene Transfer," Leukemia 25(9):1471-1483 (2011).
Pike-Overzet et al., "Self-Inactivating Lentiviral Vectors for Corrections of RAG1 Severe Combined Immunodeficiency," Exp. Hematol. 40(8):s46 (2012).
Almarza et al., "Characteristics of Lentiviral Vectors Harboring the Proximal Promoter of Thevav Proto-Oncogene: A Weak and Efficient Promoter for Gene Therapy," Mol. Therapy 15(8):1487-1494 (2007).
Carbonaro et al., "Preclinical Demonstration of Lentiviral Vector-Mediated Corrections of Immunological and Metabolic Abnormalities in Models of Adenosine Deaminase Deficiency," Mol. Therapy 22(3):607-622 (2014).
Carbonaro et al., "In Vivo Transduction by Intravenous Injection of a Lentiviral Vector Expressing Human ADA into Neonatal ADA Gene Knockout Mice: A Novel From of Enzyme Replacement Therapy for ADA Deficiency," Mol. Therapy 13(6):1110-1120 (2006).
International Search Report and Written Opinion for corresponding Application No. NL2022714 (mailed Aug. 14, 2019).
Castiello, M. C. et al. Partial correction of immunodeficiency by lentiviral vector gene therapy in mouse models carrying Ragl hypomorphic mutations. Frontiers in Immunology, 14:1268620, 19 pages (2023).
GenBank, Accession No. AAH37344.1, RAG1 protein [*Homo sapiens*]. Strausberg, R.L. et al, Jul. 28, 2005.

(Continued)

*Primary Examiner* — Ileana Popa
(74) *Attorney, Agent, or Firm* — Baker, Donelson, Bearman, Caldwell, & Berkowitz, PC

(57) ABSTRACT

The present invention provides novel expression cassettes, retroviral plasmids, vectors, virions, compositions and recombinant cells comprising a promoter operably linked to a codon optimised recombination activating (RAG1) transgene. These novel expression cassettes, retroviral plasmids, vectors, virions, compositions and recombinant cells are useful in the treatment of diseases caused by complete or partial loss-of-function of the protein encoded by the rag-1 gene, such as RAG-deficient severe combined immunodeficiency (RAG1-SCID), Omenn Syndrome (OS), atypical-SCID or combined immunodeficiency (CID). Corresponding methods of treatment are also provided.

20 Claims, 59 Drawing Sheets

Specification includes a Sequence Listing.

(56) References Cited

OTHER PUBLICATIONS

Hou Zhenjiang et al. Hematology testing technology. Jan. 31, 2023, 16 pages with translation (2013).
Pike-Overzet, et al. Successful Correction of Rag1 Severe Combined Immunedefciency at Clinically Relevant Vector Copy Numbers. Karin Molecular Therapy, vol. 23, supplement 1, S111, 1 page (2015).
JP Office Action in Japanese Application No. 2021-554622, dated Feb. 27, 2024, 4 pages (with English translation).
Miyoshi, “Gene transfer into hematopoietic stem cells using lentiviral vectors”, Virus, 2002, 52(2): 225-231 (with English abstract).
Lagresle-Peyrou, C., Benjelloun, F., Hue, C., Andre-Schmutz, I., Bonhomme, D., Forveille, M., Beldjord, K., Hacein-Bey-Abina, S., De Villartay, J.P., Charneau, P., et al. (2008). Restoration of human B-cell differentiation into NOD-SCID mice engrafted with gene-corrected CD34+ cells isolated from Artemis or RAG1-deficient patients. Molecular therapy : the journal of the American Society of Gene Therapy 16, 396-403.
Lagresle-Peyrou, C., Yates, F., Malassis-Seris, M., Hue, C., Morillon, E., Garrigue, A., Liu, A., Hajdari, P., Stockholm, D., Danos, O., et al. (2006). Long-term immune reconstitution in RAG-1-deficient mice treated by retroviral gene therapy: a balance between efficiency and toxicity. Blood 107, 63-72.
Pike-Overzet, K., Baum, C., Bredius, R.G., Cavazzana, M., Driessen, G.J., Fibbe, W.E., Gaspar, H.B., Hoeben, R.C., Lagresle-Peyrou, C., Lankester, A., et al. (2014). Successful RAG1-SCID gene therapy depends on the level of RAG1 expression. The Journal of allergy and clinical immunology 134, 242-243.
Van Til, N.P., Sarwari, R., Visser, T.P., Hauer, J., Lagresle-Peyrou, C., van der Velden, G., Malshetty, V., Cortes, P., Jollet, A., Danos, O., et al. (2014). Recombination-activating gene 1 (Rag1)-deficient mice with severe combined immunodeficiency treated with lentiviral gene therapy demonstrate autoimmune Omenn-like syndrome. Journal of Allergy and Clinical Immunology 133, 1116-1123.

* cited by examiner

C)

C)

A)

B)

E)

5' CCATTGCATACGTTGTATCCATATCATAATATGTACATTTATATTGGCTCATGTCCAACATTACCGCCATGTTGACATTGATTAT 85
3' GGTAACGTATGCAACATAGGTATAGTATTATACATGTAAATATAACCGAGTACAGGTTGTAATGGCGGTACAACTGTAACTAATA
CMV

SpeI
TGACTAGTTATTAATAGTAATCAATTACGGGGTCATTAGTTCATAGCCCATATATGGAGTTCCGCGTTACATAACTTACGGTAAA 170
ACTGATCAATAATTATCATTAGTTAATGCCCCAGTAATCAAGTATCGGGTATATACCTCAAGGCGCAATGTATTGAATGCCATTT
CMV

TGGCCCGCCTGGCTGACCGCCCAACGACCCCCGCCCATTGACGTCAATAATGACGTATGTTCCCATAGTAACGCCAATAGGGACT 255
ACCGGGCGGACCGACTGGCGGGTTGCTGGGGGCGGGTAACTGCAGTTATTACTGCATACAAGGGTATCATTGCGGTTATCCCTGA
CMV

NdeI
TTCCATTGACGTCAATGGGTGGAGTATTTACGGTAAACTGCCCACTTGGCAGTACATCAAGTGTATCATATGCCAAGTACGCCCC 340
AAGGTAACTGCAGTTACCCACCTCATAAATGCCATTTGACGGGTGAACCGTCATGTAGTTCACATAGTATACGGTTCATGCGGGG
CMV

CTATTGACGTCAATGACGGTAAATGGCCCGCCTGGCATTATGCCCAGTACATGACCTTATGGGACTTTCCTACTTGGCAGTACAT 425
GATAACTGCAGTTACTGCCATTTACCGGGCGGACCGTAATACGGGTCATGTACTGGAATACCCTGAAAGGATGAACCGTCATGTA
CMV

FIG. 9 (cont.)

GGCTTTCCCCGTCAAGCTCTAAATCGGGGGCTCCCTTTAGGGTTCCGATTTAGTGCTTTACGGCACCTCGACCCCAAAAAACTTG 7650
CCGAAAGGGGCAGTTCGAGATTTAGCCCCCGAGGGAAATCCCAAGGCTAAATCACGAAATGCCGTGGAGCTGGGGTTTTTTGAAC
f1 origin ATTAGGGTGATGGTTCACGTAGTGGGCCATCGCCCTGATAGACGGTTTTTCGCCCTTTGACGTTGGAGTCCACGTTCTTTAATAG 7735
TAATCCCACTACCAAGTGCATCACCCGGTAGCGGGACTATCTGCCAAAAAGCGGGAAACTGCAACCTCAGGTGCAAGAAATTATC
f1 origin TGGACTCTTGTTCCAAACTGGAACAACACTCAACCCTATCTCGGTCTATTCTTTTGATTTATAAGGGATTTTGCCGATTTCGGCC 7820
ACCTGAGAACAAGGTTTGACCTTGTTGTGAGTTGGGATAGAGCCAGATAAGAAAACTAAATATTCCCTAAAACGGCTAAAGCCGG
f1 origin TATTGGTTAAAAAATGAGCTGATTTAACAAAAATTTAACGCGAATTTTAACAAAATATTAACGCTTACAATTTAGGTGGCACTTT 7905
ATAACCAATTTTTTACTCGACTAAATTGTTTTTAAATTGCGCTTAAAATTGTTTTATAATTGCGAATGTTAAATCCACCGTGAAA
f1 origin TCGGGGAAATGTGCGCGGAACCCCTATTTGTTTATTTTTCTAAATACATTCAAATATGTATCCGCTCATGAGACAATAACCCTGA 7990
AGCCCCTTTACACGCGCCTTGGGGATAAACAAATAAAAAGATTTATGTAAGTTTATACATAGGCGAGTACTCTGTTATTGGGACT TAAATGCTTCAATAATATTGAAAAAGGAAGAGTATGAGTATTCAACATTTCCGTGTCGCCCTTATTCCCTTTTTTGCGGCATTTT 8075
ATTTACGAAGTTATTATAACTTTTTCCTTCTCATACTCATAAGTTGTAAAGGCACAGCGGGAATAAGGGAAAAAACGCCGTAAAA
1 5 10 15
Met Ser Ile Gln His Phe Arg Val Ala Leu Ile Pro Phe Phe Ala Ala Phe
Beta Lactamase

FIG. 9 (cont.)

```
AGCGCAGATACCAAATACTGTTCTTCTAGTGTAGCCGTAGTTAGGCCACCACTTCAAGAACTCTGTAGCACCGCCTACATACCTC
                                                                                        9265
TCGCGTCTATGGTTTATGACAAGAAGATCACATCGGCATCAATCCGGTGGTGAAGTTCTTGAGACATCGTGGCGGATGTATGGAG
ColE1 origin

GCTCTGCTAATCCTGTTACCAGTGGCTGCTGCCAGTGGCGATAAGTCGTGTCTTACCGGGTTGGACTCAAGACGATAGTTACCGG
                                                                                        9350
CGAGACGATTAGGACAATGGTCACCGACGACGGTCACCGCTATTCAGCACAGAATGGCCCAACCTGAGTTCTGCTATCAATGGCC
ColE1 origin

ATAAGGCGCAGCGGTCGGGCTGAACGGGGGGTTCGTGCACACAGCCCAGCTTGGAGCGAACGACCTACACCGAACTGAGATACCT
                                                                                        9435
TATTCCGCGTCGCCAGCCCGACTTGCCCCCCAAGCACGTGTGTCGGGTCGAACCTCGCTTGCTGGATGTGGCTTGACTCTATGGA
ColE1 origin

ACAGCGTGAGCTATGAGAAAGCGCCACGCTTCCCGAAGGGAGAAAGGCGGACAGGTATCCGGTAAGCGGCAGGGTCGGAACAGGA
                                                                                        9520
TGTCGCACTCGATACTCTTTCGCGGTGCGAAGGGCTTCCCTCTTTCCGCCTGTCCATAGGCCATTCGCCGTCCCAGCCTTGTCCT
ColE1 origin

GAGCGCACGAGGGAGCTTCCAGGGGGAAACGCCTGGTATCTTTATAGTCCTGTCGGGTTTCGCCACCTCTGACTTGAGCGTCGAT
                                                                                        9605
CTCGCGTGCTCCCTCGAAGGTCCCCCTTTGCGGACCATAGAAATATCAGGACAGCCCAAAGCGGTGGAGACTGAACTCGCAGCTA
ColE1 origin

TTTTGTGATGCTCGTCAGGGGGGCGGAGCCTATGGAAAAACGCCAGCAACGCGGCCTTTTTACGGTTCCTGGCCTTTTGCTGGCC
                                                                                        9690
AAAACACTACGAGCAGTCCCCCCGCCTCGGATACCTTTTTGCGGTCGTTGCGCCGGAAAAATGCCAAGGACCGGAAAACGACCGG
ColE1 origin
```

FIG. 9 (cont.)

PciI

TTTTGCTCACATGTTCTTTCCTGCGTTATCCCCTGATTCTGTGGATAACCGTATTACCGCCTTTGAGTGAGCTGATACCGCTCGC 9775
AAAACGAGTGTACAAGAAAGGACGCAATAGGGGACTAAGACACCTATTGGCATAATGGCGGAAACTCACTCGACTATGGCGAGCG

CGCAGCCGAACGACCGAGCGCAGCGAGTCAGTGAGCGAGGAAGCGGAAGAGCGCCCAATACGCAAACCGCCTCTCCCCGCGCGTT 9860
GCGTCGGCTTGCTGGCTCGCGTCGCTCAGTCACTCGCTCCTTCGCCTTCTCGCGGGTTATGCGTTTGGCGGAGAGGGGCGCGCAA

GGCCGATTCATTAATGCAGCTGGCACGACAGGTTTCCCGACTGGAAAGCGGGCAGTGAGCGCAACGCAATTAATGTGAGTTAGCT 9945
CCGGCTAAGTAATTACGTCGACCGTGCTGTCCAAAGGGCTGACCTTTCGCCCGTCACTCGCGTTGCGTTAATTACACTCAATCGA

CACTCATTAGGCACCCCAGGCTTTACACTTTATGCTTCCGGCTCGTATGTTGTGTGGAATTGTGAGCGGATAACAATTTCACACA 10,030
GTGAGTAATCCGTGGGGTCCGAAATGTGAAATACGAAGGCCGAGCATACAACACACCTTAACACTCGCCTATTGTTAAAGTGTGT

GGAAACAGCTATGACCATGATTACGCCAAGCGCGCAATTAACCCTCACTAAAGGGAACAAAAGCTGGAGCTGCAAGCTTGG 3' ... 10,111
CCTTTGTCGATACTGGTACTAATGCGGTTCGCGCGTTAATTGGGAGTGATTTCCCTTGTTTTCGACCTCGACGTTCGAACC 5'

FIG. 9 (cont.)

| | Feature | | Location | Size | | | Type |
|---|---|---|---|---|---|---|---|
| ✓ | **CMV** | | 1 .. 671 | 671 bp | ▩ | ⟷ | misc_feature |
| | /gene | = CMV | | | | | |
| ✓ | **HIV R** | | 673 .. 768 | 96 bp | ▩ | ⟷ | misc_feature |
| | /gene | = HIV R | | | | | |
| ✓ | **HIV1-polyA** | | 673 .. 768 | 96 bp | ▩ | ⟷ | misc_feature |
| | /gene | = HIV1-polyA | | | | | |
| ✓ | **HIV U5** | | 769 .. 853 | 85 bp | ▩ | ⟷ | misc_feature |
| | /gene | = HIV U5 | | | | | |
| ✓ | **HIV1 psi** | | 904 .. 1041 | 138 bp | ▩ | ⟷ | misc_feature |
| | /gene | = HIV1 psi | | | | | |
| ✓ | **dGag** | | 1043 .. 1371 | 329 bp | ▩ | ⟷ | misc_feature |
| ✓ | **HIV-1 Rev response element** | | 1517 .. 1750 | 234 bp | ▩ | ⟷ | misc_feature |
| ✓ | **PPT** | | 2246 .. 2264 | 19 bp | ▩ | ⟷ | misc_feature |
| | /gene | = PPT | | | | | |
| ✓ | **MND** | | 2412 .. 2794 | 383 bp | ▩ | ⟷ | promoter |
| | /gene | = MND | | | | | |

FIG. 9 (cont.)

| Feature | | | Location | Size | | | Type |
|---|---|---|---|---|---|---|---|
| ✓ **coRAG1** | | | 2814 .. 5945 | 3132 bp | ▩ | → | CDS |
| /gene | = | Rag1co | | | | | |
| /translation | = | MAASFPPTLGLSSAPDEIQHPHIKFSEWKFKLFRVRSFEKTPEEAQKEKKDSFEGKPSLEQSPAVLDKADGQKPVPTQ PLLKAHPKFSKKFHDNEKARGKAIHQANLRHLCRICGNSFRADEHNRRYPVHGPVDGKTLGLLRKKEKRATSWPDLIA KVFRIDVKADVDSIHPTEFCHNCWSIMHRKFSSAPCEVYFPRNVTMEWHPHTPSCDICNTARRGLKRKSLQPNLQLS KKLKTVLDQARQARQRKRRAQARISSKDVMKKIANCSKIHLSTKLLAVDFPEHFVKSISCQICEHILADPVETNCKHVF CRVCILRCLKVMGSYCPSCRYPCFPTDLESPVKSFLSVLNSLMVKCPAKECNEEVSLEKYNHHISSHKESKEIFVHINK GGRPRQHLLSLTRRAQKHRLRELKLQVKAFADKEEGGDVKSVCMTLFLLALRARNEHRQADELEAIMQGKGSGLQPA VCLAIRVNTFLSCSQYHKMYRTVKAITGRQIFQPLHALRNAEKVLLPGYHHFEWQPPLKNVSSSTDVGIIDGLSGLSSS VDDYPVDTIAKRFRYDSALVSALMDMEEDILEGMRSQDLDDYLNGPFTVVVKESCDGMGDVSEKHGSGPVVPEKAVR FSFTIMKITIAHSSQNVKVFEEAKPNSELCCKPLCLMLADESDHETLTAILSPLIAEREAMKSSELMLELGGILRTFKFIF RGTGYDEKLVREVEGLEASGSVYICTLCDATRLEASQNLVFHSITRSHAENLERYEVWRSNPYHESVEELRDRVKGVSA KPFIETVPSIDALHCDIGNAAEFYKIFQLEIGEVYKNPNASKEERKRWQATLDKHLRKKMNLKPIMRMNGNFARKLMTK ETVDAVCELIPSEERHEALRELMDLYLKMKPVWRSSCPAKECPESLCQYSFNSQRFAELLSTKFKYRYEGKITNYFHKT LAHVPEIIERDGSIGAWASEGNESGNKLFRRFRKMNARQSKCYEMEDVLKHHWLYTSKYLQKFMNAHNALKTSGFTM NPQASLGDPLGIEDSLESQDSMEF* | | | | | |
| | | 1043 amino acids = 119,1 kDa | | | | | |
| ✓ **WPREmut6** | | | 5955 .. 6547 | 593 bp | ▩ | ⟼ | misc_feature |
| /gene | = | WPREmut6 | | | | | |
| ✓ **PPT** | | | 6609 .. 6627 | 19 bp | ▩ | ⟼ | misc_feature |
| /gene | = | PPT | | | | | |
| ✓ **Delta U3** | | | 6630 .. 6683 | 54 bp | ▩ | ⟼ | misc_feature |
| /gene | = | Delta U3 | | | | | |
| ✓ **HIV R** | | | 6684 .. 6779 | 96 bp | ▩ | ⟼ | misc_feature |
| /gene | = | HIV R | | | | | |
| ✓ **HIV1-polyA** | | | 6684 .. 6779 | 96 bp | ▩ | ⟼ | misc_feature |
| /gene | = | HIV1-polyA | | | | | |

FIG. 9 (cont.)

| | Feature | | Location | Size | | ⇄ | Type |
|---|---|---|---|---|---|---|---|
| ✓ | **HIV U5** | | 6780 .. 6864 | 85 bp | | ⟼ | misc_feature |
| | /gene | = HIV U5 | | | | | |
| ✓ | **f1 origin** | | 7438 .. 7893 | 456 bp | | ⟼ | misc_feature |
| | /gene | = f1 origin | | | | | |
| ✓ | **Beta\Lactamase** | | 8024 .. 8884 | 861 bp | | → | CDS |
| | /gene | = Beta\Lactamase | | | | | |
| | /translation | = MSIQHFRVALIPFFAAFCLPVFAHPETLVKVKDAEDQLGARVGYIELDLNSGKILESFRPEERFPMMSTFKVLLCGAVLS RIDAGQEQLGRRIHYSQNDLVEYSPVTEKHLTDGMTVRELCSAAITMSDNTAANLLLTTIGGPKELTAFLHNMGDHVTR LDRWEPELNEAIPNDERDTTMPVAMATTLRKLLTGELLTLASRQQLIDWMEADKVAGPLLRSALPAGWFIADKSGAGE RGSRGIIAALGPDGKPSRIVVIYTTGSQATMDERNRQIAEIGASLIKHW* | | | | | |
| | | 286 amino acids = 31,6 kDa | | | | | |
| ✓ | **ColE1 origin** | | 9044 .. 9658 | 615 bp | | ⟼ | misc_feature |
| | /gene | = ColE1 origin | | | | | |

FIG. 9 (cont.)

OPTIMISED RAG1 DEFICIENT GENE THERAPY

This application is a national stage application under 35 U.S.C. § 371 of PCT Application No. PCT/NL2020/050152, filed Mar. 6, 2020, which claims the priority benefit of Netherlands Patent Application No. 2022714, filed Mar. 11, 2019, which are hereby incorporated by reference in their entirety.

The present invention provides novel expression cassettes, retroviral plasmids, vectors, virions, compositions and recombinant cells comprising a promoter operably linked to a codon optimised recombination activating (RAG1) transgene. These novel expression cassettes, retroviral plasmids, vectors, virions, compositions and recombinant cells are useful in the treatment of diseases caused by complete or partial loss-of-function of the protein encoded by the rag-1 gene, such as RAG-deficient severe combined immunodeficiency (RAG1-SCID), Omenn Syndrome (OS), atypical-SCID or combined immunodeficiency (CID). Corresponding methods of treatment are also provided.

BACKGROUND

Gene therapy for rare inherited immune disorders has become a clinical reality in recent years, especially for severe combined immunodeficiency (SCID). For example, two major types of SCID (ADA-SCID, X-SCID) have been successfully treated by autologous stem cell-based gene therapy. However, for the most common group of SCID, SCID with underlying recombination defects (e.g. RAG-deficient SCID; also known as RAG-SCID), this has not yet occurred due to the higher complexity of the genes involved.

Patients with RAG-deficient SCID have a mutation in either RAG1 or RAG2, which are required for the genetic assembly of T cell receptors (TCRs) and B cell receptors (BCRs). Affected children typically experience a wide range of serious and life-threatening infections, including pneumonia, meningitis and sepsis. Replacing the affected bone marrow with healthy, unmodified allogeneic stem cells via allogeneic stem cell transplantation (allo-SCT) is currently the only therapy for RAG-SCID. Although overall survival is satisfactory in matched SCT recipients, the outcome in mismatched SCT recipients, which represent the majority of cases, is significantly worse.

Moreover, approximately 25% of transplant patients develop graft vs. host disease, which significantly reduces outcome in terms of morbidity, immune reconstitution, and transplant related mortality (Gennery, 2010). Thus, transplant outcome in RAG-SCID (and other recombination-defective forms of T-SCID and B-SCID) is significantly worse than for SCID with B cells (i.e. T-B+ SCID). Taken together, these data suggest that the only curative option currently available—allo-SCT—has major limitations with respect to both curative potential and survival chance, thus demonstrating an urgent need for new and improved strategies based on the genetic correction of autologous stem cells.

Although successful clinical trials using autologous stem cell-based gene therapy have been carried out for treatment of X-linked SCID and ADA-SCID, these trials revealed a severe adverse effect: the development of lymphoproliferative disorders/leukaemia. In all cases, T cell acute lymphoblastic leukaemia (T-ALL) occurred as a direct consequence of insertional mutagenesis by the retroviral vector that was used to deliver the therapeutic gene. After this serious setback with gene therapy, recent work has shown that next generation vectors, particularly vectors in which the viral promoter/enhancer sequences are rendered inactive (self-inactivating vectors, or SIN vectors), significantly reduce the incidence of insertional mutagenesis.

The most recent clinical trials in X-linked SCID and ADA-SCID show that SIN lentiviral vectors are both safe and highly effective, thereby promoting further clinical development of genetically modified hematopoietic stem cells. However, unlike X-linked SCID and ADA-SCID, using gene therapy for treating RAG-SCID has been notoriously difficult. Previous attempts (Lagresle-Peyrou, 2006) used gamma retroviral vectors in a preclinical Rag1−/− model, which carried a high risk of insertional mutagenesis. Although RAG1 gamma retroviral vectors were able to correct the deficiency more readily, SIN lentiviral vectors initially resulted in insufficient expression of the therapeutic RAG1 gene, leading to 'leaky' SCID or an Omenn-like phenotype. Inconsistent results have been observed in the field (van Til., 2014), due to differences in expression levels and transduction efficiencies obtained for the therapeutic gene.

New and improved strategies for treating RAG1-deficient SCID and OS are needed.

BRIEF SUMMARY OF THE DISCLOSURE

The inventors have surprisingly found a minimum threshold level of RAG1 expression that provides a therapeutic effect in a preclinical model of RAG-deficient SCID using clinically acceptable lentiviral gene therapy and a codon optimised RAG1 transgene sequence.

The inventors designed clinically relevant lentiviral SIN plasmids with different internal promoters driving expression of a codon optimised RAG1 gene. Using Rag1−/− mice as a preclinical model for RAG1-SCID to assess the efficacy of the various plasmids at low plasmid copy number, the inventors observed that B and T cell reconstitution directly correlated with RAG1 expression. Mice with low RAG1 expression showed poor immune reconstitution, however high RAG1 expression resulted in phenotypic and functional lymphocyte reconstitution comparable to mice receiving wild type stem cells. Surprisingly, RAG1-SCID patient $CD34^+$ cells transduced with a clinical RAG1 plasmid and transplanted into NOD SCID gamma (NSG) mice led to fully restored human B and T cell development. Together with favourable safety data, the inventors' results provide a robust basis towards a human clinical trial for RAG1-deficient SCID.

The inventors have therefore provided a new system for inducing and maintaining a therapeutic threshold level of RAG1 expression in a RAG-deficient cell using a novel codon optimised RAG1 transgene sequence. The inventors have shown that a therapeutic effect (in terms of B and T cell reconstitution in vivo) is observed when RAG1 expression levels are at least three-fold higher for B cell restoration (and 10-fold higher for T cell restoration) than certain housekeeping genes, such as ABL1. Accordingly, a minimum threshold of three-fold higher expression is shown herein to have a beneficial therapeutic effect. The inventors have shown for the first time that such levels of RAG1 expression can be achieved using low copy number retroviral plasmids that encode a codon optimised RAG1 transgene (i.e. a RAG1 expression level that is at least three-fold higher than ABL1 in the cell can be achieved even when there are 5 or fewer copies of the RAG1 transgene (in the context of an expression cassette) integrated into the genome of the cell when a codon optimised RAG1 transgene sequence is used).

In this context, as will be well known in the art, "low copy number" refers to plasmids that integrate into the genome of the target cell at a frequency of 5 or fewer copies per cell (i.e. 5 or fewer, 4 or fewer, 3 or fewer, 2 or fewer, 1 or fewer, 0.5 or fewer, 0.4 or fewer, 0.3 or fewer, 0.2 or fewer etc copies per cell). The use of low copy number plasmids is advantageous, as it significantly reduces the incidence of insertional mutagenesis during gene therapy. Advantageously, the inventors have shown that a beneficial effect may be achieved with a copy number as low as 0.2 per cell.

The invention has been exemplified using a low copy number plasmid, specifically a self-inactivating (SIN) lentiviral (LV) plasmid comprising a pCCL backbone. This plasmid is particularly advantageous because it can be produced at higher titres compared to other LV backbones. However, other low copy number plasmids may also be useful in the context of the invention (as they would equally provide the advantage of significantly reducing the incidence of insertional mutagenesis). Alternative low copy number plasmids are described in detail elsewhere herein.

The inventors have demonstrated the requisite threshold level of RAG1 expression using an MND promoter. Surprisingly, when the MND promoter is operably linked to a codon optimised RAG1 transgene, the level of RAG1 expression achieved from a low copy number plasmid in vivo is sufficient to induce B and T cell reconstitution. The inventors have therefore identified that a combination of a low copy number plasmid, a codon optimised RAG1 transgene sequence and a strong promoter such as MND is sufficient to drive RAG1 expression to therapeutic levels in vivo. Although the invention has been exemplified using an MND promoter, other strong promoters that induce an equivalent (or higher) level of RAG1 expression may also be used. For example, in other systems, CMV, RSV and CAG promoters are known to drive high levels of expression of linked transgenes. Now that the threshold level of RAG1 expression required for therapeutic effect is known (as provided herein for the first time), other promoters known to be equivalent to MND (such as CMV, RSV and CAG promoters, and others) may equally be applied in the context of the invention to achieve the desired effect. The invention therefore encompasses the use of such promoters as alternatives to MND.

The data provided herein utilises a codon optimised sequence of RAG1 as the RAG1 transgene that is operably linked to the requisite promoter (e.g. MND; although others such as a CMV, RSV or CAG promoter may also be used). As described in detail elsewhere in the application, use of a codon optimised RAG1 sequence is advantageous, as it yields higher viral titres, and can increase RAG1 protein stability. Use of a codon optimised transgene sequence therefore helps to achieve the minimum threshold of RAG expression needed to obtain a therapeutic effect (i.e. at a level that is at least three-fold higher than certain housekeeping genes, such as ABL1, in the cell even when there are 5 or fewer copies of the RAG1 transgene integrated into the genome of the cell).

In one aspect, an expression cassette comprising a promoter operably linked to a RAG1 transgene that comprises the nucleic acid sequence of SEQ ID NO: 2 is provided, which, when expressed in a human CD34+ haematopoietic stem cell having 5 or fewer copies of the expression cassette integrated into its genome, generates an expression product that is at a level least three-fold higher than the expression level of ABL1 in the cell.

Suitably, the promoter may be selected from MND, CMV, RSV and CAG.

Accordingly, an expression cassette comprising a promoter operably linked to a RAG1 transgene that comprises the nucleic acid sequence of SEQ ID NO: 2, wherein the promoter is selected from MND, CMV, RSV, and CAG is therefore provided. In one example, the RAG1 transgene comprises the nucleic acid sequence of SEQ ID NO:4. Suitably, when the expression cassette is expressed in a human CD34+ haematopoietic stem cell having 5 or fewer copies of the expression cassette integrated into its genome, generates an expression product that is at a level least three-fold higher than the expression level of ABL1 in the cell.

Suitably, the RAG1 transgene encodes a polypeptide comprising the sequence of SEQ ID NO: 1.

Suitably, the RAG1 transgene may comprise the nucleic acid sequence of SEQ ID NO:4.

Suitably, the promoter may be MND.

Suitably, the expression cassette may further comprise a nucleotide sequence encoding Woodchuck hepatitis virus (WHP) posttranscriptional regulatory element (WPRE).

In one aspect, a retroviral plasmid comprising an expression cassette of the invention is provided.

Suitably, the plasmid may be a self-inactivating (SIN) lentiviral plasmid.

Suitably, the plasmid may comprise a pCCL backbone.

Suitably, the plasmid may comprise a pCCL backbone, a nucleotide sequence encoding WPRE, a MND promoter and a transgene comprising a nucleic acid sequence of SEQ ID NO: 4.

Suitably, the plasmid may comprise the sequence of FIG. 9.

In one aspect, a virion comprising an expression cassette of the invention is provided.

In one aspect, a composition is provided comprising an expression cassette of the invention or a plasmid of the invention, or a virion of the invention, and a pharmaceutically acceptable adjuvant, carrier, excipient or diluent.

In one aspect, a recombinant CD34+ haematopoietic stem cell is provided comprising an expression cassette of the invention.

In one aspect, an ex vivo method of generating a recombinant CD34+ haematopoietic stem cell is provided, the method comprising contacting the cell with a plasmid of the invention or a virion of the invention under conditions in which the expression cassette is incorporated and expressed by the cell to generate the recombinant CD34+ haematopoietic stem cell.

In one aspect an expression cassette, plasmid, composition, virion or recombinant cell of the invention is provided for use in therapy.

Suitably, the expression cassette, vector, composition, virion or recombinant cell may be for use in the treatment of RAG1 deficient SCID, Omenn syndrome (OS), atypical SCID or combined immunodeficiency (CID). For example, the expression cassette, vector, composition, virion or recombinant cell may be for use in the treatment of RAG1 deficient SCID or Omenn syndrome (OS).

In one aspect, a method of treating a subject is provided comprising administering a therapeutically effective amount of an expression cassette, plasmid, composition, virion particle or recombinant cell of the invention to a subject in need thereof.

Suitably, the subject may have RAG1 deficient SCID, Omenn syndrome (OS), atypical SCID or combined immunodeficiency (CID). For example, the subject may have RAG1 deficient SCID or Omenn syndrome (OS).

In one aspect, a method of treating RAG1 deficient SCID, Omenn syndrome (OS), atypical SCID or combined immunodeficiency (CID) in a subject in need thereof is provided comprising the steps of:

(i) extracting CD34+ haematopoietic stem cell from said subject;
(ii) contacting said cells from (i) with a virion of the invention or a plasmid of the invention;
(iii) incubating said cells from (ii) for a period of time; and
(iv) introducing the cells from (iii) in to said subject.

Suitably, the method may further comprise the step of administering chemotherapy or other conditioning regimens to the subject prior to step (iv).

Right panel: Histological analysis of thymus reconstitution by hematoxilyn and eosin staining (Scale bar=50 μm), and cytokeratin staining (scale bar represents 50 micro m). Representative image from WT Control and MND-c.o.RAG1 mice.

Figure 4:
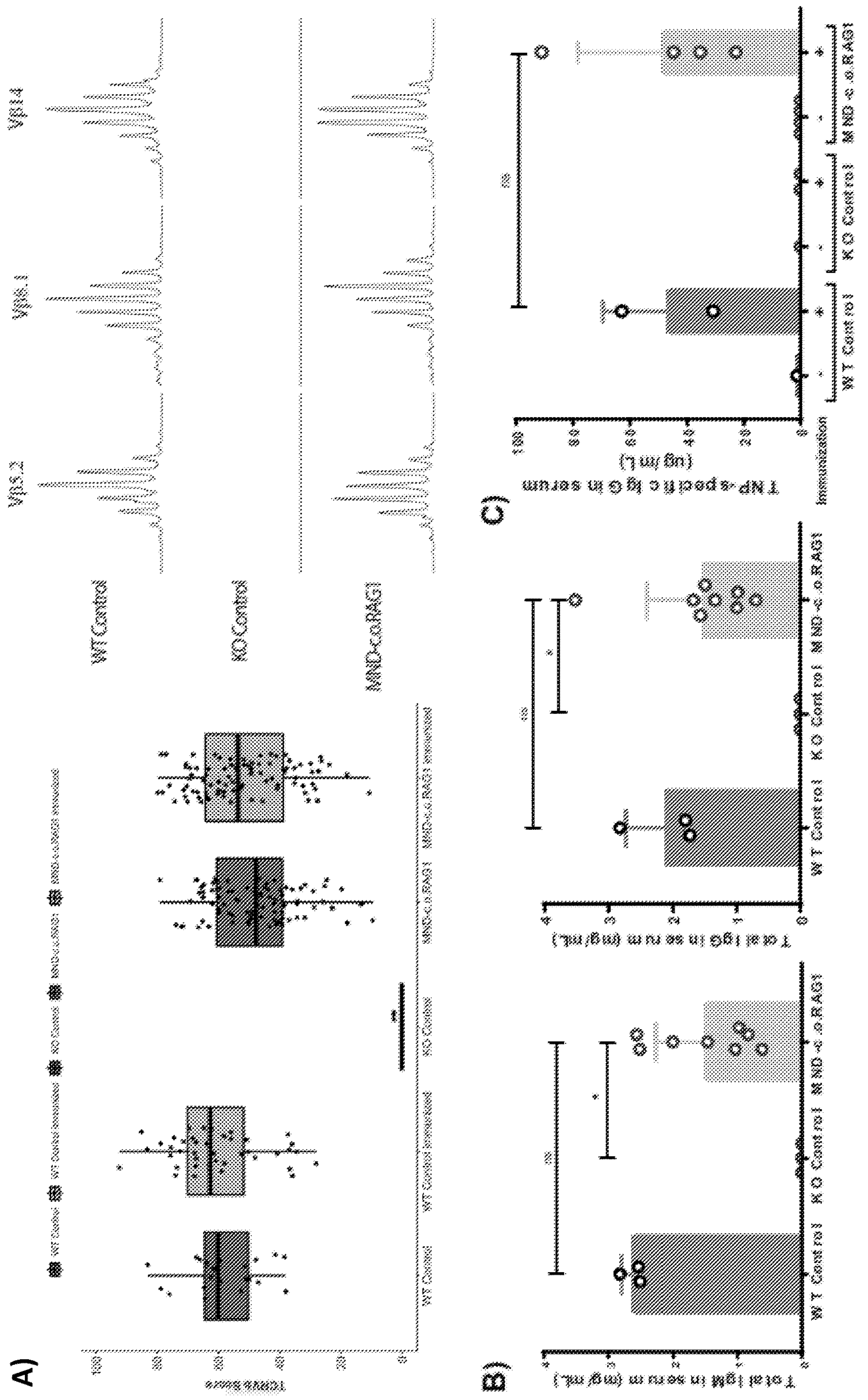

FIG. 4: Functional Ig and TCR rearrangements and Ig class-switching after Rag1 gene therapy. A) TCR Vβ repertoire analysis by GeneScan. A total of 24 Vβ families was analysed on spleen cells from 3 WT control, 1 KO control and 8 MND-c.o.RAG1 mice (non-immunized and immunized). Overall score of all the families was calculated. Representative samples of GeneScan plots are shown for 3 different families (x-axis indicates CDR3 length; y-axis shows the fluorescence intensity of the runoff products). B) Quantification of total IgG and IgM in serum by ELISA. C) Quantification of TNP-specific IgG in serum of immunized mice. Each dot represent a value obtained in one mouse. One-way ANOVA test *p<0.05.

Figure 5:
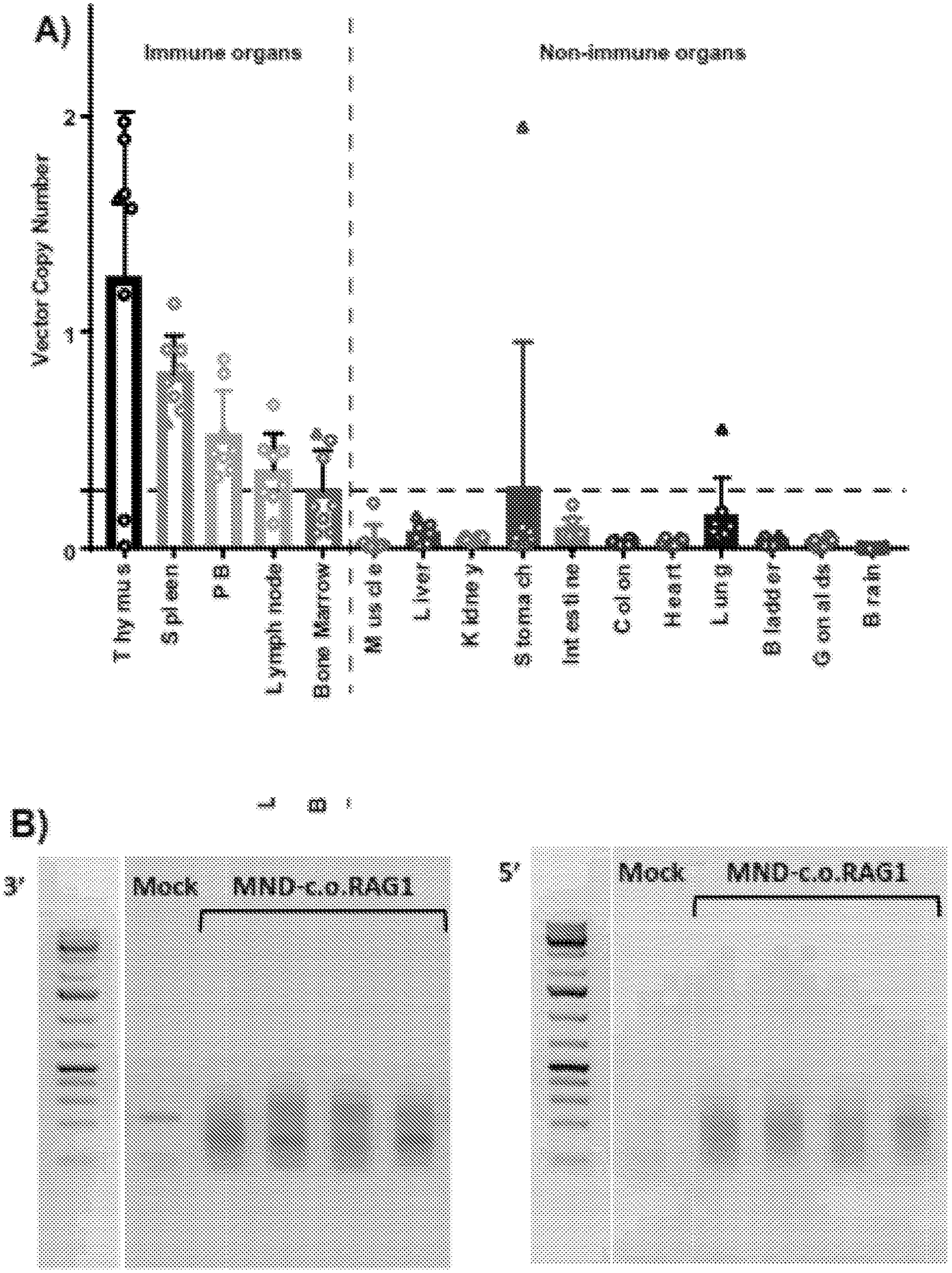
Figure 5:
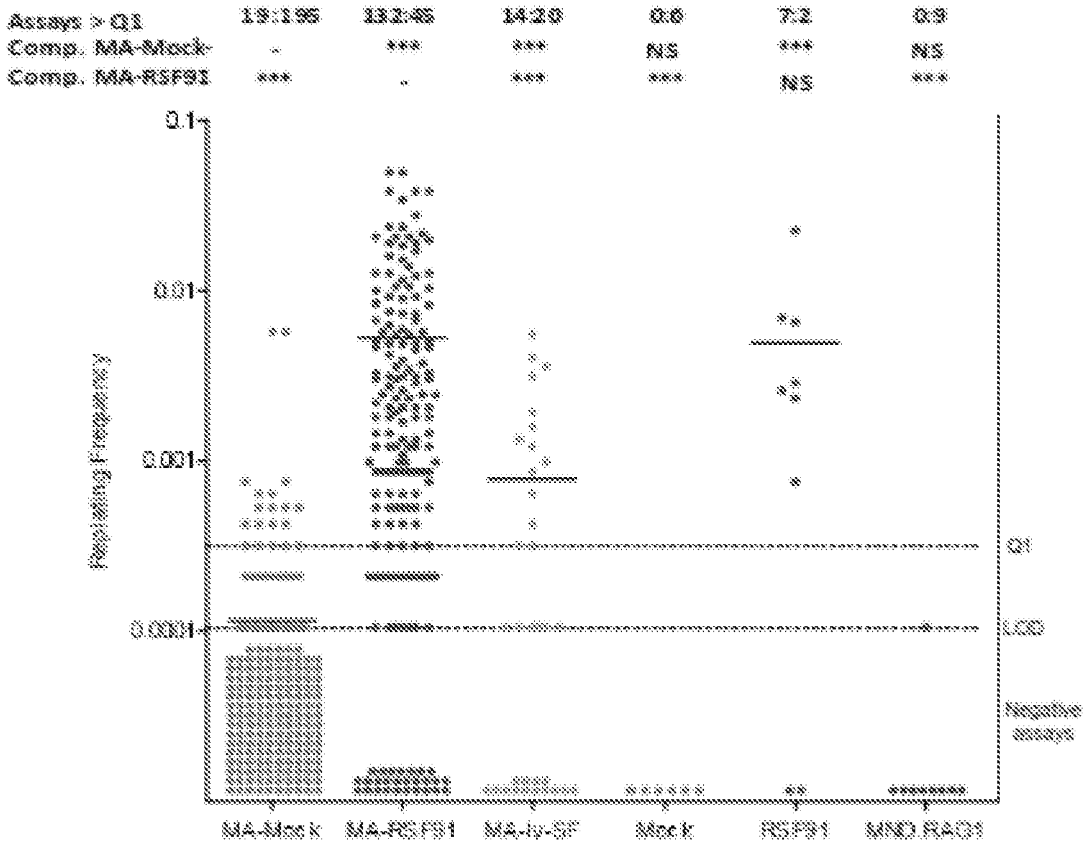

FIG. 5: Pre-clinical safety testing of the clinical grade MND-co.oRag1 vector. A). Vector biodistribution in immune and non-immune organs assessed by qPCR on DNA samples from 16 organs in total. Each dot represents a value from one mouse. B) LV insertion site analysis by nrLAM-PCR of isolated DNA from BM obtained from $Rag1^{-/-}$ untransduced control mouse (Mock) and 4 MND-c.o.RAG1 mice (male non-immunized/immunized, female non-immunized/immunized). Gels shows results of the linear amplification from the 3'LTR and 5'LTR respectively (L=1 kb plus marker). C) Replating Frequencies (RF) of the control samples Mock or RSF91 and the test vector MND-c.o.RAG1, in comparison to data of a meta-analysis for control samples (Mock-MA, RSF91-MA, lv-SF-MA [a lentiviral vector with SFFV promoter]). The data points below the limit of detection (LOD; plates with no wells above the MTT-threshold) were manually inserted into the graph (due to the logarithmic scale of the y-axis). Above the graph, the ratio of positive (left number) and negative plates (right number) according to the MTT-assay are shown. Differences in the incidence of positive and negative assays relative to Mock-MA or RSF91-MA were analysed by Fisher's exact test with Benjamini-Hochberg correction (*P<0.05; P<0.01; *P<0.001; NS=not significant). If above LOD, bars indicate mean RF.

Figure 6:
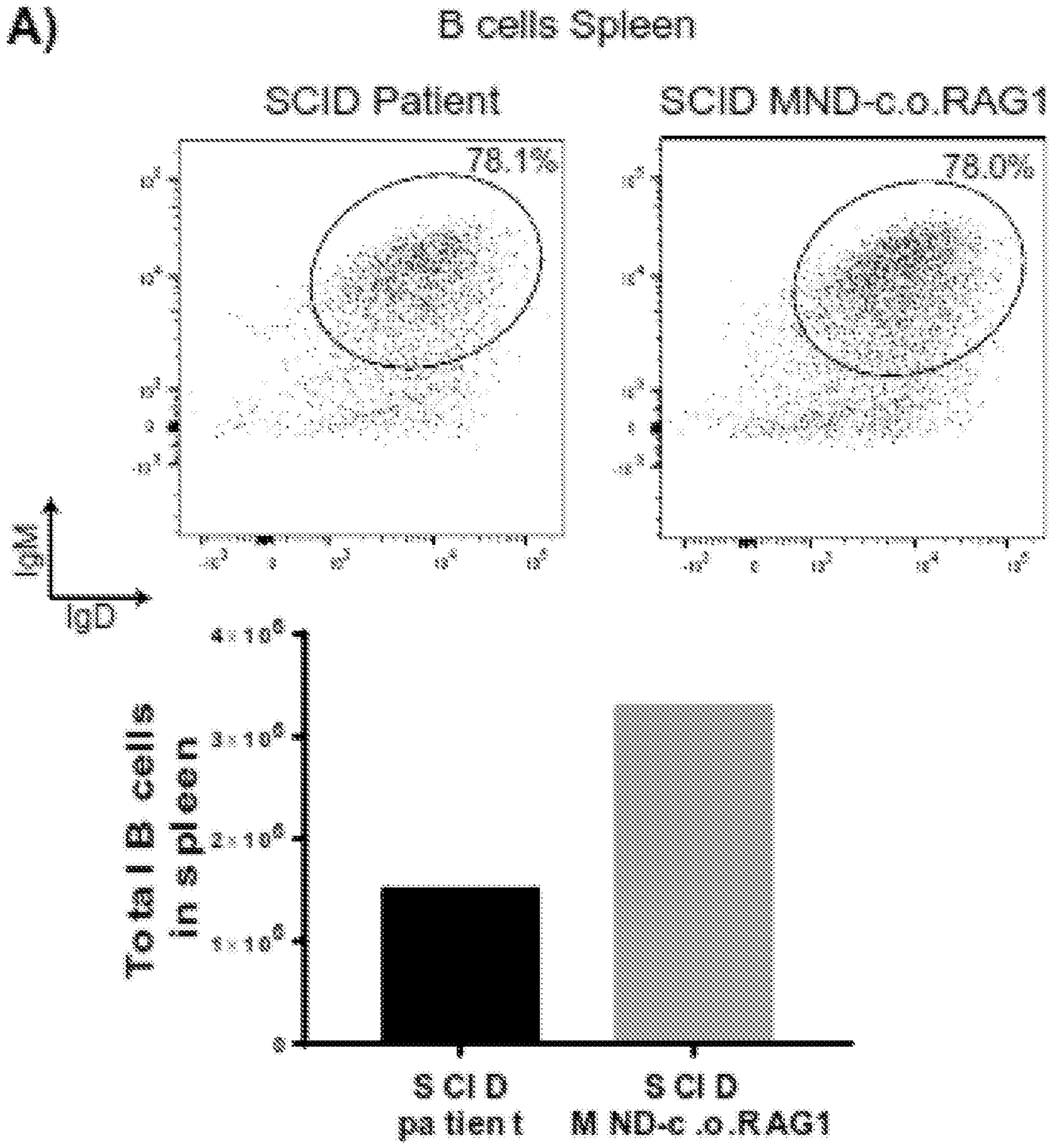
Figure 6:
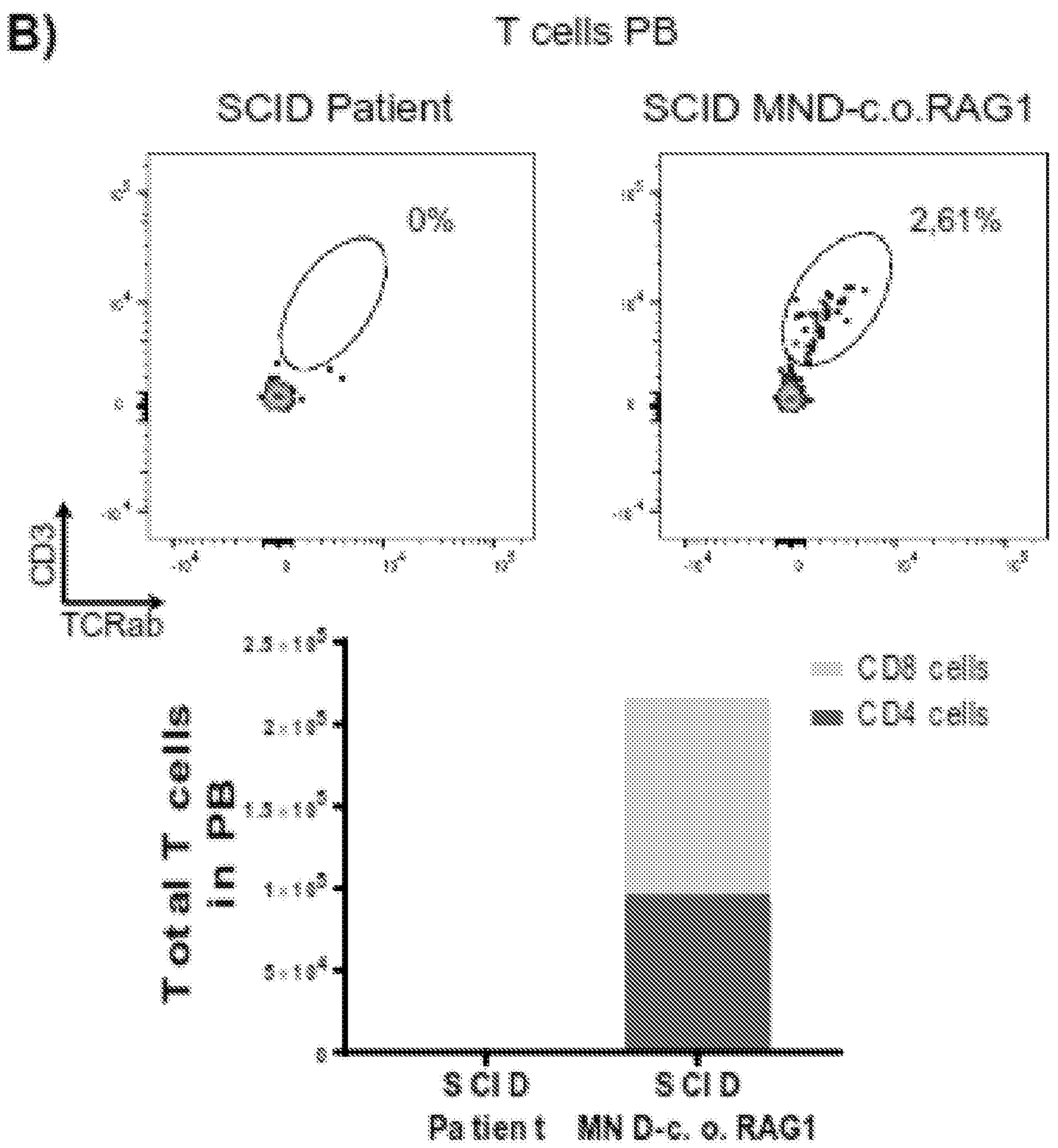
Figure 6:
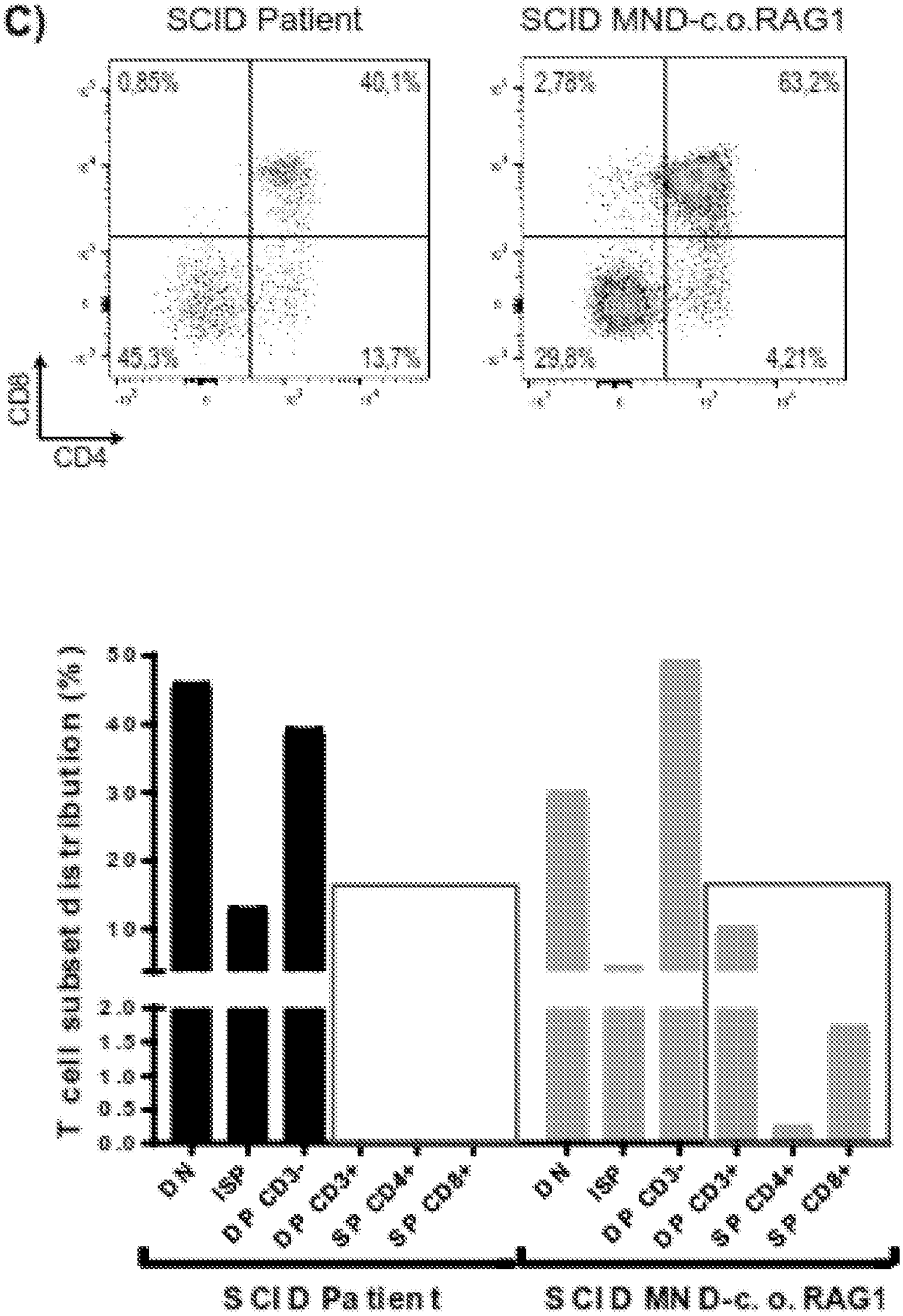
Figure 6:
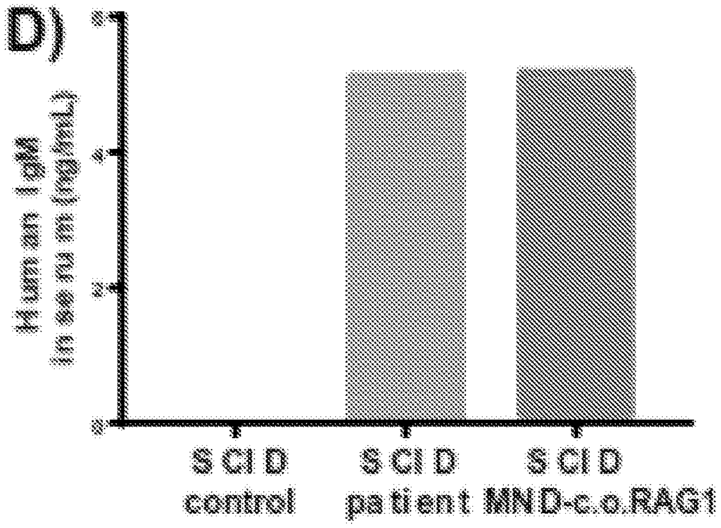
Figure 6:
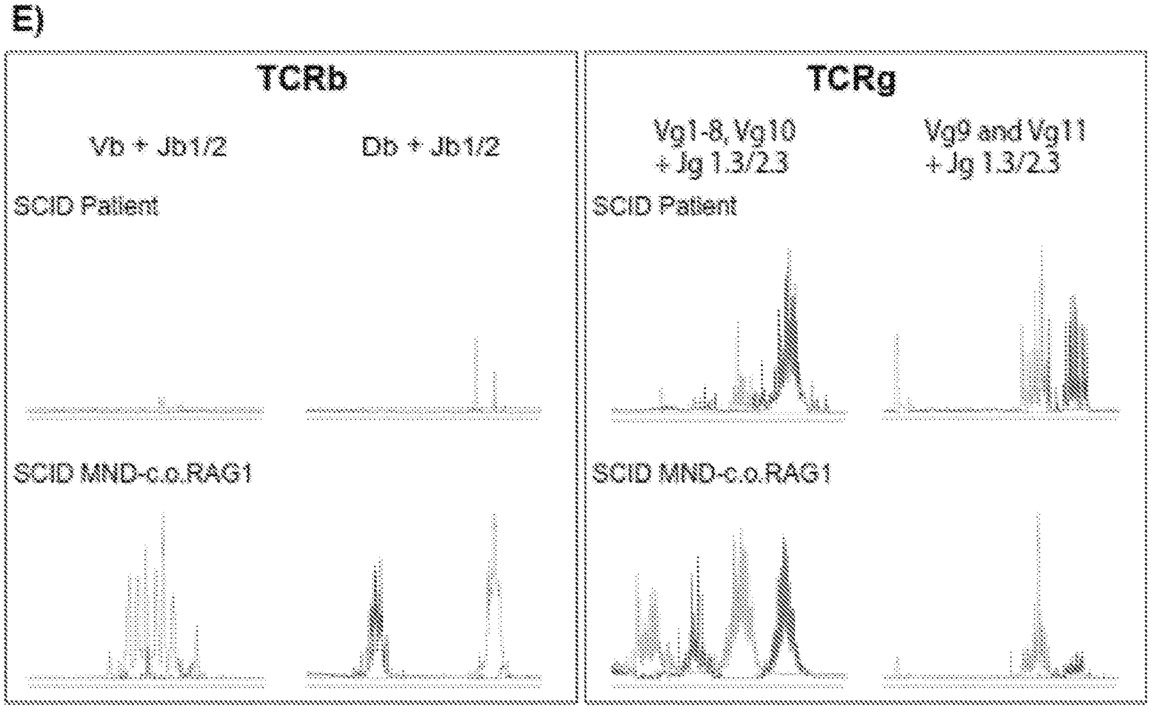
Figure 6:
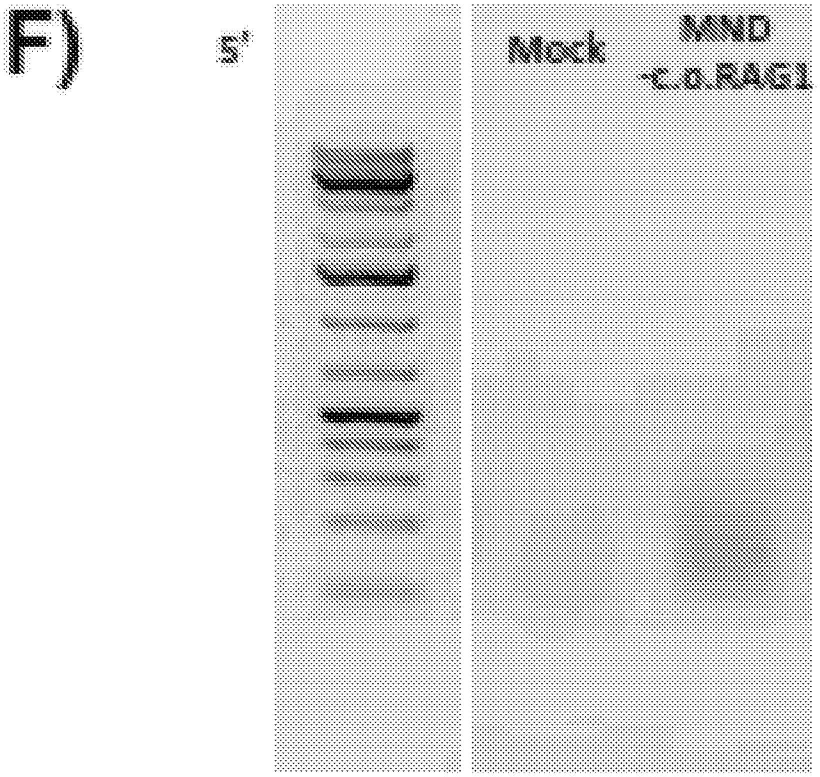

FIG. 6: Restored B and T cell development in Rag1 SCID patient cells. A). Mice were transplanted with $CD34^+$purified mock transduced cells (65,000) or MND-CoRAG1 transduced (65,000). Representative FACS plots of human B cells ($CD13/33^-CD19^+CD20^+$ cells; top panel) and total number of B cells ($CD13/33^-CD19^+CD20^+$IgD/IgM cells; bottom panel) in the spleen. B) Representative FACS plots of human T cells ($CD3^+TCR\alpha\beta^+$; top panel) and total number of T cells, CD4 and CD8 T cells, in the PB (bottom panel). C) Human T cell development in the thymus: Representative FACS plots (CD4 vs CD8) and distribution of the different T cells subsets in the thymus. D) Quantification of total human IgM by ELISA of serum from NSG mouse transplanted with SCID control $CD34^+$ cells, SCID patient $CD34^+$ cells and SCID MND-c.o.RAG1 $CD34^+$ cells. E) Human TCR Vβ and Vγ repertoire analysis of isolated DNA from NSG thymus (SCID patient and SCID MND-c.o.RAG1) using TCRB+TCRG T-Cell Clonality Assay. (x-axis indicates fragment sizes; y-axis shows the fluorescence intensity of the runoff products) F) LV insertion site analysis by nrLAM-PCR of isolated DNA from BM obtained from NSG SCID patient untransduced cells (Mock) and NSG SCID MND-c.o.RAG1 mouse. Gel shows results of the linear amplification from the 5'LTR (L=1 kb plus marker). Data from an independent experiment with n=1 per condition.

Figure 7:
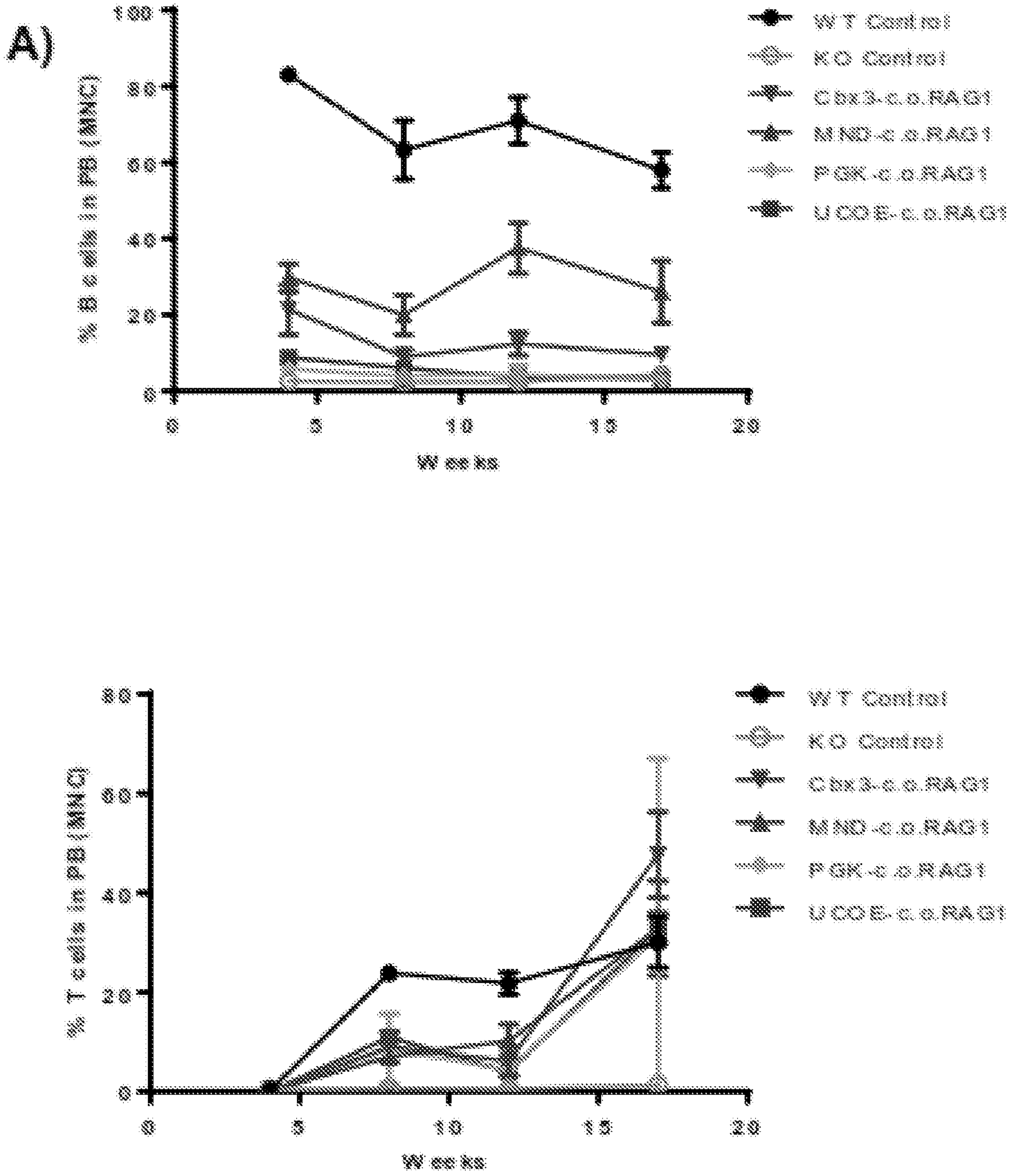
Figure 7:
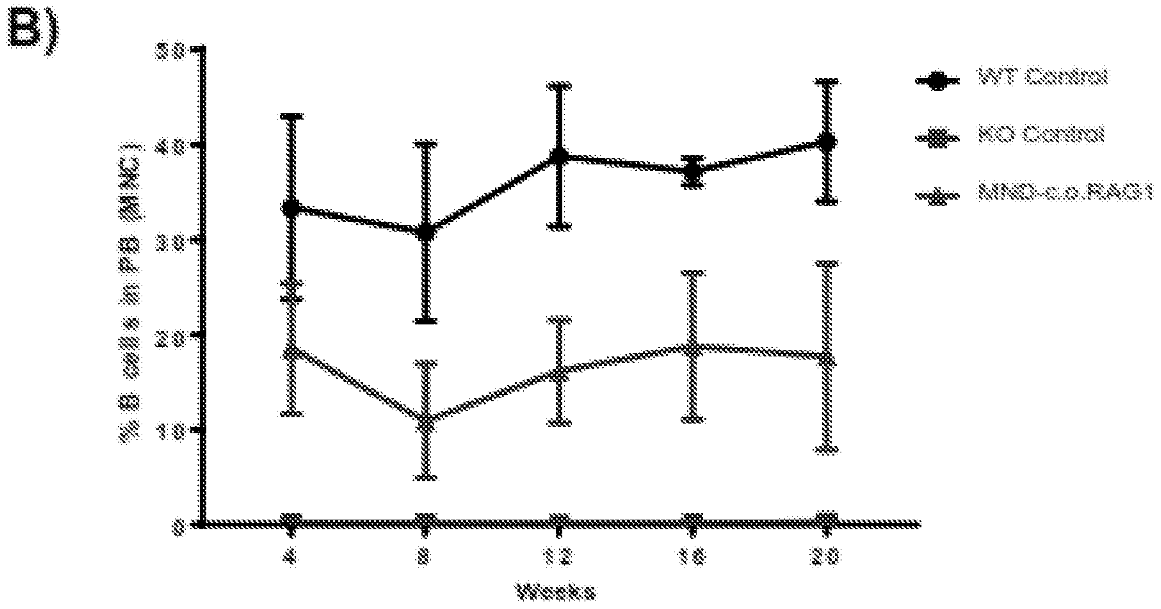
Figure 7:
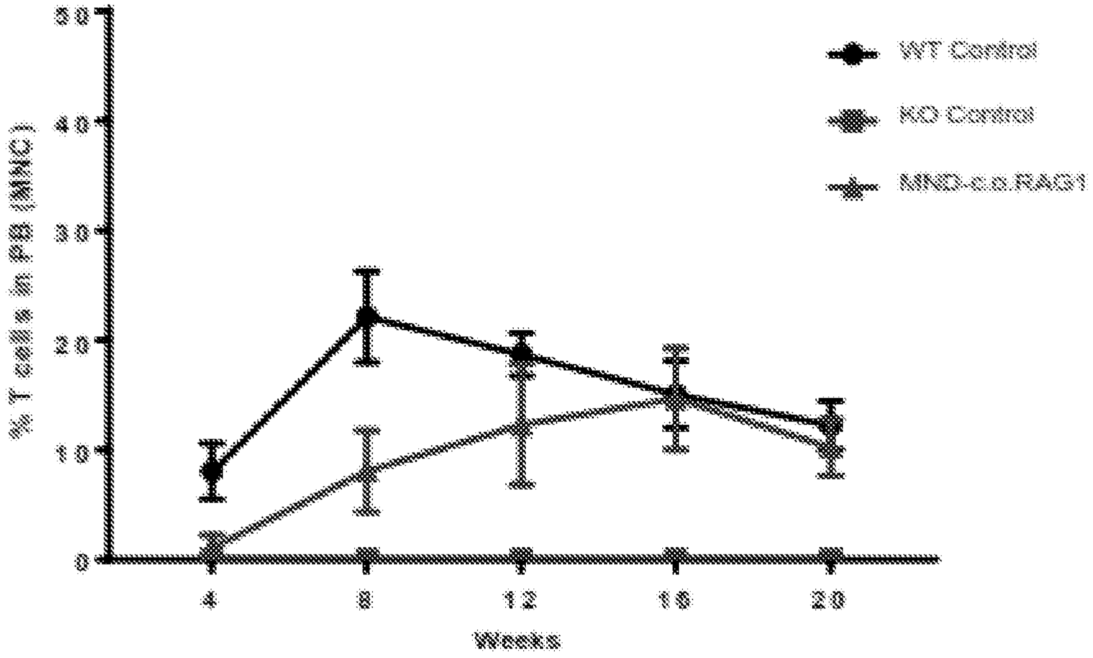
Figure 7:
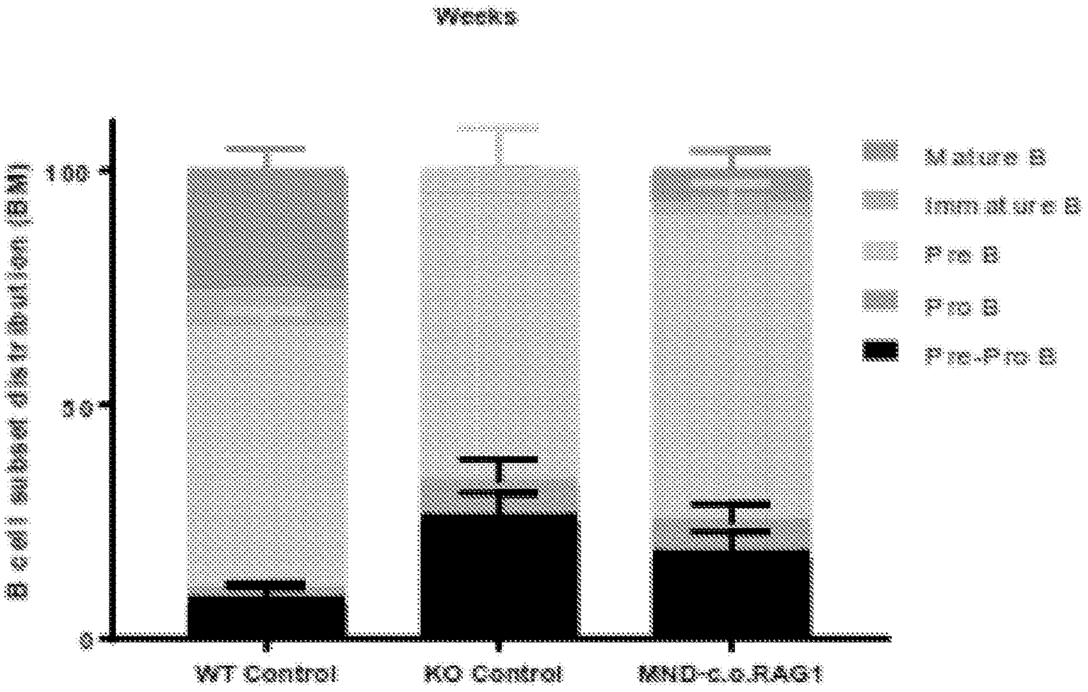
Figure 7:
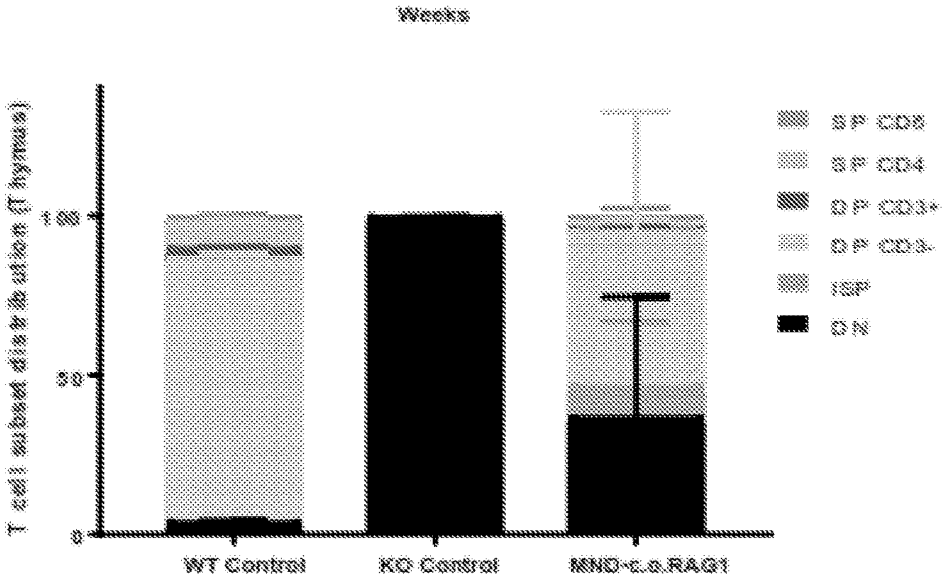
Figure 7:
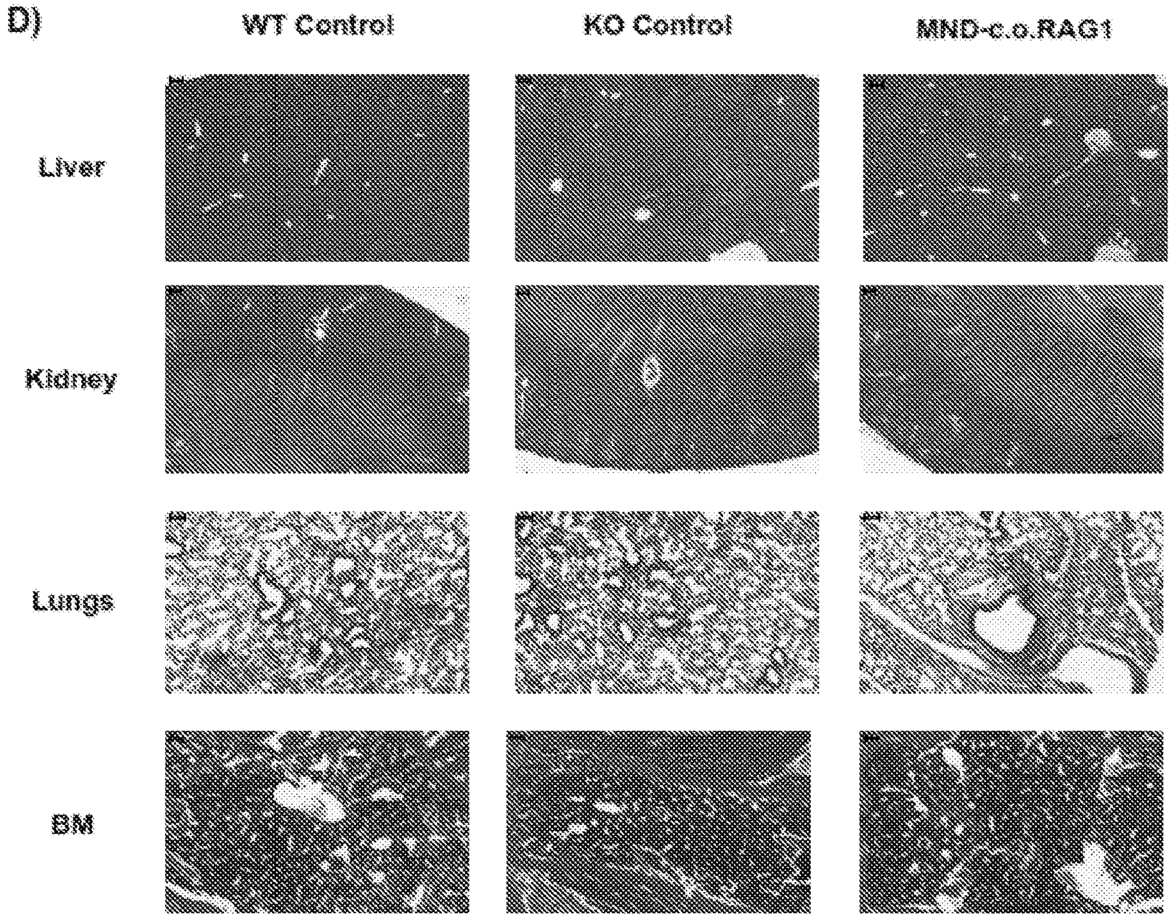
Figure 7:
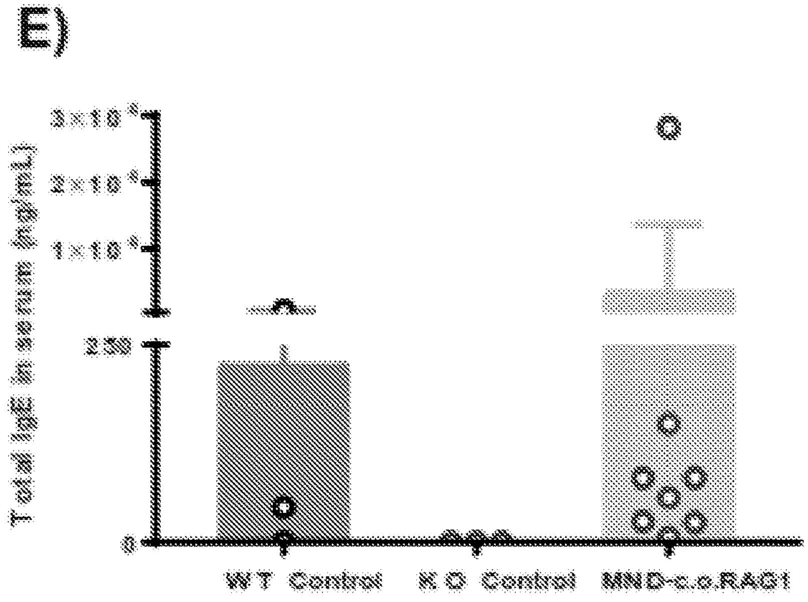

FIG. 7 shows Immune development after gene therapy in Rag1−/− mouse model.

A) Percentage of B cells ($CD11b/CD43^-B220^+$ cells; left panel) and T cells ($CD3^+TCR\alpha\beta^+$ cells; right panel) over time in PB after SC transplantation with the different constructs (Cbx3-c.o.RAG!, MND-c.o.RAG1, PGK-c.o.RAG1 and UCOE-c.o.RAG1). B) Percentage of B cells ($CD11b/CD43^-B220^+$ cells; left panel) and T cells ($CD3^+TCR\alpha\beta^+$ cells; right panel) over time in PB after SC transplantation with the clinical MND-c.o.RAG1 batch C) B cell development subsets distribution in BM (left panel) and T cell development populations distribution in the thymus (right panel) 20 weeks after SC transplantation. Graphs represent the means and standard deviation of 3 mice for control groups and 8 mice in the gene therapy group. D) Histologic analysis of the liver (scale bar=100 μm), kidney (scale bar=200 μm), lungs (scale bar=100 μm) and BM (scale=100 μm) stained with hematoxylin and eosin. Representative images from WT Control, KO Control and MND-c.o.RAG1 mice. E) Quantification of total IgE in serum by ELISA. Each dot represents a value obtained in one mouse. One-way ANOVA test *p<0.05.

Figure 8:
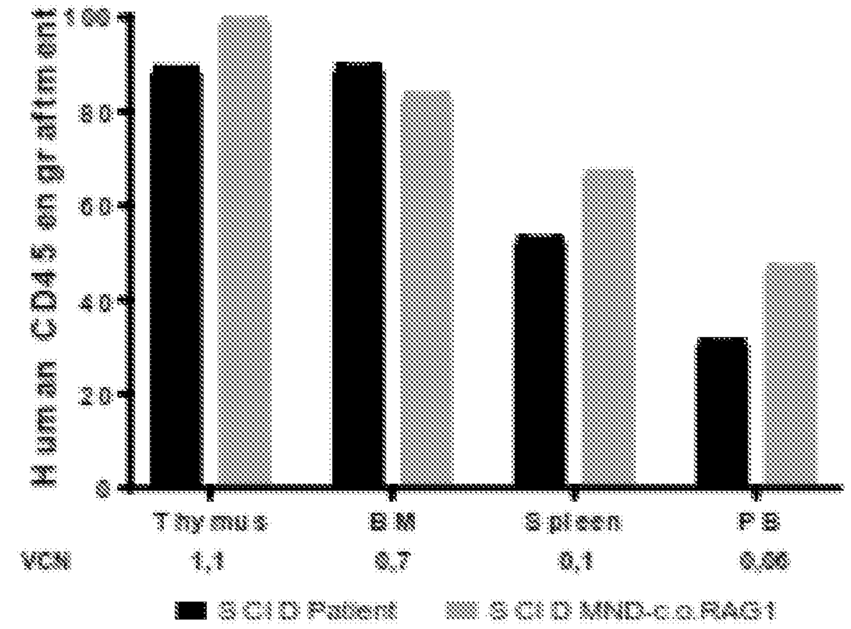
Figure 8:
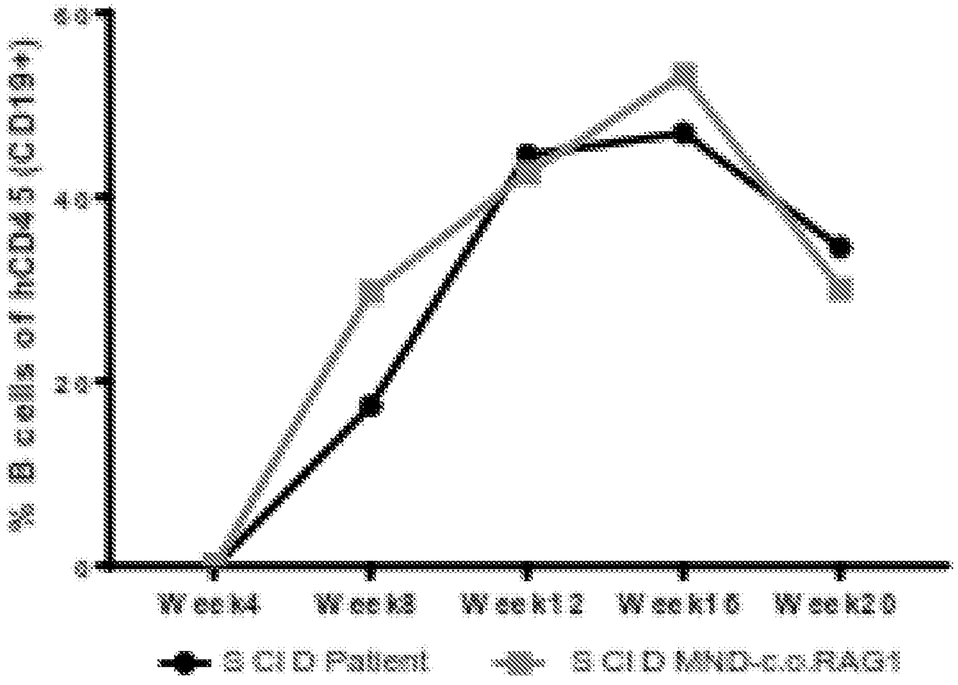
Figure 8:
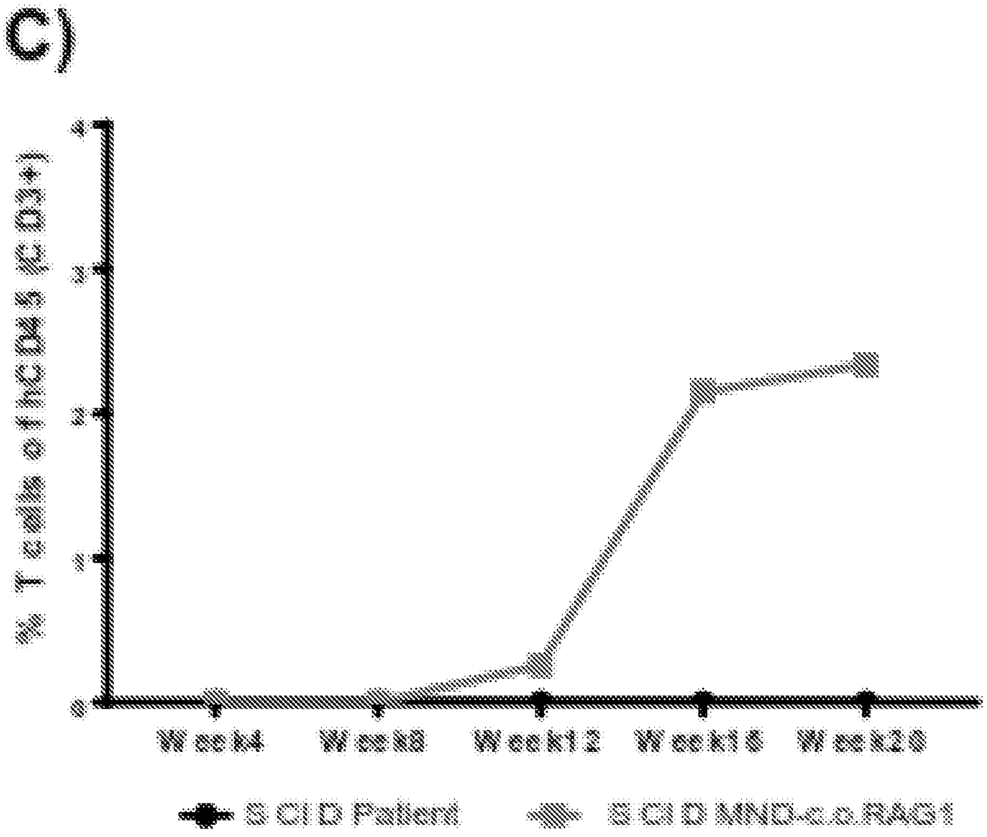
Figure 8:
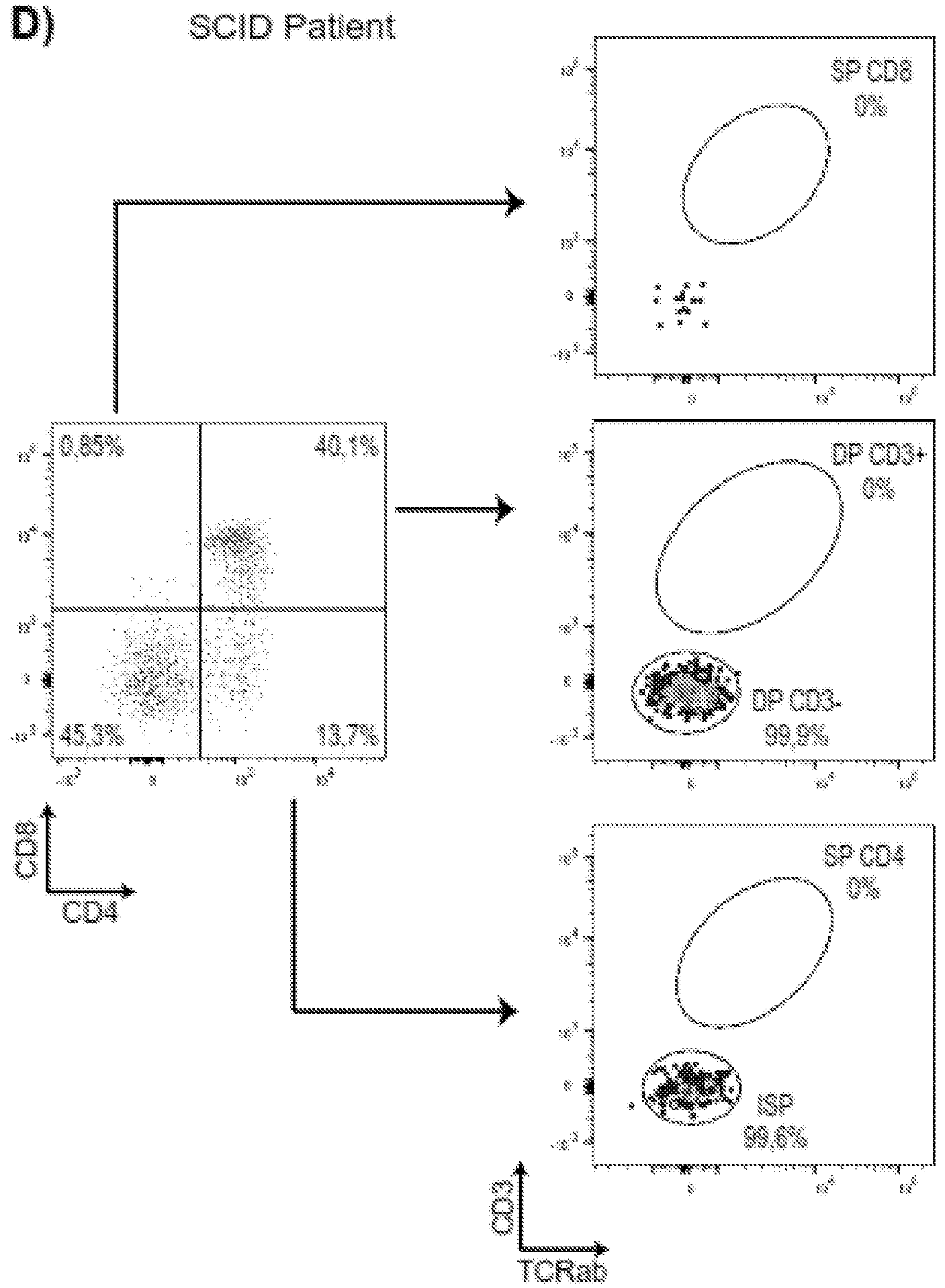
Figure 8:
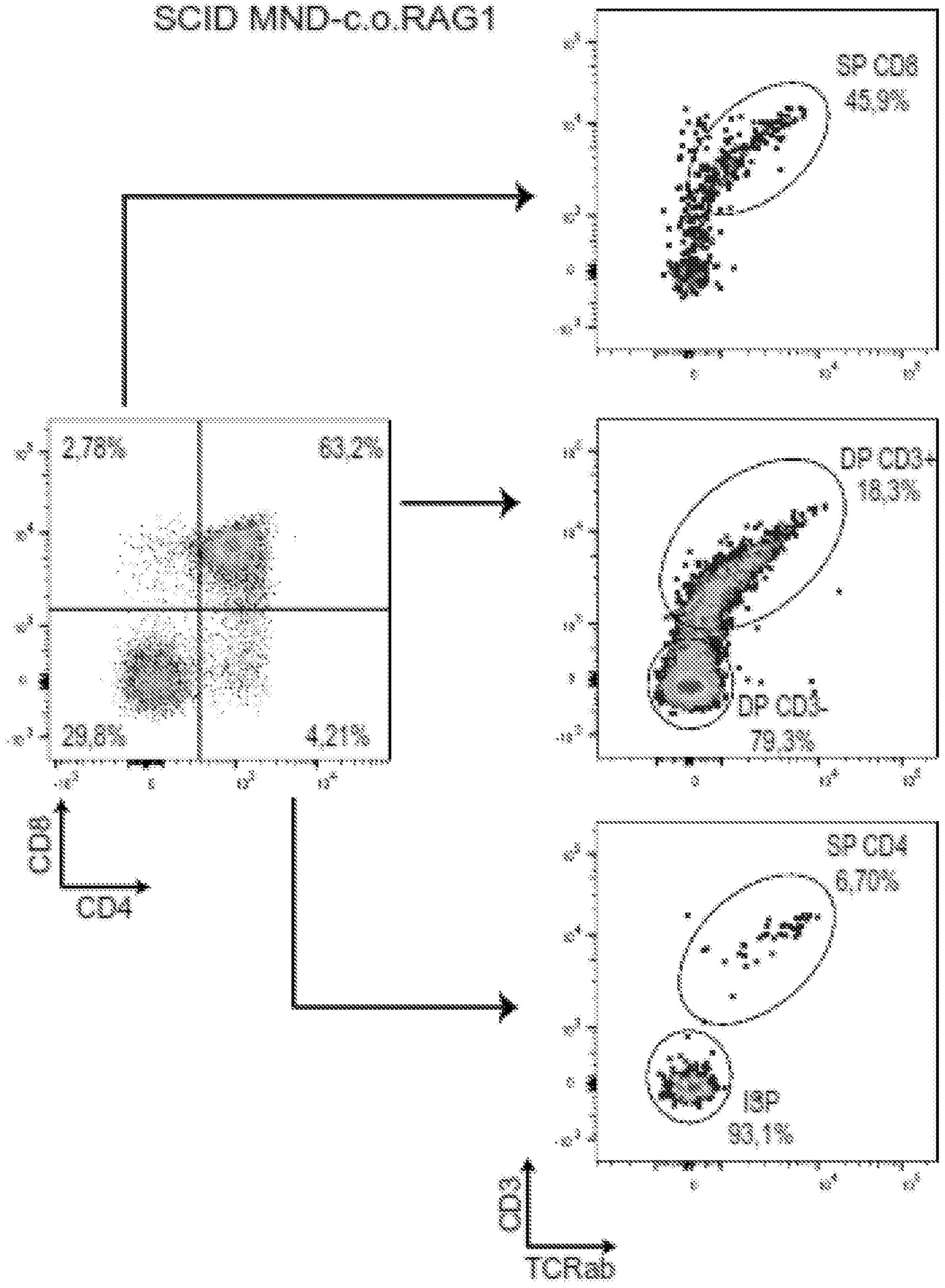
Figure 8:
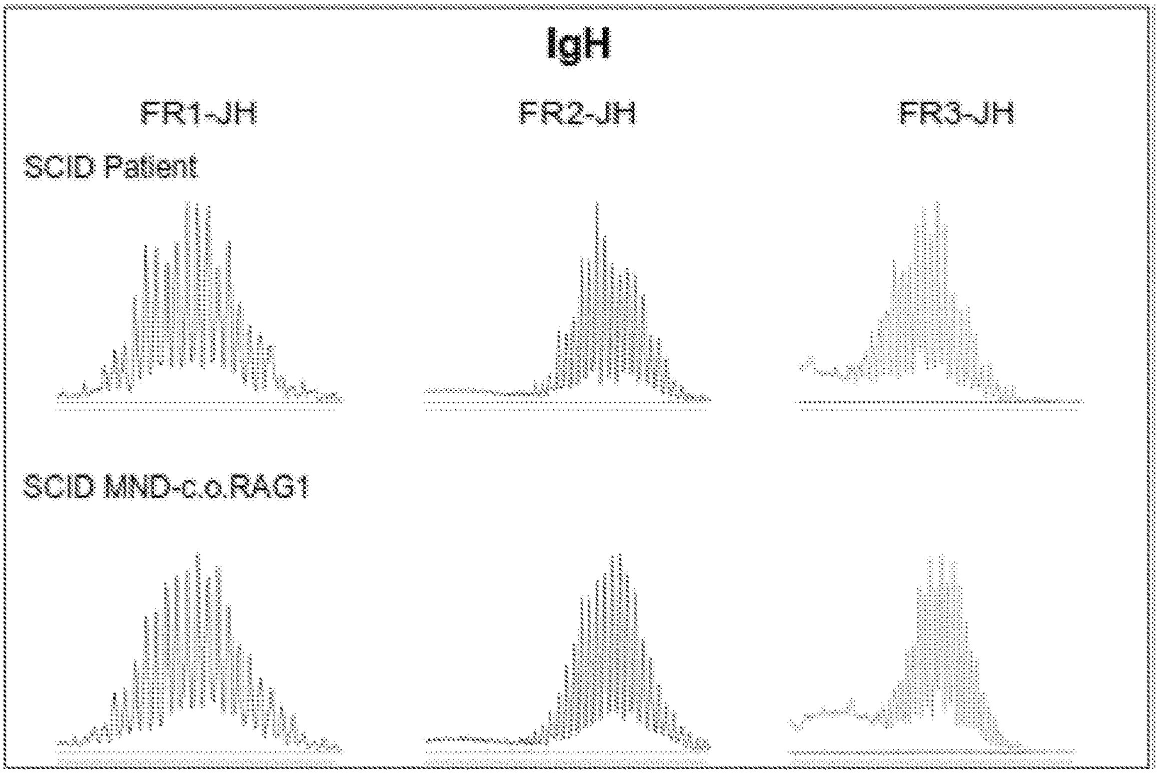
Figure 8:
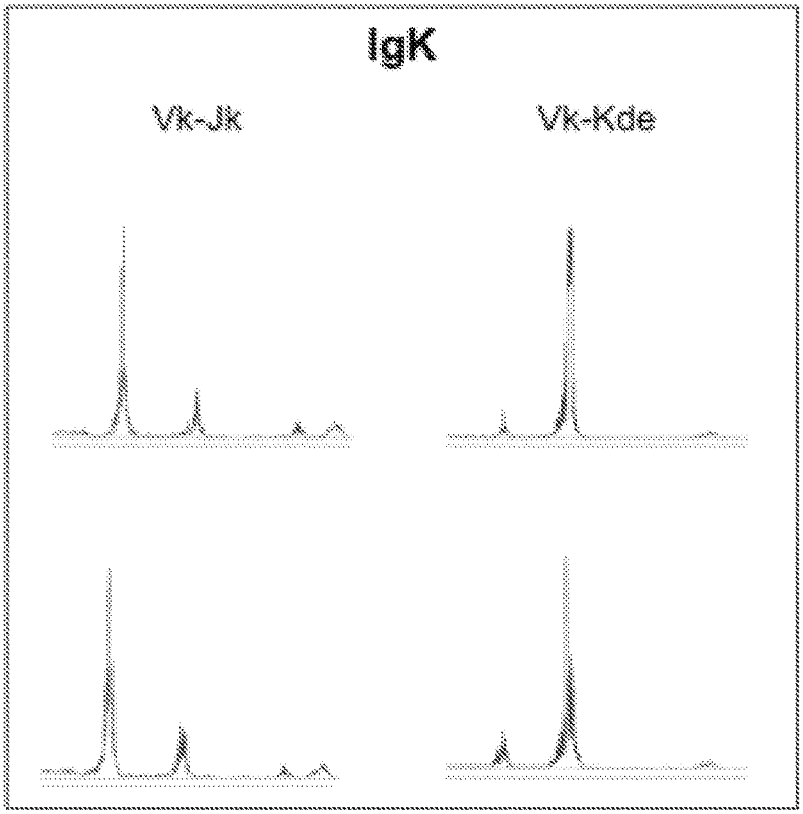

FIG. 8 shows human immune reconstitution after $CD34^+$ MND-c.o.RAG1 transplantation.

A) Percentage of human chimerism ($hCD45^+/(hCD45^+ mCD45^+)$) in immune organs of NSG mice transplanted with $CD34^+$SCID patient cells and $CD34^+$SCID patient cells transduced with MND-c.o.RAG1, 24 weeks after transplantation (1 NSG mouse per condition). B) Over-time human B cell percentage ($CD19^+$ cells per total $hCD45^+$ cells) in peripheral blood during transplantation. C) Over-time human T cell development ($CD3^+$ cells per total $hCD45^+$ cells) in PB during transplantation. D) Flow cytometry analysis of thymocytes 24 weeks after transplantation showing T cell development through the different stages. E) Human IgH and IgK repertoire analysis of isolated DNA from NSG BM (SCID patient and SCID MND-c.o.RAG1) using IgH+IgK B-Cell Clonality Assay. (x-axis indicates fragment sizes; y-axis shows the fluorescence intensity of the runoff products).

Figure 9:
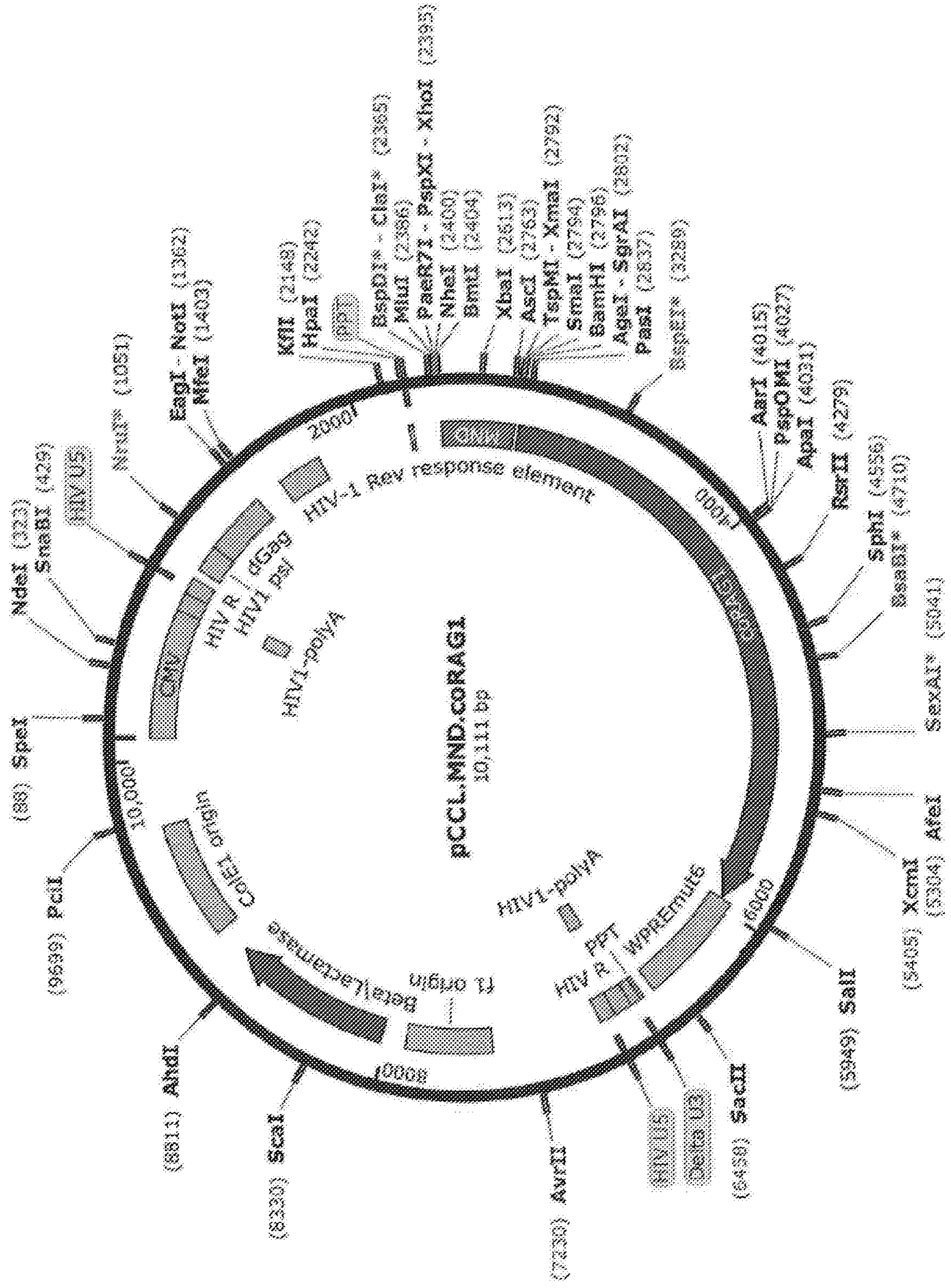
Figure 9:
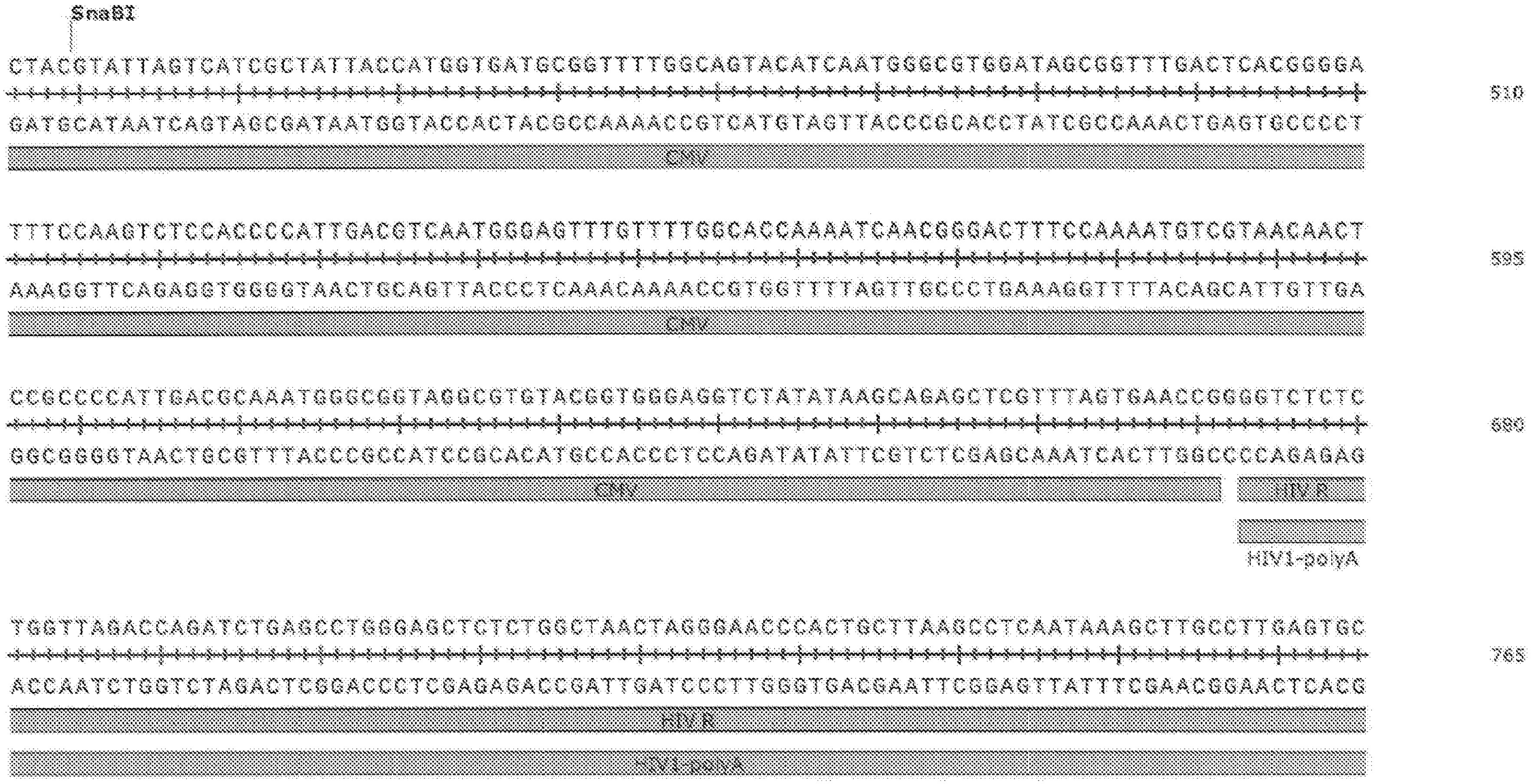
Figure 9:
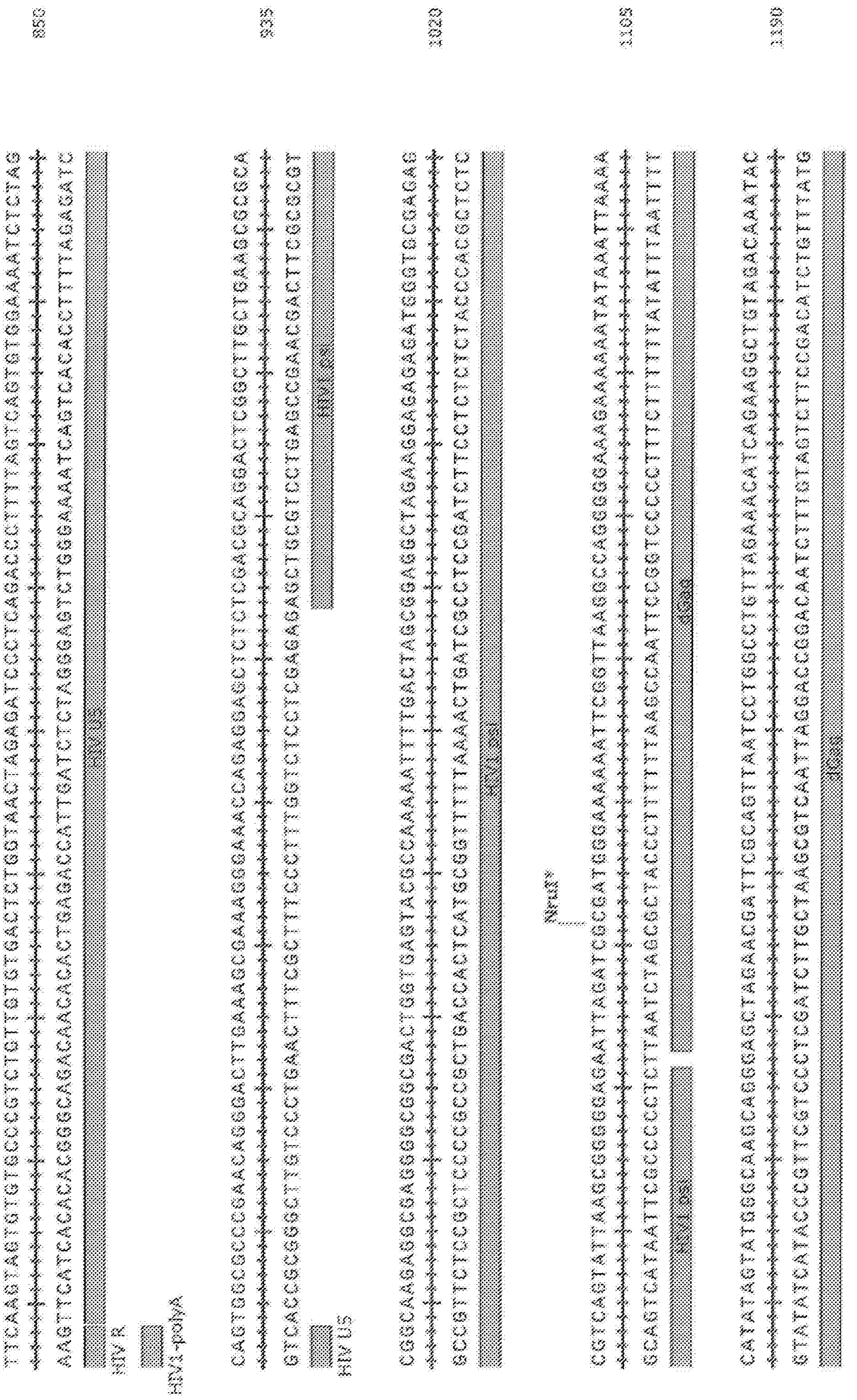
Figure 9:
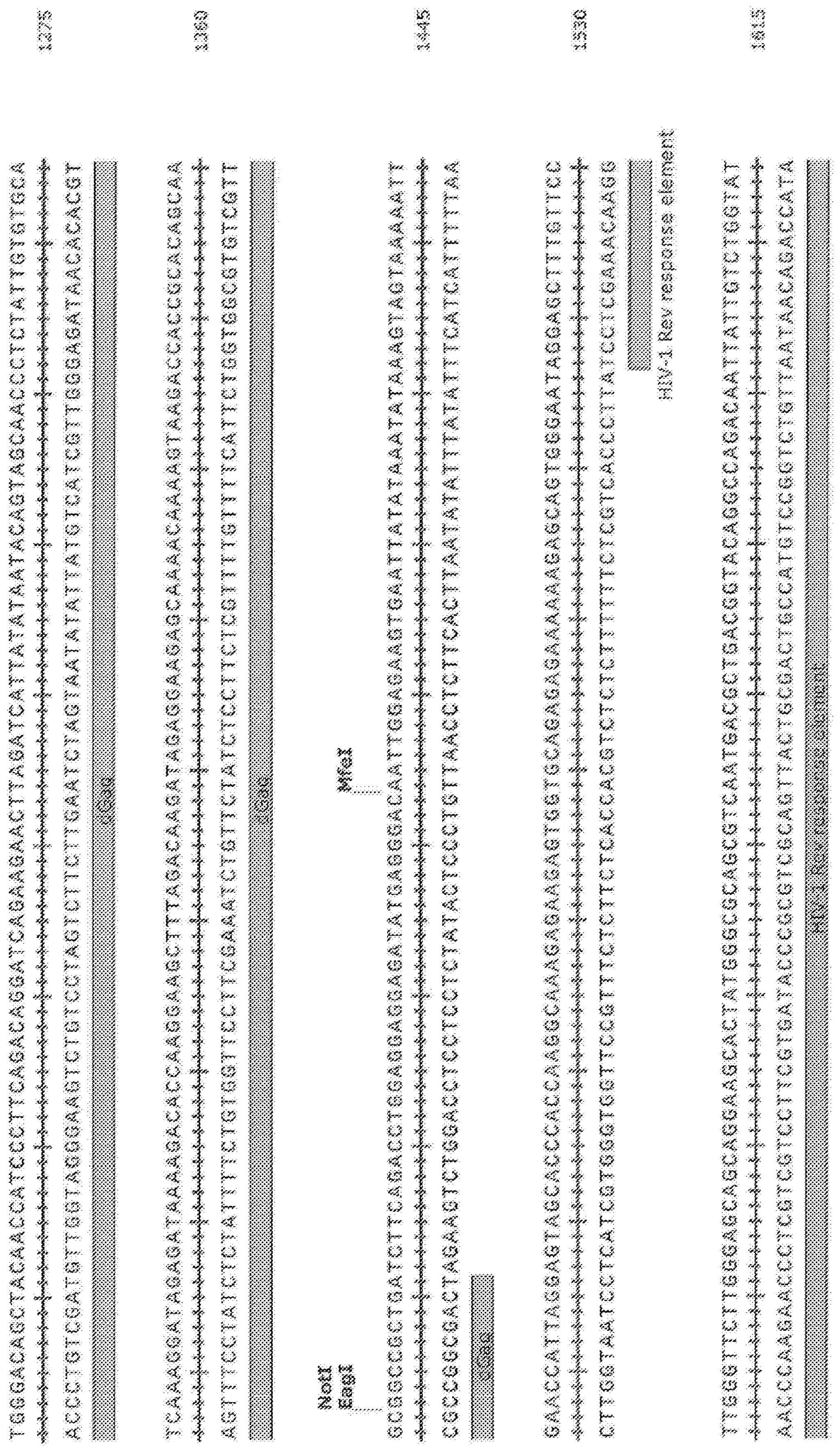
Figure 9:
Figure 9:
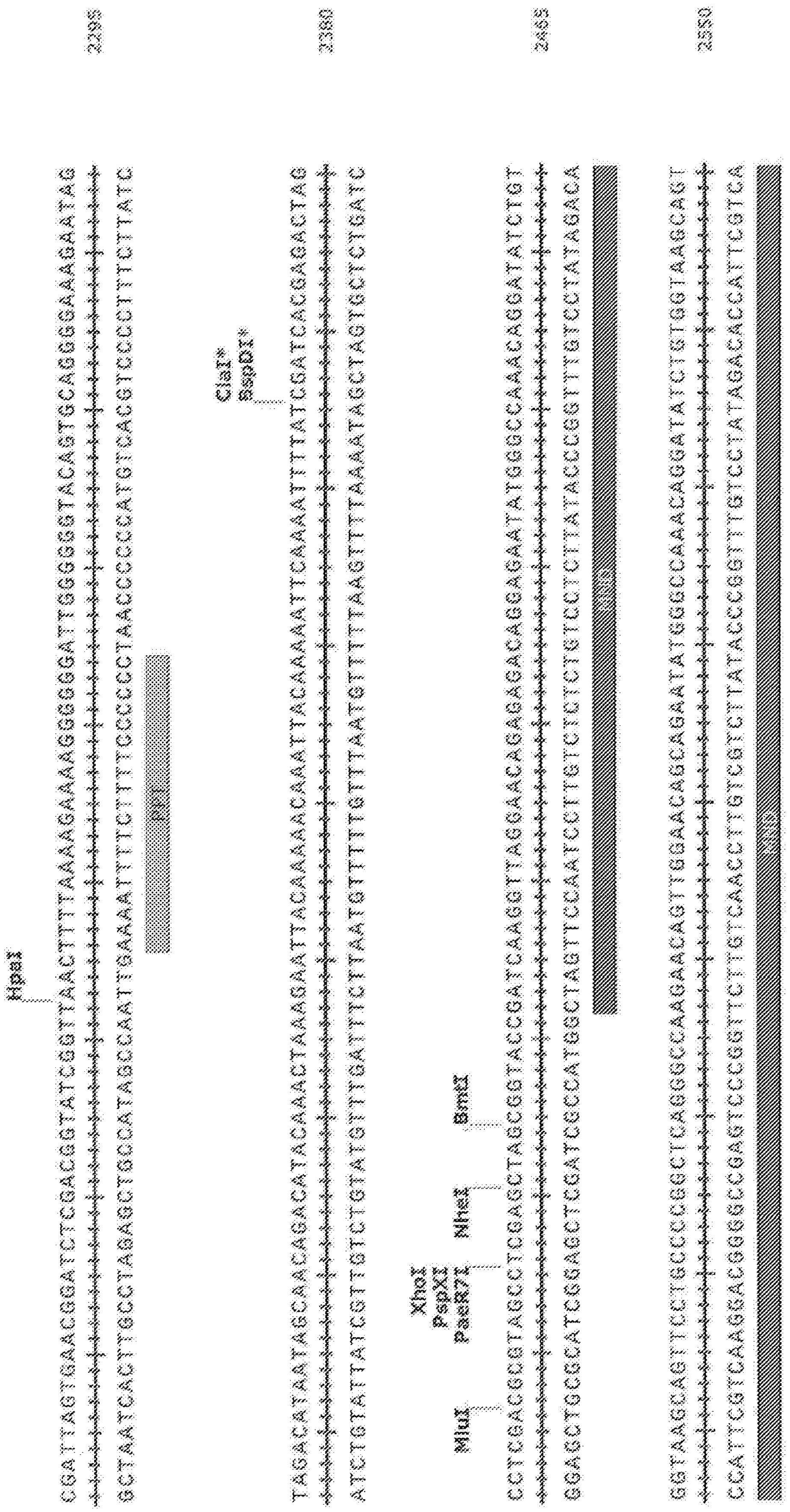
Figure 9:
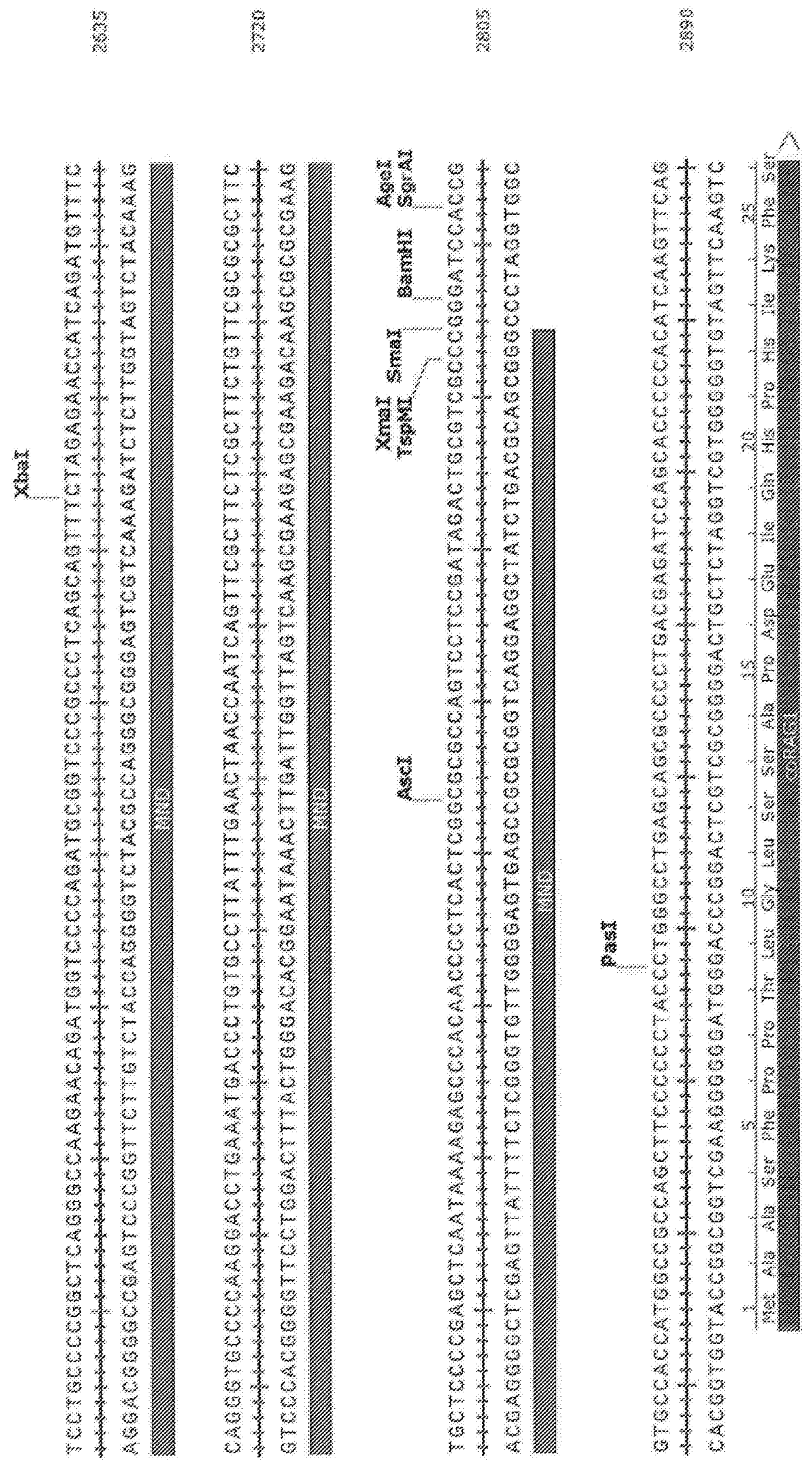
Figure 9:
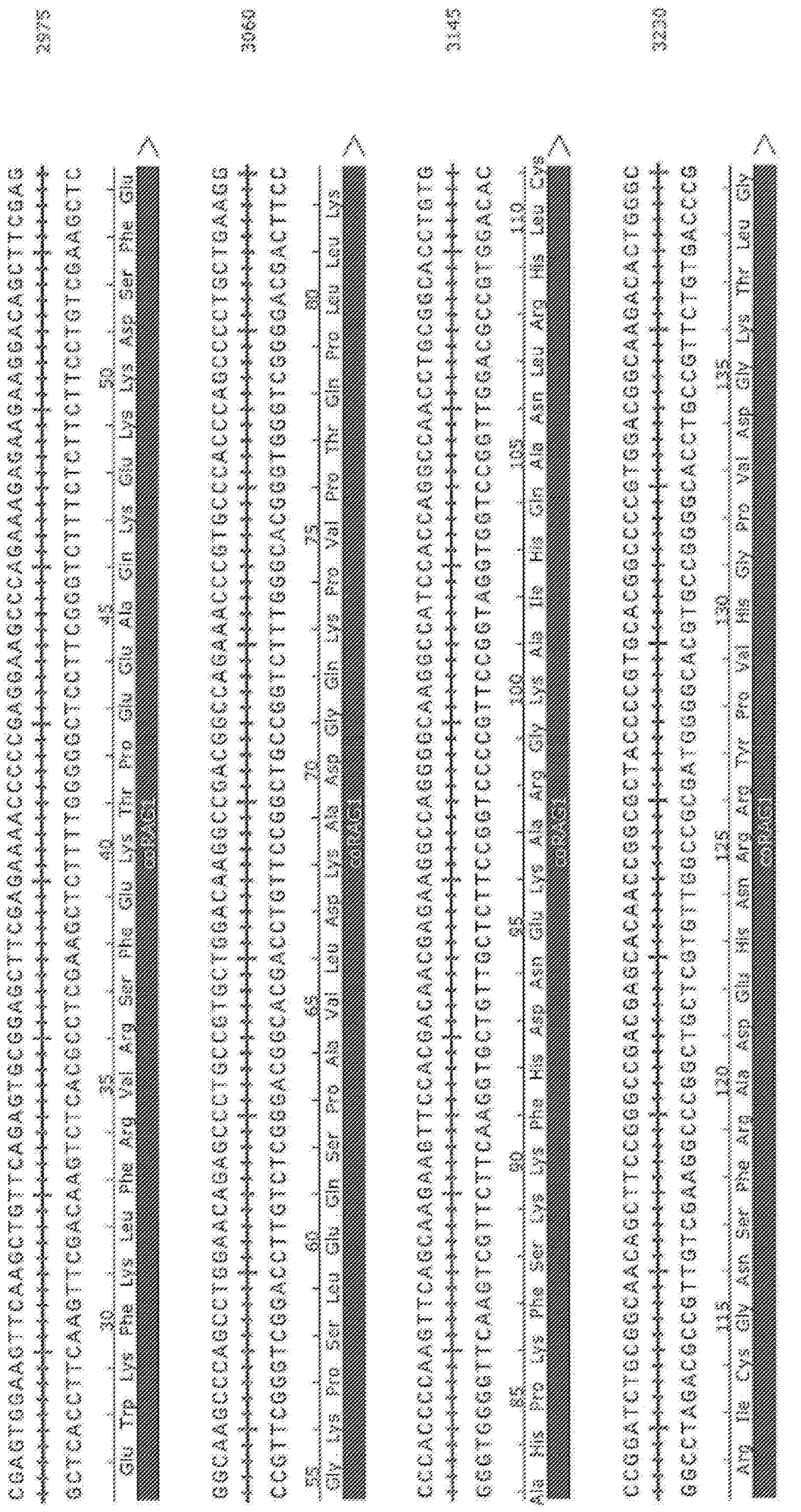
Figure 9:
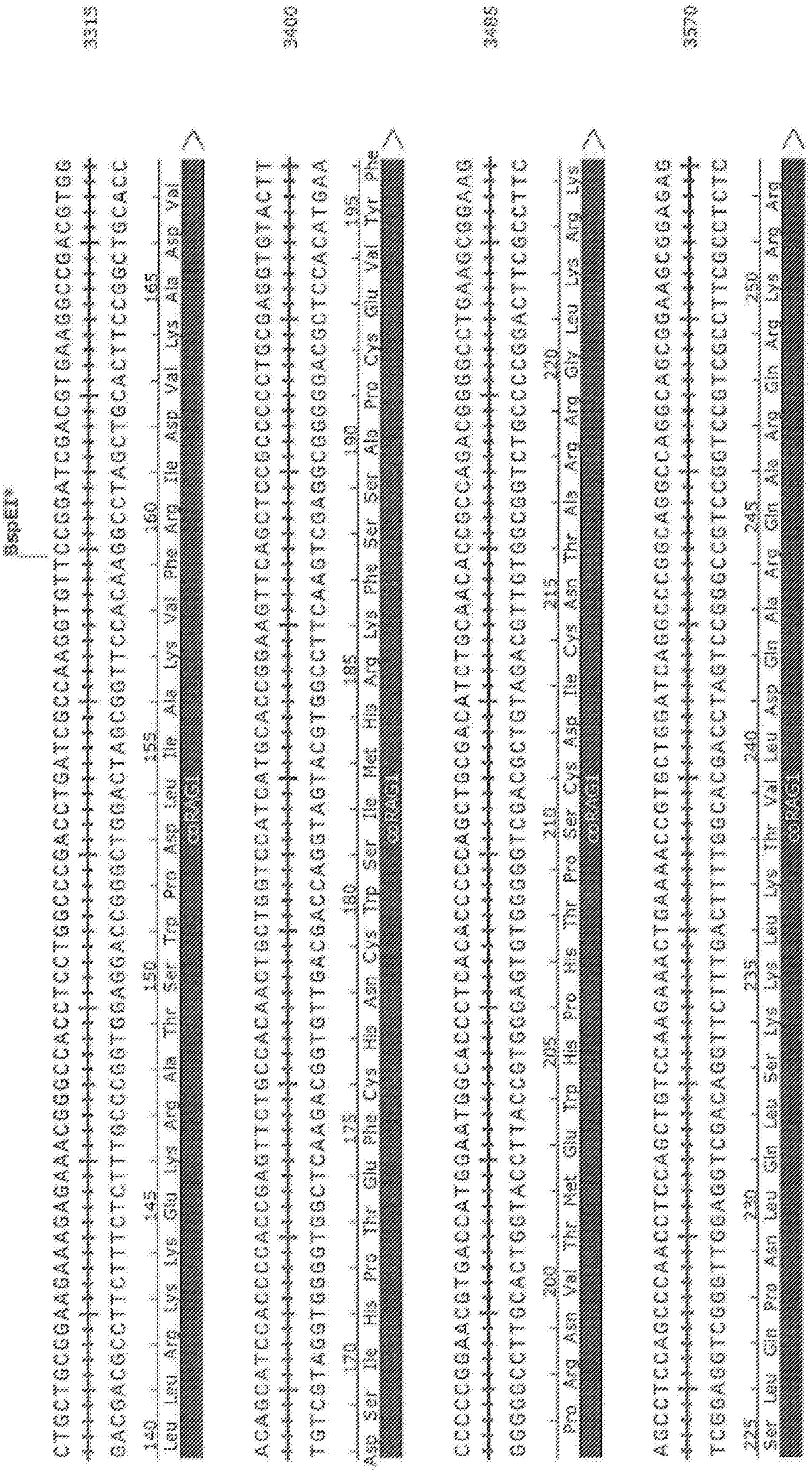
Figure 9:
Figure 9:
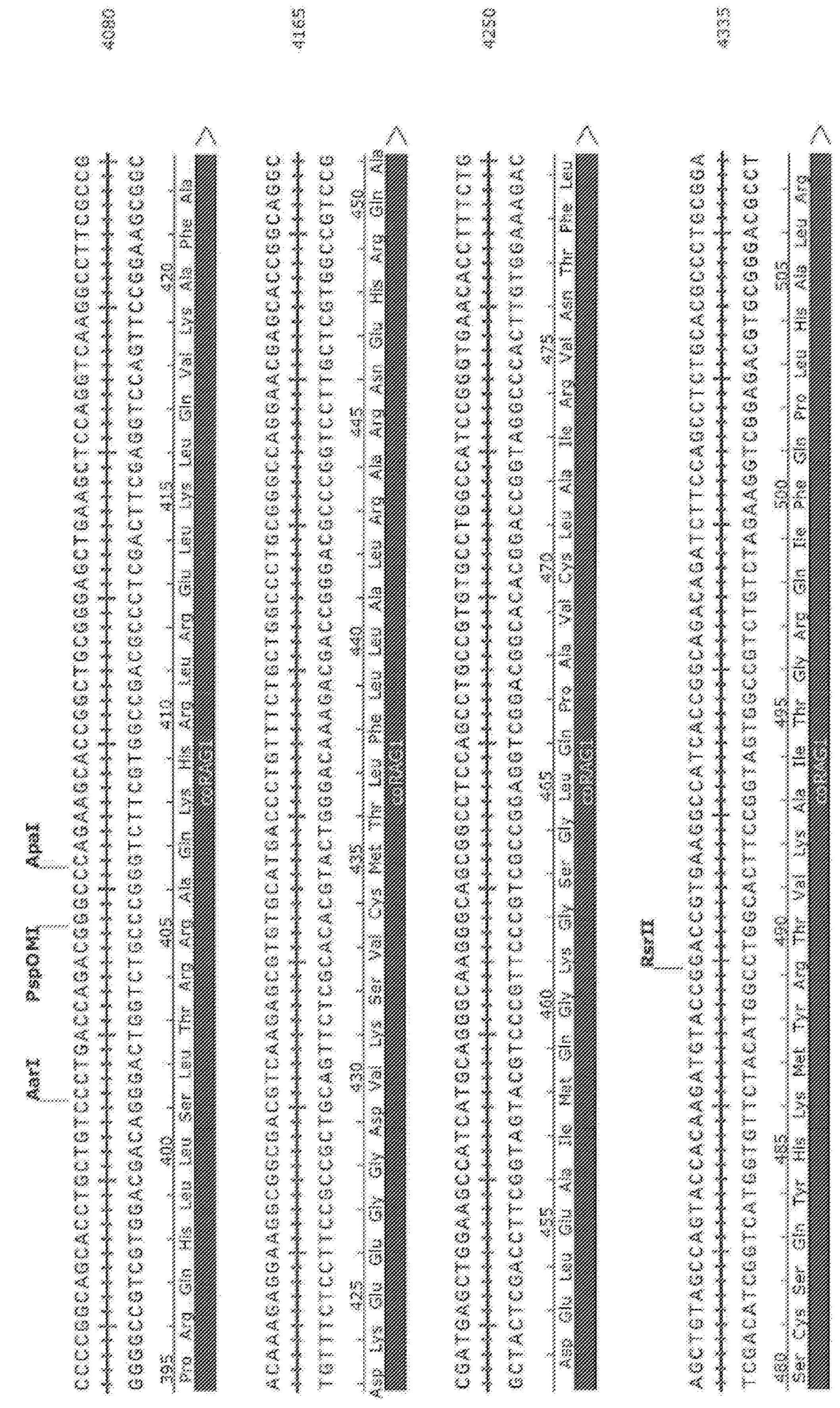
Figure 9:
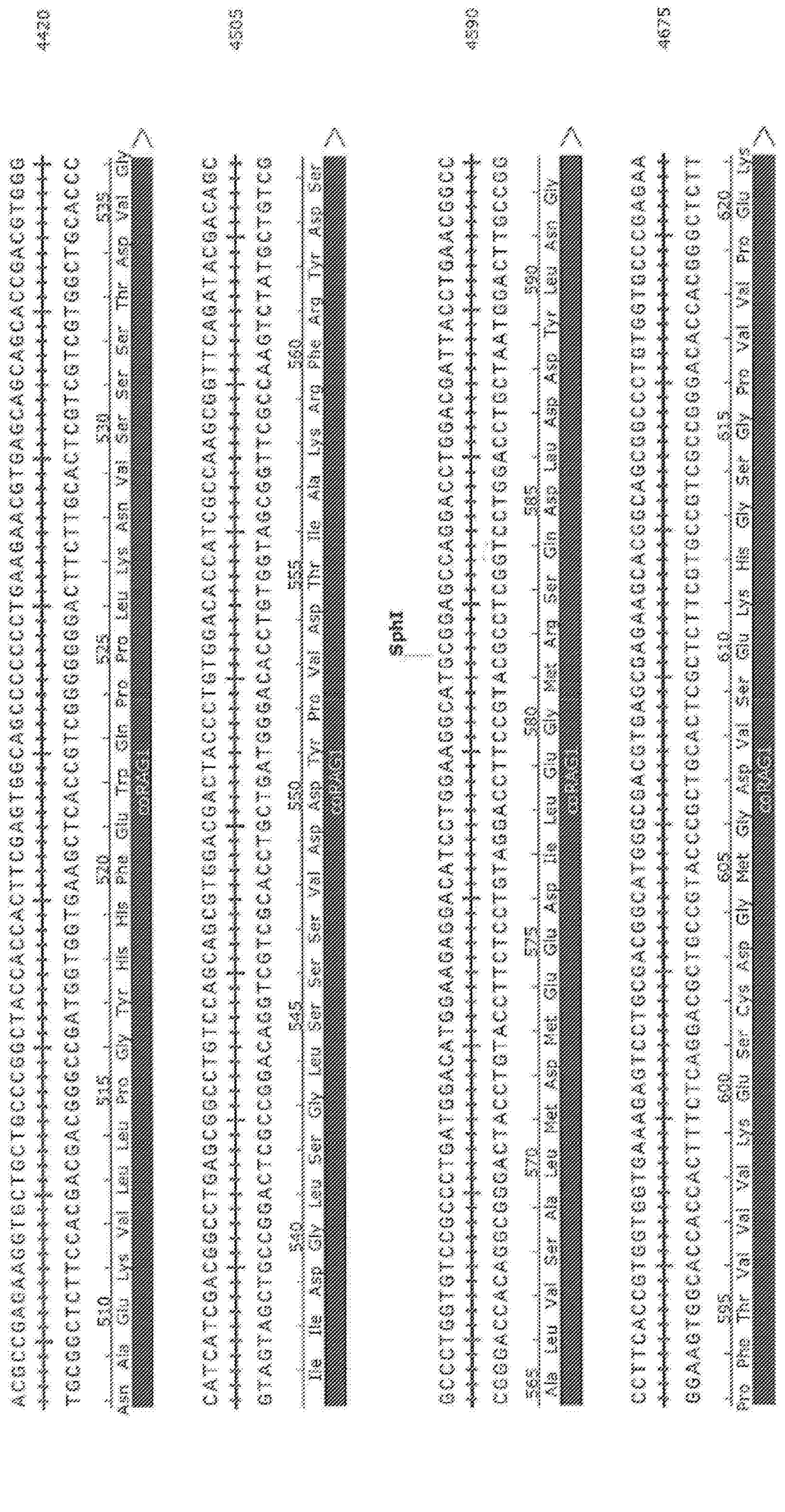
Figure 9:
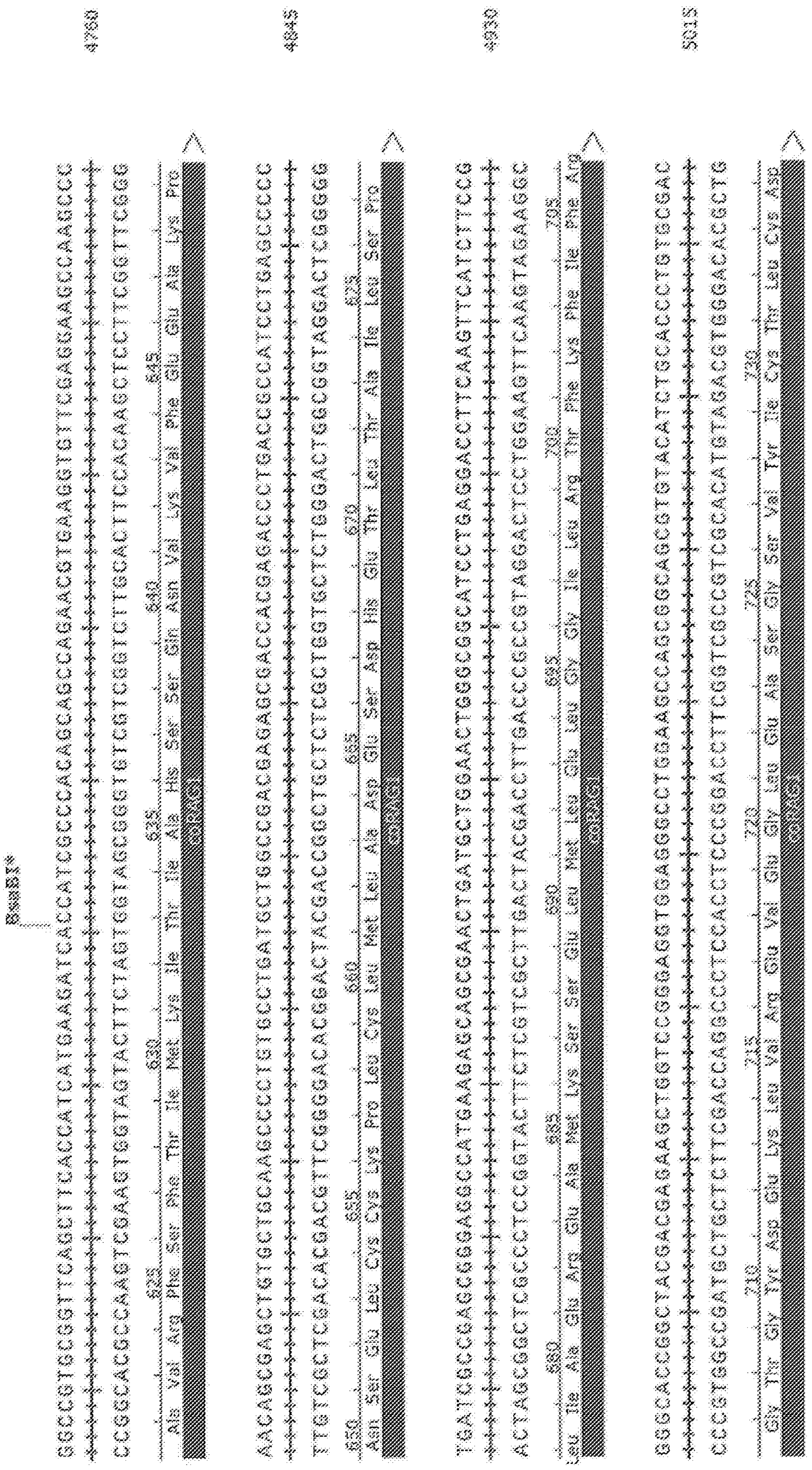
Figure 9:
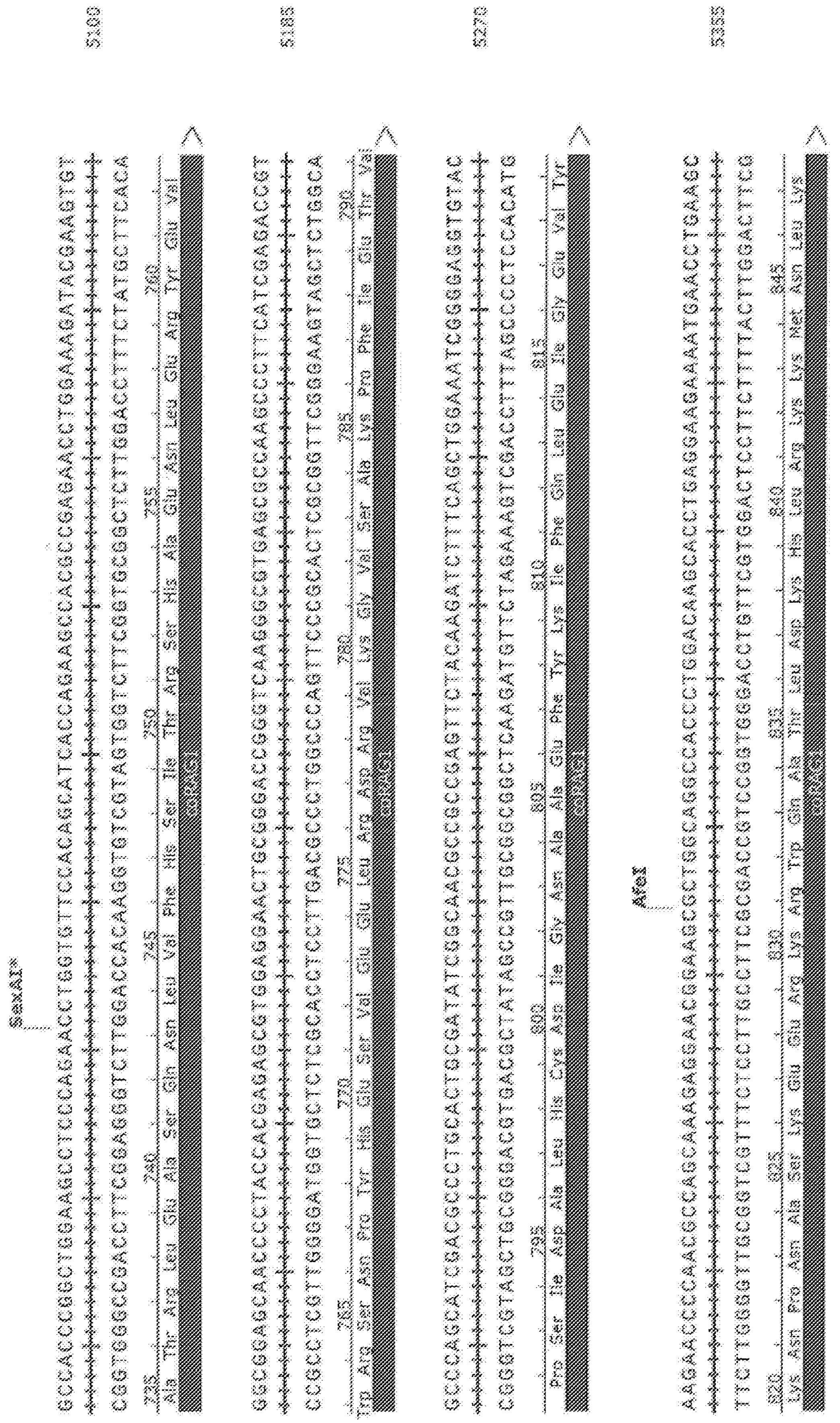
Figure 9:
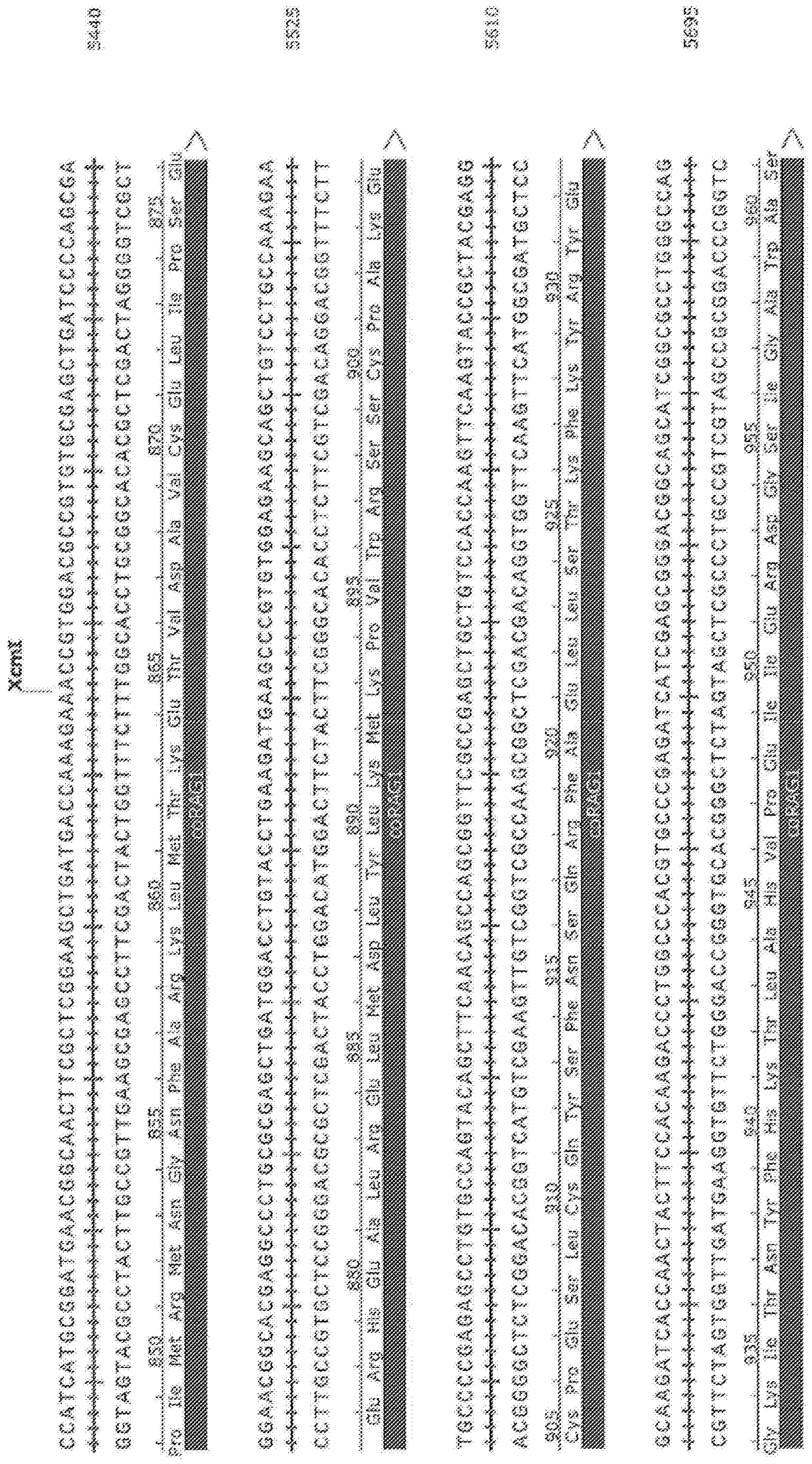
Figure 9:
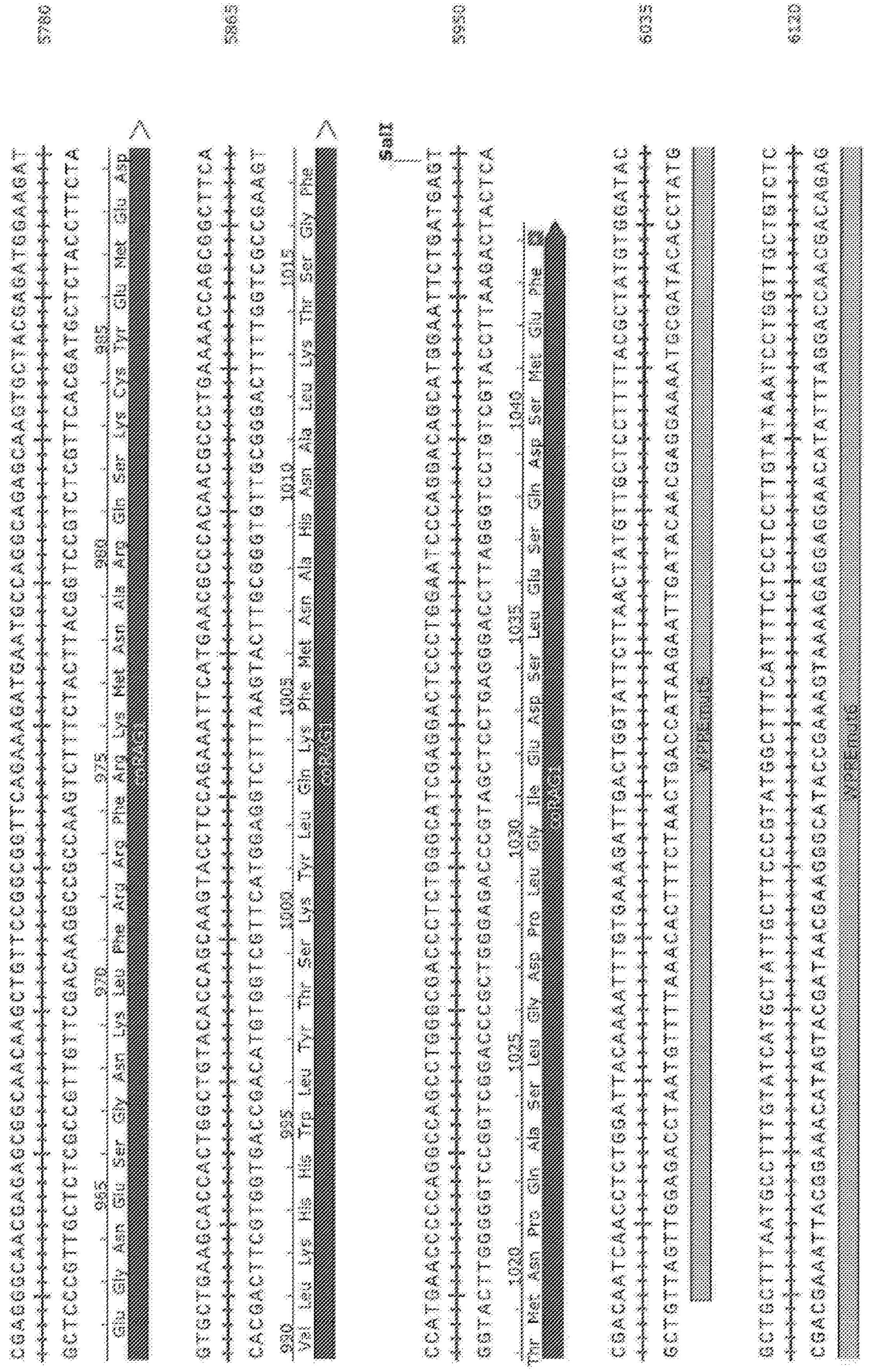
Figure 9:
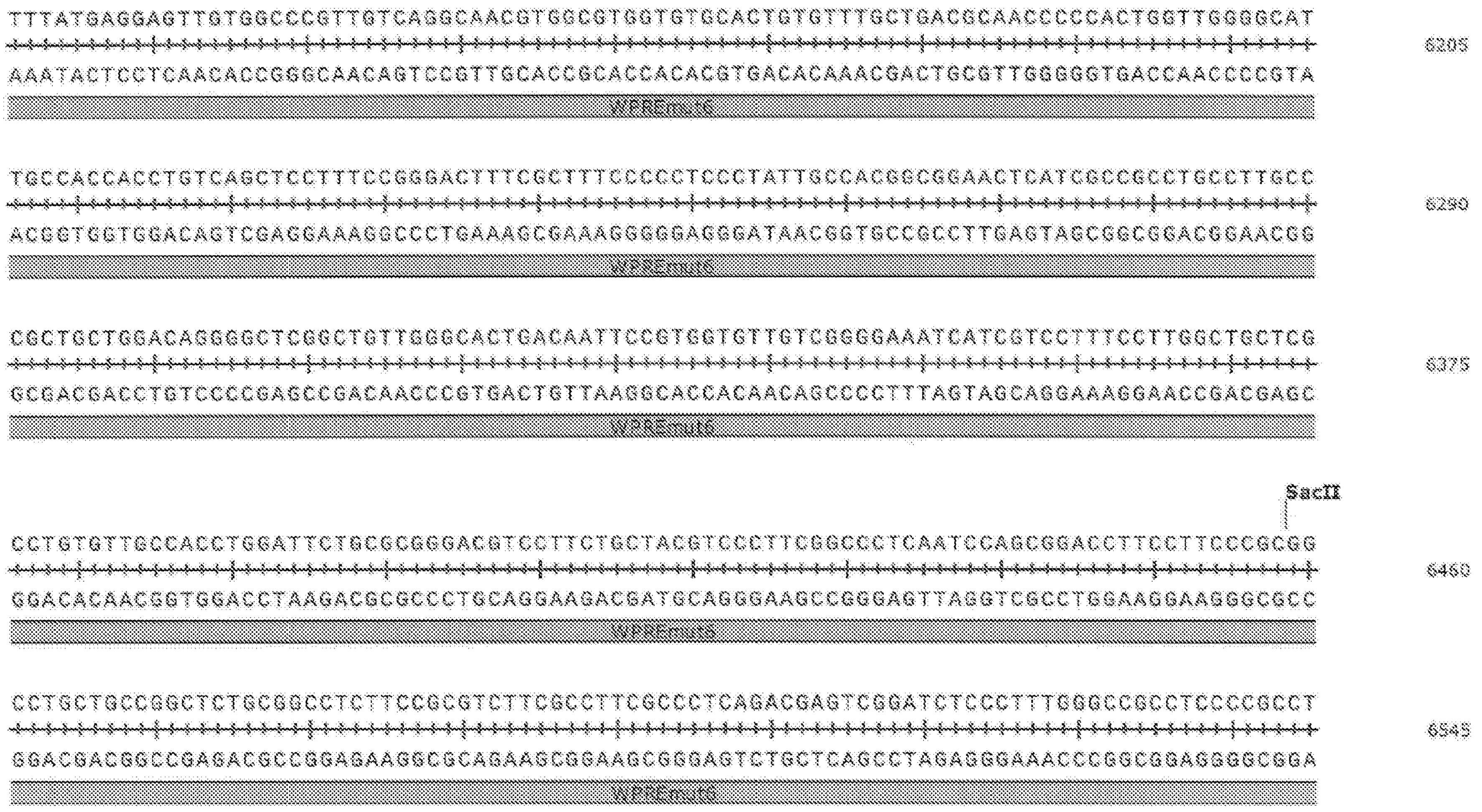
Figure 9:
Figure 9:
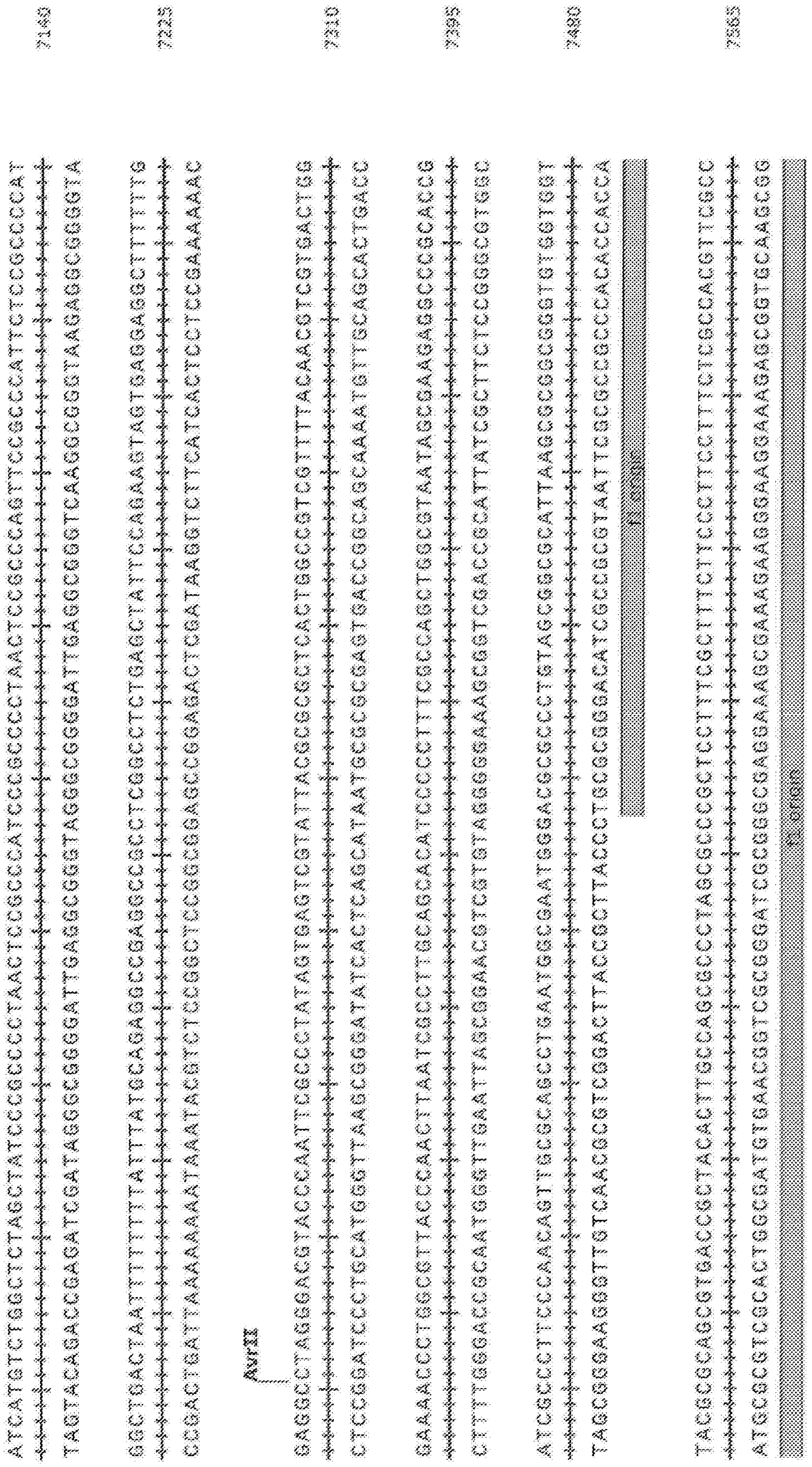
Figure 9:
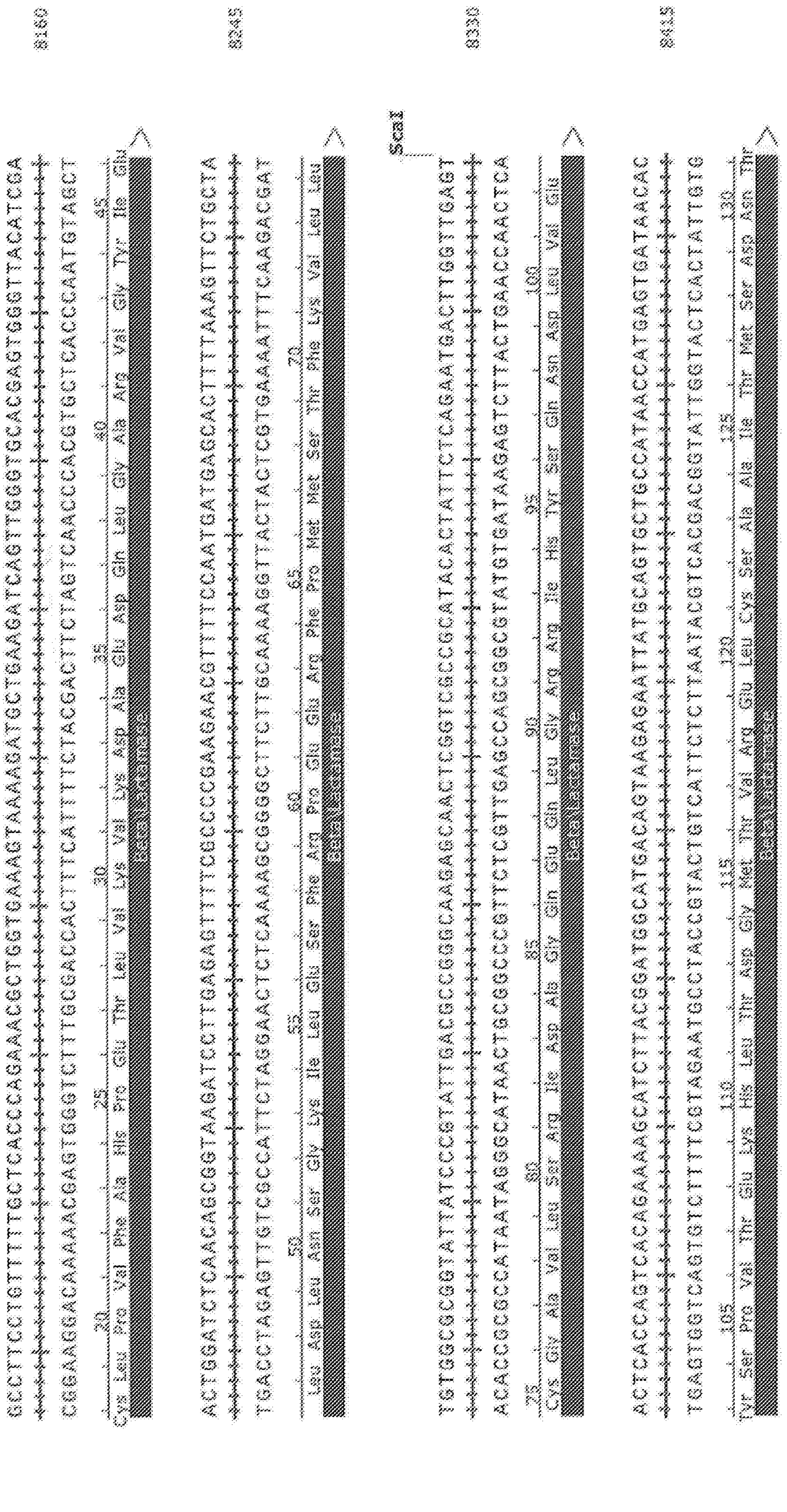
Figure 9:
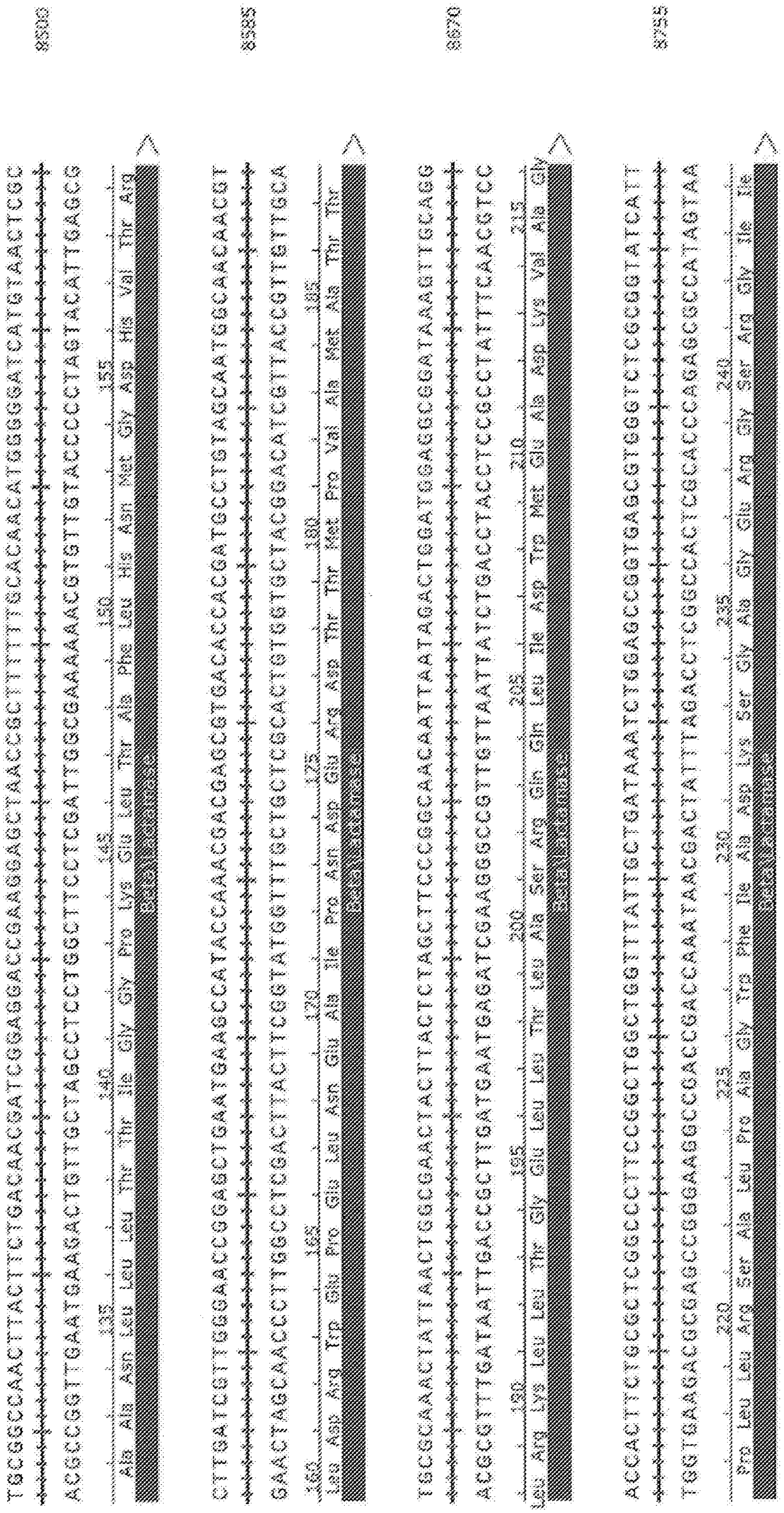
Figure 9:
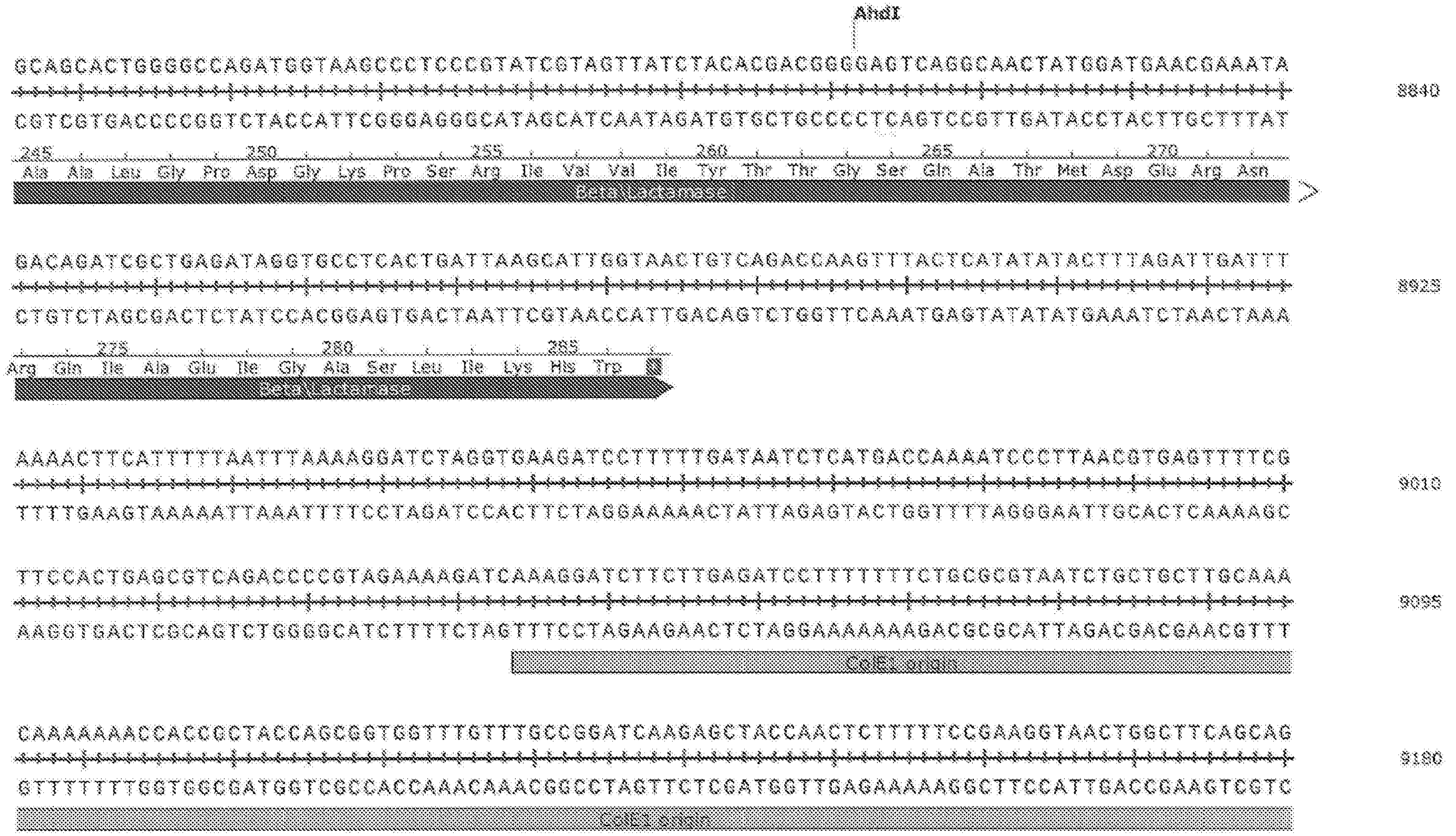

FIG. 9 shows the full plasmid sequence of the LV-MND-coRAG1.

Figure 10:
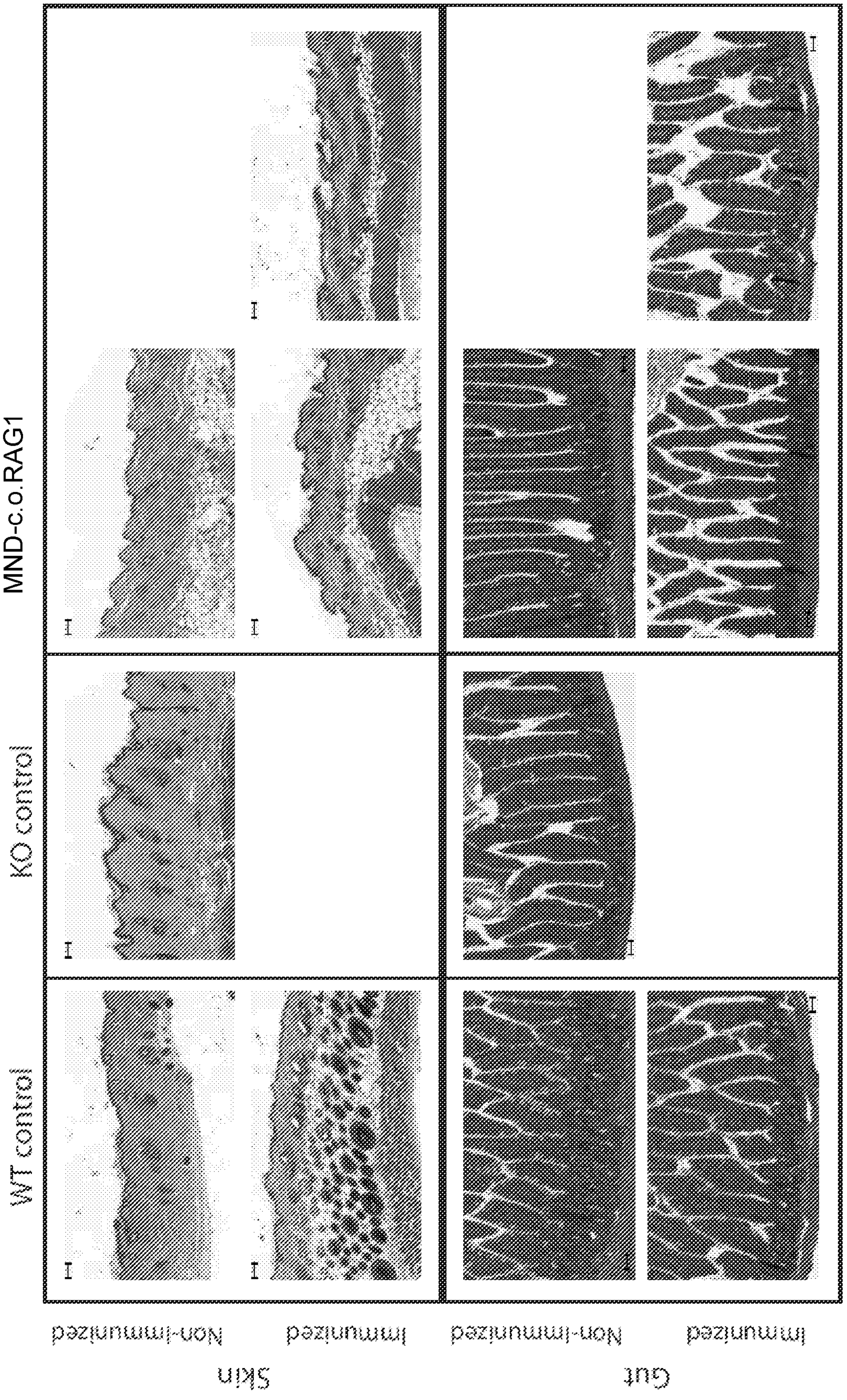

FIG. 10 shows histological analysis of the skin and gut after MND-c.o.RAG1 gene therapy in Rag1−/− mouse model.

Representative images were taken from WT Control, KO Control and MND-c.o.RAG1 mice (non-immunized and immunized). For skin the scale bar=100 μm and for gut the scale bar=50 μm). Samples were stained with hematoxylin and eosin.

DETAILED DESCRIPTION

The inventors have designed clinically relevant lentiviral SIN plasmids with different internal promoters operably linked to a codon optimised RAG1 transgene to identify the minimal threshold of RAG1 expression needed to obtain a therapeutic effect in vivo.

Using Rag1−/− mice as a preclinical model for RAG1-SCID to assess the efficacy of the various low copy number plasmids with a codon optimised RAG1 transgene, the inventors observed that B and T cell reconstitution directly correlated with RAG1 expression. Mice with low RAG1 expression showed poor immune reconstitution, whereas high RAG1 expression resulted in phenotypic and functional lymphocyte reconstitution comparable to mice receiving wild type stem cells. Surprisingly, RAG1-SCID patient $CD34^+$ cells transduced with a clinical RAG1 plasmid and transplanted into NSG mice fully restored human B and T cell development.

To facilitate the understanding of this invention, a number of terms are defined below.

Expression Cassette

An expression cassette is provided, comprising a codon optimised RAG1 transgene operably linked to a promoter. The RAG1 transgene may encode an amino acid sequence shown in SEQ ID NO:1 (human RAG 1), homologues thereof or functional variants thereof (e.g. conservative amino acid sequence variants thereof).

The term "expression cassette" refers to nucleic acid molecules that include one or more transcriptional control elements (such as, but not limited to promoters, enhancers and/or regulatory elements, polyadenylation sequences, and introns) that direct expression of a transgene in one or more desired cell types, tissues or organs. Expression cassettes of the present invention are synthetic nucleic acid molecules.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA RNA hybrid molecules, specifically including hnRNA, pre-mRNA, mRNA, cDNA, genomic DNA, amplification products, oligonucleotides, and synthetic (e.g., chemically synthesised) DNA, RNA or DNA RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

The expression cassette may comprise DNA or RNA.

The term "synthetic nucleic acid" as used herein relates to a nucleic acid molecule that does not occur in nature.

As used herein, the term "transgene" refers to an exogenous nucleic acid sequence i.e. a sequence that does not naturally occur with the other elements (e.g. the transcriptional control elements such as promoters etc) found within the expression cassette. In one example, a transgene is a gene encoding an industrially or pharmaceutically useful compound, or a gene encoding a desirable trait. In the context of the invention, the transgene of interest is a RAG1 transgene.

RAG1 Transgenes: Human RAG1 and Homologues Thereof

An expression cassette is therefore provided, comprising a codon optimised RAG1 transgene operably linked to a promoter.

A RAG1 transgene is a nucleic acid sequence that encodes a RAG1 protein. For the avoidance of doubt, the transgene does not necessarily include all of the natural elements of an endogenous RAG1; for example, the transgene may be the corresponding cDNA of the RAG1 (i.e. without the endogenous introns etc).

As used herein, the term "recombinase-activating gene-1 (RAG1)" refers to a protein encoded by the RAG1 gene.

Collectively, RAG1 and RAG2 form a RAG complex. A RAG complex is a multiprotein complex that mediates the DNA cleavage phase during VDJ recombination. This complex can make double-strand breaks by cleaving DNA at conserved recombination signal sequences (RSS). The RAG complex recognizes the RSS that flanks the V, D and J regions in the gene that codes for the constant region of both the heavy chain and light chain in an antibody. The complex binds to the RSS and nicks the DNA. This leads to the removal of the RSS and the eventual binding of the V, D and J sequences.

RAG1 is thought to possess most of the catalytic activity of the RAG complex. The RAG1 protein is the component that binds to and cleaves DNA, in this way RAG1 is involved in activation of immunoglobulin VDJ recombination. Whilst RAG2 does not appear to possess any endonuclease activity or DNA binding capability, it plays a role as an accessory factor. Its primary function is to interact with RAG1 and activate its endonuclease function.

Defects in the genes encoding RAG1 and RAG2 cause several diseases. In line with this, RAG1 and RAG2 deletion in mouse models impair T cell and B cell maturation, and functionally delete mature T and B cells from the immune system.

In one example, the RAG1 transgene comprises a nucleotide sequence encoding a human RAG1 protein (SEQ ID NO:1). Alternatively, the RAG1 sequence may be from a different species e.g. pig, mouse, rat, non-human primate etc.

Human RAG1 gene and protein sequences are known (see for example unique identifiers: HGNC:HGNC:9831 HUGO Human Gene Nomenclature Committee related to Ensembl: ENSG00000166349 MIM:179615). For ease of reference, a human RAG1 protein sequence is provided in SEQ ID NO:1.

Mouse RAG1 gene and protein sequences are known (see for example unique identifiers for mouse RAG1 include: ENSM UST00000078494; ENSMUSP00000077584; ENSMUSG00000061311).

Rat RAG1 gene and protein sequences are known (see for example unique identifiers: Ensembl: ENSRNOG00000004630; ENSRNOT00000006115; ENSRNOP00000006115; ENSRNOG00000004630).

RAG1 Proteins: Functional Variants

The RAG1 transgene may comprise a nucleotide sequence encoding a natural human, mouse or rat etc RAG1 protein, or a functional variant thereof (e.g. a human, mouse or rat RAG1 functional variant). An example of a functional variant RAG1 protein is a conservative amino acid substitution variant of a natural RAG1 (i.e. a sequence that varies from the natural sequence of human, mouse or rat RAG1 sequence by one or more conservative amino acid substitutions only).

A "functional variant" retains the functional capacity of the RAG1 protein. In other words, A functional RAG1 variant will be capable of making double stranded breaks by cleaving DNA at conserved recombination signal sequences (RSS). A person of skill in the art is readily aware of how to identify polypeptides having this activity using routine experiments known in the art. A suitable experiment for identifying functional RAG1 polypeptides is summarised below.

Functional RAG1 protein sequences can be identified using a functional complementation test. The test may use a lentivirus as described in the examples section below with a RAG1 transgene that encodes the RAG1 variant to be tested. Lin− bone marrow cells are used as source of hematopoietic stem cells and transduced with the recombinant lentivirus encoding the RAG1 sequence to be tested. These cells are subsequently transplanted into conditioned $Rag1^{-/-}$ mice and followed for the development of T cells. A sequence is deemed successful if development of $CD3^{+}TCR\alpha\beta^{+}$ T cells occurs after 8-12 weeks with numbers of T cells at least 50% of wild type stem cells.

A summary of a suitable test for RAG1 activity that has been performed by the inventors that may routinely be followed by a person of skill in the art is as follows: Murine bone marrow (BM) cells were obtained from femurs and tibias of C57BL/6 wild-type and C57BL/6 $Rag1^{-/-}$ mice. The obtained bones were flushed or crushed, cells were passed through a 0.7 μm cell strainer (Falcon), washed and viably frozen. After thawing, lineage negative cells were isolated using mouse lineage depletion kit and AUTOMacs cell sorter (Miltenyi Biotech). Lineage negative cells were stimulated overnight in StemSpam-SFEM containing Penicilin/Steptamycin (5,000 units/5,000 ug/ml; Gibco) and supplemented with 50 ng/mL recombinant mouse FMS-related tyrosine kinase 3 ligand (rmFLT3L; R&D systems), 100 ng/mL recombinant mouse Stem-Cell Factor (rmSCF; R&D systems) and 10 ng/mL recombinant mouse thrombopoietin (rmTPO; R&D systems). $Rag1^{-/-}$ cells were subsequently transduced with the different lentiviruses using 4 ug/ml proteamine sulphate (Sigma-Aldrich) and by way of spin-occulation at 800×g and 32° C. for 1 hour. Cells were cultured at 37° C., 5% $CO_2$ for 24 h in medium supplemented with cytokines.

Control mock-transduced cells (C57BL/6 wild-type cells referred as WT control and $Rag1^{-/-}$ cells referred as KO control) and transduced $Rag1^{-/-}$ murine cells (up to $5 \cdot 10^5$ cells/mouse) were mixed with supportive $Rag1^{-/-}$ spleen cells ($3 \cdot 10^6$ cells/mouse) in Iscove's Modified Dulbecco's Medium (IMDM) without phenol red (Gibco) and transplanted by tail vein injection into pre-conditioned $Rag1^{-/-}$ recipient mice. Recipient mice (8-12 week old mice) were conditioned with a total body single dose irradiation 24 h prior the transplantation using orthovoltage X-rays (8.08 Gy) or with two consecutive doses of 25 mg/kg Busulfan (Sigma-Aldrich) (48 h and 24 h prior transplantation).

Single cell suspensions from spleen were prepared by squeezing the organs through a 70 μM cell strainer (BD Falcon) and single cell suspension from BM was made as described previously. Erythrocytes from spleen were lysed using $NH_4Cl$ (8.4 g/L)/$KHCO_3$ (1 g/L) solution. Single cell suspensions were counted and stained with the antibodies listed in Table 1. Briefly, cells were incubated for 30 min at 4° C. in the dark with the antibody-mix solution including directly conjugated antibodies at the optimal working solution in FACS buffer (PBS pH7.4, 0.1% azide, 0.2% BSA). After washing with FACS buffer, a second 30 min incubation step at 4° C. was performed with the streptavidin-conjugated antibody solution. Cells were measured on FACS-CantoII and LSR Fortessa X-20 (BD Biosciences) and the data was analysed using FlowJO software (Tree Star).

Antibodies used in an optimal panel are listed below. At a minimum, CD3, CD4, CD8, TCRβ are included in the staining.

TABLE 1

Antibodies used in an optimal panel.

| Anti-mouse Antibody | Fluorochrome | Clone | Company | Identifier: Catalog number | Identifier: RRID |
|---|---|---|---|---|---|
| CD3e | Biotin | 145-2011 | BD Bioscience | 553060 | AB_394593 |
| CD4 | PE-Cy7 | RM4-5 | eBioscience | 25-0042-82 | AB_ 469578 |
| CD8a | PerCP | 53-6.7 | BioLegend | 100732 | AB_893423 |
| CD11b | Biotin | M1/70 | Biolegend | 101204 | AB_312787 |
| CD19 | APC | 1D3 | BD Bioscience | 550992 | AB_398483 |
| CD23 | Pe-Cy7 | B3B4 | eBioscience | 25-0232-81 | AB_469603 |
| CD43 | Biotin | S7 | BD Bioscience | 553269 | AB_2255226 |
| CD43 | PE | S7 | BD Bioscience | 553271 | AB_394748 |
| CD44 | APC-Cy7 | IM7 | BD Bioscience | 560568 | AB_1727481 |
| CD45 | FITC | 30-F11 | BD Bioscience | 553079 | AB_394609 |
| CD45R/B220 | PerCP | RA3-6B2 | Biolegend | 103233 | AB_893355 |
| CD45R/B220 | Pe-Cy7 | RA3-6B2 | eBioscience | 25-0452 | AB_2341160 |
| CD62L | APC | MEL-14 | Biolegend | 104411 | AB_313098 |
| CD93 | APC | AA4.1 | eBioscience | 17-5892 | AB_469466 |
| CD138 | PE | 281-2 | BD Bioscience | 553714 | AB_395000 |
| IgD | ef450 | 11-26c | eBioscience | 48-5993-80 | AB_1272239 |
| IgM | FITC | II/41 | BD Bioscience | 553437 | AB_394857 |
| TCRβ | FITC | H57-597 | BD Bioscience | 553171 | AB_394683 |
| TCRγδ | PE | GL3 | BD Bioscience | 553178 | AB_394689 |
| Streptavidin | APC-Cy7 | — | BD Bioscience | 554063 | AB_10054651 |
| Streptavidin | ef450 | — | eBioscience | 48-4317-82 | AB_10359737 |

Mice used for transplantation were kept in a specified pathogen-free section. The first four weeks after transplantation mice were fed with additional DietGel recovery food (Clear H2O) and antibiotic water containing 0.07 mg/mL Polymixin B (Bupha Uitgeest), 0.0875 mg/mL Ciprofloxacin (Bayer b.v.) and 0.1 mg/mL Amfotericine B (Bristol-Myers Squibb) and their welfare was monitored daily. Peripheral blood (PB) from the mice was drawn by tail vein incision every 4 weeks until the end of the experiment. PB, thymus, spleen and BM were obtained from $CO_2$ euthanized mice.

Accordingly, a RAG1 polypeptide may comprise the amino acid sequence shown in SEQ ID NO: 1 (or the equivalent mouse or rat RAG1 sequence), or may be a functional variant (or functional fragments) thereof. Such variants may be naturally occurring (e.g. allelic), synthetic, or synthetically improved functional variants of SEQ ID NO:1 (or the equivalent mouse or rat RAG1 sequence).

Functional variants will typically contain only conservative substitutions of one or more amino acids of SEQ ID NO:1 (or the equivalent mouse or rat RAG1 sequence), or a substitution, deletion or insertion of non-critical amino acids in non-critical regions of the protein. A functional variant of SEQ ID NO:1 (or the equivalent mouse or rat RAG1 sequence) may therefore be a conservative amino acid sequence variant of SEQ ID NO:1 (or the equivalent mouse or rat RAG1 sequence).

Non-functional variants are amino acid sequence variants of SEQ ID NO: 1 (or the equivalent mouse or rat RAG1 sequence) that do not have RAG1 activity. Non-functional variants will typically contain a non-conservative substitution, a deletion, or insertion or premature truncation of the amino acid sequence of SEQ ID NO:1 (or the equivalent mouse or rat RAG1 sequence) or a substitution, insertion or deletion in critical amino acids or critical regions. Methods for identifying functional and non-functional variants (e.g. functional and non-functional allelic variants) are well known to a person of ordinary skill in the art.

A summary of the critical and non-critical amino acids in RAG1 is provided in Luigi D. Notarangelo, Min-Sung Kim, Jolan E. Walter & Yu Nee Lee Nature Reviews Immunology volume 16, pages 234-246 (2016). Accordingly, a person of skill in the art would readily be able to identify amino acids that may be substituted to provide functional variants (or functional fragments), such as conservative amino acid sequence variants, of SEQ ID NO:1 (or the equivalent mouse or rat RAG1 sequence).

A functional variant may comprise an amino acid sequence having at least about 60%, 65%, 70%, 75%, 80%, 85%, 90%, 91%, 92%, 93%, 94%, 95%, 96%, 97%, 98%, 99% or 100% identity to the amino acid sequence of SEQ ID NO:1 ((or the equivalent mouse or rat RAG1 sequence), or portions or fragments thereof. Suitably, percent identity can be calculated as the percentage of identity to the entire length of the reference sequence (e.g. SEQ ID NO:1), or portions or fragments thereof.

In one example, the RAG1 transgene encodes a polypeptide comprising the sequence of SEQ ID NO: 1, or a conservative amino acid sequence variant thereof.

As used herein, a "naturally-occurring" polypeptide refers to an amino acid sequence that occurs in nature.

A "non-essential" (or "non-critical") amino acid residue is a residue that can be altered from the wild-type sequence of (e.g. the sequence of SEQ ID NO:1) without abolishing or, more preferably, without substantially altering a biological activity, whereas an "essential" (or "critical") amino acid residue results in such a change. For example, amino acid residues that are conserved are predicted to be particularly non-amenable to alteration, except that amino acid residues within the hydrophobic core of domains can generally be replaced by other residues having approximately equivalent hydrophobicity without significantly altering activity.

A "conservative amino acid substitution" is one in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential (or non-critical) amino acid residue in a protein is preferably replaced with another amino acid residue from the same side chain family. Alternatively, in another embodiment, mutations can be introduced randomly, and the resultant mutants can be screened for biological activity to identify mutants that retain activity.

A conservative amino acid substitution variant of RAG1 may have at least one (e.g. two or fewer, three or fewer, four or fewer, five or fewer, six or fewer, seven or fewer, eight or fewer, nine or fewer, ten or fewer etc) conservative amino acid substitutions compared to a natural human, mouse or rat RAG1 (as identified above using unique identifiers).

RAG1 Transgene Sequence; Variation at the Nucleic Acid Sequence Level

A "RAG1 transgene" refers to any nucleic acid sequence that encodes a functional RAG1 protein (e.g. a human, mouse or rat RAG1, or functional variants such as amino acid substitution variants thereof).

The RAG1 nucleotide sequence described herein is codon optimised. As used herein "codon-optimised" (or "c.o.") refers to polynucleotide sequences encoding the RAG1 protein that are modified relative to the native polynucleotide sequence whilst not altering the encoding amino acid sequence. This term is widely known in the art. Codon optimisation of a polynucleotide sequence can lead to several effects that increase overall translational efficiency/expression levels of the RAG1 protein in a cell.

For example:

1. Effect on RNA Secondary Structure

Because the secondary structure of the 5' end of mRNA influences translational efficiency, synonymous changes at this region on the mRNA can result in profound effects on gene expression. Codon usage in noncoding DNA regions can therefore play a major role in RNA secondary structure and downstream protein expression, which can undergo further selective pressures. In particular, strong secondary structure at the ribosome-binding site or initiation codon can inhibit translation, and mRNA folding at the 5' end generates a large amount of variation in protein levels.

In this context, the RAG1 nucleotide sequence may be codon optimised to include higher GC content of the coding sequence.

2. Effect on Transcription/Gene Expression

Heterologous gene expression is used in many biotechnological applications, including protein production and metabolic engineering. Because tRNA pools vary between different organisms, the rate of transcription and translation of a particular coding sequence can be less efficient when placed in a non-native context. For an overexpressed transgene, the corresponding mRNA makes a large percent of total cellular RNA, and the presence of rare codons along the transcript can lead to inefficient use and depletion of ribosomes and ultimately reduce levels of heterologous protein production. However, using codons that are optimized for tRNA pools in a particular host to overexpress a heterologous gene may also cause amino acid starvation and alter the equilibrium of tRNA pools. This method of adjusting codons to match host tRNA abundances, has traditionally been used for expression of a heterologous gene. However, new strategies for optimization of heterologous expression consider global nucleotide content such as local mRNA folding, codon pair bias, a codon ramp or codon correlations.

Specialized codon bias is further seen in some endogenous genes such as those involved in amino acid starvation. For example, amino acid biosynthetic enzymes preferentially use codons that are poorly adapted to normal tRNA abundances but have codons that are adapted to tRNA pools under starvation conditions. Thus, codon usage can introduce an additional level of transcriptional regulation for appropriate gene expression under specific cellular conditions.

In this context, the RAG1 nucleotide sequence may be codon optimised to include removal of alternative splice sites and cryptic splice sites, optimized codon usage for human tRNA.

3. Effect on Speed of Translation Elongation

Generally speaking for highly expressed genes, translation elongation rates are faster along transcripts with higher codon adaptation to tRNA pools, and slower along transcripts with rare codons. This correlation between codon translation rates and cognate tRNA concentrations provides additional modulation of translation elongation rates, which can provide several advantages to the organism. Specifically, codon usage can allow for global regulation of these rates, and rare codons may contribute to the accuracy of translation at the expense of speed.

In this context, the RAG1 nucleotide sequence may be codon optimised to include optimized codon usage for human tRNA.

4. Effect on Protein Folding

Protein folding in vivo is vectorial, such that the N-terminus of a protein exits the translating ribosome and becomes solvent-exposed before its more C-terminal regions. As a result, co-translational protein folding introduces several spatial and temporal constraints on the nascent polypeptide chain in its folding trajectory. Because mRNA translation rates are coupled to protein folding, and codon adaption is linked to translation elongation, it has been hypothesized that manipulation at the sequence level may be an effective strategy to regulate or improve protein folding. Several studies have shown that pausing of translation as a result of local mRNA structure occurs for certain proteins, which may be necessary for proper folding. Furthermore, synonymous mutations have been shown to have significant consequences in the folding process of the nascent protein and can even change substrate specificity of enzymes. These studies suggest that codon usage influences the speed at which polypeptides emerge vectorially from the ribosome, which may further impact protein folding pathways throughout the available structural space.

Any codon-optimised RAG1 polynucleotide sequence, regardless of the means of codon optimisation, is encompassed herein.

Analysis of the human RAG1 cDNA sequence by the inventors revealed several possibilities to improve the DNA sequence without affecting the amino acid sequence, as many rare codons are present in the native RAG1 gene. Most of these codons were replaced by more frequently used codons of *Homo sapiens* genes. GC content was also increased to augment mRNA stability. Finally, 21 cis-acting motifs (prokaryotic inhibitory motifs, splice donor sites, polyA sites and RNA instability motifs) that could negatively influence expression were removed. No alterations were made to the amino acid sequence, allowing regulatory mechanisms that occur at the protein level to function normally.

In one non-limiting example, a RAG1 codon optimised transgene may encode an amino acid sequence of SEQ ID NO: 1 and comprise the nucleic acid sequence of SEQ ID NO: 2. In other words, the RAG1 transgene may encode a human RAG1 protein (SEQ ID NO:1), whilst having a nucleic acid sequence that differs from a native RAG1 nucleic acid sequence (SEQ ID NO:3) due to (as a minimum) codon optimisation of the RAG1 catalytic domain. The nucleic acid sequence shown in SEQ ID NO:2 is a core catalytic domain sequence of human RAG1 that shows which nucleic acids were changed during codon optimisation. The inventors have shown that codon optimisation of RAG1 is beneficial for optimal expression of the RAG1 transgene. Advantageously, the codon optimised sequence provided herein for the RAG1 catalytic domain (SEQ ID NO:2) does not adversely affect RAG1 catalytic domain function, which is crucial for RAG1 activity. It therefore provides a good base sequence for codon optimised variants of the RAG1 transgene. Accordingly, codon optimised variants of the RAG1 transgene may include the codon optimised catalytic domain shown in SEQ ID NO:2, with optional additional codon optimisation in the other regions of the RAG1 transgene.

For the avoidance of doubt, the RAG1 nucleic acid sequence may therefore vary from the native RAG1 sequence of SEQ ID NO:3 in at least the catalytic domain (with optional codon optimisation in other areas of the RAG1 transgene sequence), while still encoding a functional RAG1 polypeptide such as that shown in SEQ ID NO:1.

The sequence of a codon optimised human RAG1 transgene that has successfully been used by the inventors is shown in SEQ ID NO:4. Accordingly, in one example, an expression cassette is provided comprising the RAG1 transgene of SEQ ID NO:4 operably linked to a promoter. Suitable promoters are discussed below.

As described herein, the RAG1 transgene is operably linked to a promoter within the expression cassette. The terms "operably linked", "operably connected" or equivalent expressions as used herein refer to the arrangement of various nucleic acid elements relative to each such that the elements are functionally connected and are able to interact with each other in the manner intended. Such elements may include, without limitation, a promoter, an enhancer and/or a regulatory element, a polyadenylation sequence, one or more introns and/or exons, and a coding sequence of a gene of interest to be expressed. The nucleic acid sequence elements, when properly oriented or operably linked, act together to modulate the activity of one another, and ultimately may affect the level of expression of an expression product. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides (i.e. spacer sequences), or base pairs, between the elements. As understood by the skilled person, operably linked implies functional activity, and is not necessarily related to a natural positional link.

A "spacer sequence" or "spacer" as used herein is a nucleic acid sequence that separates two functional nucleic acid sequences. It can have essentially any sequence, provided it does not prevent the functional nucleic acid sequence from functioning as desired. Typically, it is non-functional, as in it is present only to space adjacent functional nucleic acid sequences from one another.

As used herein, the term "promoter" refers to a nucleic acid sequence that is generally located upstream of a nucleic acid sequence to be transcribed. The promoter is typically needed for transcription to occur, i.e. it initiates transcription. Promoters permit the proper activation or repression of transcription of a coding sequence under their control. A promoter typically contains specific sequences that are recognized and bound by plurality of transcription factors (TFs). TFs bind to the promoter sequences and result in the recruitment of RNA polymerase, an enzyme that synthesizes RNA from the coding region of the gene. A great many promoters are known in the art.

The promoters described herein may be described as "strong promoters" as they drive a high level of expression of the operably linked transgene in a cell. Typically, the promoter drives expression of the operably linked RAG1 transgene in a cell such that the expression product of the RAG1 transgene in the cell is at a level that is at least x-fold higher than the corresponding expression product of a housekeeping gene (e.g. ABL1) in the cell (e.g. a recombinant human CD34+ haematopoietic stem cell). In this context, "x-fold higher" includes at least 2-fold, at least 3-fold, at least 4-fold, at least 5-fold, at least 6-fold, at least 7-fold, at least 8-fold, at least 9-fold, and at least 10-fold higher than the corresponding expression product of a housekeeping gene (e.g. ABL1) in the cell (e.g. a recombinant human CD34+ haematopoietic stem cell). As will be clear to a person of skill in the art, "expression product" covers all products that are generated during expression of the transgene, and therefore covers the mRNA (transcript) of the transgene, as well as the protein. Methods for measuring the level of expression product in a cell are well known in the field. For example, the expression product of a transgene may be measured at the transcript (mRNA) or protein level.

Any known mRNA detection method may be used to detect the level of mRNA in a sample. For example, the level of a specific mRNA in a sample using Southern or Northern blot analysis, polymerase chain reaction or probe arrays. In one embodiment a sample may be contacted with a nucleic acid molecule (i.e. a probe, such as a labeled probe) that can specifically hybridize to the specific mRNA.

Alternatively, the level of a specific mRNA in a sample may be evaluated with nucleic acid amplification, for example by rtPCR, ligase chain reaction, self sustained sequence replication, transcriptional amplification or any other nucleic acid amplification method, followed by the detection of the amplified molecules using techniques known in the art.

Any known protein detection method may be used to detect the level of protein in a sample. Generally, protein detection methods comprise contacting an agent or antibody that selectively binds to a protein with a sample to determine the level of the specific protein in the sample. Preferably, the agent or antibody is labeled, for example with a detectable label. Suitable antibodies may be polyclonal or monoclonal. An antibody fragment such as a Fab or F(ab')2 may be used. As used herein the term "labeled", refers to direct labeling of the probe or antibody by coupling (i.e., physically linking) a detectable substance to the probe or antibody, as well as indirect labeling of the probe or antibody by reactivity with a detectable substance.

The level of a specific protein biomarker in a sample may be determined by techniques known in the art, such as enzyme linked immunosorbent assays (ELISAs), immunoprecipitation, immunofluorescence, enzyme immunoassay (EIA), radioimmunoassay (RIA), Western blot analysis, and Lateral Flow Devices (LFDs) utilizing a membrane bound antibody specific to the protein biomarker. Alternatively, the level of a specific biomarker protein in a sample can be detected and quantified using mass spectrometry. Such methods are routine in the art.

Levels of the expression product may be normalized by comparison to the level of a housekeeping gene in the sample e.g. an mRNA or protein that is constitutively expressed. A suitable housekeeping gene is ABL1, however others may also be used. This normalization allows the comparison of the expression level in one sample to another sample, or between samples from different sources.

Advantageously, the promoters described herein drive the requisite level of expression of the transgene (i.e. at least 2-fold, at least 3-fold, at least 4-fold, at least 5-fold, at least 6-fold, at least 7-fold, at least 8-fold, at least 9-fold, or at least 10-fold higher than the corresponding expression product of a housekeeping gene (e.g. ABL1) in the cell (e.g. a recombinant human $CD34^+$ haematopoietic stem cell) when there are 5 or fewer copies of the expression cassette integrated into the genome of the cell.

In other words, the promoters described herein can drive the requisite level of expression of the RAG1 transgene even when the promoter is within a plasmid that is low copy number plasmid. The term low copy number plasmid is well known in the art (and is used to describe vectors that integrate into the genome at a frequency of 5 or fewer copies per cell (i.e. 5 or fewer, 4 or fewer, 3 or fewer, 2 or fewer, 1 or fewer copies, 0.5 or fewer, 0.4 or fewer, 0.3 or fewer, 0.2 or fewer etc per cell)). See for example:

1. Poletti V, Charrier S, Corre G, Gjata B, Vignaud A, Zhang F, Rothe M, Schambach A, Gaspar H B, Thrasher A J, Mavilio F. "Preclinical Development of a Lentiviral Vector for Gene Therapy of X-Linked Severe Combined Immunodeficiency." Mol Ther Methods Clin Dev. 2018 Mar. 10; 9:257-269. doi:10.1016/j.omtm.2018.03.002. eCollection 2018 Jun. 15. PubMed PMID: 29707600; PubMed Central PMCID: PMC5918176.

2. Siler U, Paruzynski A, Holtgreve-Grez H, Kuzmenko E, Koehl U, Renner E D, Alhan C, de Loosdrecht A A, Schwable J, Pfluger T, Tchinda J, Schmugge M, Jauch A, Naundorf S, Kühlcke K, Notheis G, Gungor T, Kalle C V, Schmidt M, Grez M, Seger R, Reichenbach J. "Successful Combination of Sequential Gene Therapy and Rescue Allo-HSCT in Two Children with X-CGD—Importance of Timing." Curr Gene Ther. 2015; 15(4):416-27. PubMed PMID: 25981636.

3. Greene M R, Lockey T, Mehta P K, Kim Y S, Eldridge P W, Gray J T, Sorrentino B P. "Transduction of human $CD34^+$ repopulating cells with a self-inactivating lentiviral vector for SCID-X1 produced at clinical scale by a stable cell line." Hum Gene Ther Methods. 2012 October; 23(5): 297-308. doi: 10.1089/hgtb.2012.150. Epub 2012 Nov. 7. PubMed PMID: 23075105; PubMed Central PMCID: PMC373213

Suitable promoters may readily be identified by a person of skill in the art using routine methods. For example, potential promoters of interest may be operably linked to the codon optimised RAG1 nucleic acid sequence provided herein (SEQ ID NO: 4), within the plasmid backbone provided herein (pCCL) and the resultant plasmid may be introduced into the Rag1−/− mice preclinical model for RAG-SCID described herein. The level of RAG1 expression product can then be measured as described in the examples section below and compared to ABL1 levels as described herein. If the RAG1 expression level is at least three-fold (e.g. ten-fold) higher than the ABL1 level, the promoter being tested is considered as suitable for the invention and thus falls within the scope of the invention that is claimed. A detailed explanation of the methodology that can be used to test potential promoters of interest is found in the examples section below. Alternative/supplementary methods are also known to a person of skill in the art.

The strength of the promoter can be tested most readily by testing for expression of the therapeutic RAG1 gene by Q-PCR in $CD34^+$ cells. As a reference, a house keeping gene such as ABL1 is used in the same assay. The ratio between the two expression levels is a direct measure of promoter strength.

Q-PCR was used for the quantitative analysis mRNA expression using WPRE, c.o.RAG1, ABL1 as targets. Total RNA from single cell suspensions was purified using RNeasy Mini kit (Qiagen) and reverse transcribed into cDNA using Superscript III kit (Invitrogen). Genomic DNA was extracted from single cell suspensions using the GeneElute Mammalian Genomic DNA kit (Sigma-Aldrich). Dneasy Blood and Tissue Kit (Qiagen) was used to isolate genomic DNA from murine organs and tissues. The levels of transgene expression were determined on cDNA samples, by normalizing c.o.RAG1 to the expression of the ABL1 gene. qPCR was performed using TaqMan Universal Master Mix II (Thermofisher) in combination with specific probes for indicated genes from Universal Probe Library (Roche). Primers and probes used are listed in Table 2. PCR reactions were performed on the StepOnePlus Real-Time PCR system (Thermofisher). All samples should be run in triplicate. Exemplary primers that could be used are:

In one example, an expression cassette is therefore provided comprising a RAG1 transgene operably linked to a MND promoter. In this example, when the promoter is MND, the RAG1 transgene may be a codon optimised version of a human RAG1 transgene (as shown in SEQ ID NO:2 or SEQ ID NO:4, where the transgene encodes the protein of SEQ ID NO:1 but does not have the native RAG1 nucleic acid sequence of SEQ ID NO:3). Advantageously, the expression product of the RAG1 transgene (when operably linked to an MND promoter and when expressed in a cell (e.g. a recombinant human CD34+ haematopoietic stem cell), is at a level that is at least three-fold higher than a house keeping gene (such as ABL1) in the cell. This is particularly advantageous when the expression cassette is present in the cell at low copy numbers, such as when there are 5 or fewer copies of the expression cassette integrated into the genome of the cell (and the expression product of the RAG1 transgene (when operably linked to an MND promoter and when expressed in a cell (e.g. a recombinant human CD34+ haematopoietic stem cell)), is still at a level that is at least three-fold higher than a house keeping gene (such as ABL1) in the cell).

TABLE 2 primers

| Description | Orientation | DNA sequence 5'-3' |
|---|---|---|
| ABL1 | FW | 5'-TGGAGATAACACTCTAAGCATAACTAAAGGT-3' (SEQ ID NO: 6) |
| | RV | 5'-GATGTAGTTGCTTGGGACCCA-3' (SEQ ID NO: 7) |
| | Probe | 5'FAM-CCATTTTTGGTTTGGGCTTCACACCATT- TAMRA 3' (SEQ ID NO: 8) |
| c.o.Rag1 | FW | 5' CAACTGCAAGCACGTGTTCTG 3' (SEQ ID NO: 9) |
| | RV | 5' GCAGTAGCTGCCCATCACTTT 3' (SEQ ID NO: 10) |
| | Probe | 5'FAM AGAGTGTGCATCCTGCGGTGCCT TAMRA 3' (SEQ ID NO: 11) |

By way of example, suitable promoters include MND, CMV, RSV and CAG. These promoters are well known; see for example Daniela Zychlinski, Axel Schambach, Ute Modlich, Tobias Maetzig, Johann Meyer, Elke Grassman, Anjali Mishra, Christopher Baum, "Physiological Promoters Reduce the Genotoxic Risk of Integrating Gene Vectors", Molecular Therapy, Volume 16, Issue 4, 2008, Pages 718-725, ISSN 1525-0016, https://doi.org/10.1038/mt.2008.5; Astrakhan A, Sather B D, Ryu B Y, Khim S, Singh S, Humblet-Baron S, Ochs H D, Miao C H, Rawlings D J. "Ubiquitous high-level gene expression in hematopoietic lineages provides effective lentiviral gene therapy of murine Wiskott-Aldrich syndrome." Blood. 2012 May 10; 119(19): 4395-407. doi: 10.1182/blood-2011-03-340711 Yaguchi M, Ohashi Y, Tsubota T, Sato A, Koyano K W, Wang N, Miyashita Y. "Characterization of the properties of seven promoters in the motor cortex of rats and monkeys after lentiviral vector-mediated gene transfer." Hum Gene Ther Methods. 2013 December; 24(6):333-44. doi: 10.1089/hgtb.2012.238.

The MND promoter may be universally identified by the unique identifier: GenBank: LZ103461.1. Its sequence is also shown herein as SEQ ID NO: 5. Similarly, the CMV promoter may be universally identified by the unique identifier: GenBank: AB902850.1 (ncl 1114-1493); the RSV promoter may be universally identified by the unique identifier: GenBank: GM964660.1; and the CAG CMV early enhancer/chicken β-actin [CAG] promoter may be universally identified by the unique identifier: pubmed/11144964.

In another example, an expression cassette is provided comprising a RAG1 transgene operably linked to a CMV promoter. In this example, when the promoter is CMV, the RAG1 transgene may be a human RAG1 transgene, or a codon optimised version thereof (as shown in SEQ ID NO:2 or SEQ ID NO:4, where the transgene encodes the protein of SEQ ID NO:1 but does not have the native RAG1 nucleic acid sequence of SEQ ID NO:3). Advantageously, the expression product of the RAG1 transgene (when operably linked to an CMV promoter and when expressed in a cell (e.g. a recombinant human CD34+ haematopoietic stem cell), is at a level that is at least three-fold higher than a house keeping gene (such as ABL1) in the cell. This is particularly advantageous when the expression cassette is present in the cell at low copy numbers, such as when there are 5 or fewer copies of the expression cassette integrated into the genome of the cell (and the expression product of the RAG1 transgene (when operably linked to an CMV promoter and when expressed in a cell (e.g. a recombinant human CD34+ haematopoietic stem cell)), is still at a level that is at least three-fold higher than a house keeping gene (such as ABL1) in the cell).

An expression cassette is also provided comprising a RAG1 transgene operably linked to a RSV promoter. In this example, when the promoter is RSV, the RAG1 transgene may be a codon optimised version of a human RAG1 transgene (as shown in SEQ ID NO:2 or SEQ ID NO:4, where the transgene encodes the protein of SEQ ID NO:1 but does not have the native RAG1 nucleic acid sequence of SEQ ID NO:3). Advantageously, the expression product of the RAG1 transgene (when operably linked to an RSV promoter and when expressed in a cell (e.g. a recombinant human CD34+ haematopoietic stem cell), is at a level that is at least three-fold higher than a house keeping gene (such as ABL1) in the cell. This is particularly advantageous when the expression cassette is present in the cell at low copy numbers, such as when there are 5 or fewer copies of the expression cassette integrated into the genome of the cell (and the expression product of the RAG1 transgene (when operably linked to an RSV promoter and when expressed in a cell (e.g. a recombinant human CD34+ haematopoietic stem cell)), is still at a level that is at least three-fold higher than a house keeping gene (such as ABL1) in the cell).

An expression cassette is also provided comprising a RAG1 transgene operably linked to a CAG promoter. In this example, when the promoter is CAG, the RAG1 transgene may be a codon optimised version of a human RAG1 transgene (as shown in SEQ ID NO:2 or SEQ ID NO:4, where the transgene encodes the protein of SEQ ID NO:1 but does not have the native RAG1 nucleic acid sequence of SEQ ID NO:3). Advantageously, the expression product of the RAG1 transgene (when operably linked to an CAG promoter and when expressed in a cell (e.g. a recombinant human CD34+ haematopoietic stem cell), is at a level that is at least three-fold higher than a house keeping gene (such as ABL1) in the cell. This is particularly advantageous when the expression cassette is present in the cell at low copy numbers, such as when there are 5 or fewer copies of the expression cassette integrated into the genome of the cell (and the expression product of the RAG1 transgene (when operably linked to an CAG promoter and when expressed in a cell (e.g. a recombinant human CD34+ haematopoietic stem cell)), is still at a level that is at least three-fold higher than a house keeping gene (such as ABL1) in the cell).

As described herein, the expression product of the RAG1 transgene (when operably linked to a promoter and when expressed in a cell is advantageously at a level that is at least three-fold higher than a house keeping gene (such as ABL1) in the cell. This is particularly advantageous when the expression cassette is present in the cell at low copy numbers, such as when there are 5 or fewer copies of the expression cassette integrated into the genome of the cell (and the expression product of the RAG1 transgene (when operably linked to the promoter and when expressed in a cell, is still at a level that is at least three-fold higher than a house keeping gene (such as ABL1) in the cell). Throughout the description, the exemplary cell is given as a recombinant human CD34+ haematopoietic stem cell. However, any cell which has the expression cassette integrated into its genome is equally relevant, such as for example, a hematopoietic progenitor cell, including by way of non-limiting example, a HSC (e.g. a CD34+ HSC), white blood cell, patient specific induced pluripotent stem cell (iPSC), or a mesenchymal stem cell.

The Abelson murine leukemia viral oncogene homolog 1 (ABL1) gene is routinely used as a control gene to normalise or compare expression levels of the transgene between cells, samples or experiments. This is because gene transcript levels of ABL1 do not vary significantly between normal and leukemic samples (Beillard et al., 2003). ABL1 can therefore be used to normalise or compare expression levels obtained for a RAG1 transgene expression product (e.g. RAG1 transcript or protein levels in a cell). Methods for measuring ABL1 and comparing it to the expression product of interest are well known in the art, and are described elsewhere herein.

Additional elements may also be included in the expression cassette to optimise expression of the desired transgene.

For example, the expression cassette may contain any combination, or indeed all, of the following elements, the sequences of which are well known in the art;

TABLE 3 accessory elements for expression cassettes

| Element | Delivery relative to transgene | Purpose |
|---|---|---|
| cPPT | in cis | Central polypurine tract; recognition site for proviral DNA synthesis. Increases transduction efficiency and transgene expression. |
| Psi (Ψ) | in cis | RNA target site for packaging by Nucleocapsid. |
| RRE | in cis | Rev Response Element; sequence to which the Rev protein binds. |
| WPRE | in cis | Woodchuck hepatitis virus post-transcriptional regulatory element; sequence that stimulates the expression of transgenes via increased nuclear export. |
| LTR | in cis | LTR; Long terminal repeats; U3-R-U5 regions found on either side of a retroviral provirus (see below). Cloning capacity between the LTRs is ~8.5 kb, but inserts bigger than ~3 kb are packaged less efficiently. |
| Subcomponents: | | Subcomponents: |
| U3 | | U3; Unique 3'; region at the 3' end of viral genomic RNA (but found at both the 5' and 3' ends of the provirus). Contains sequences necessary for activation of viral genomic RNA transcription. |
| R | | R; Repeat region found within both the 5' and 3' LTRs of retro/lentiviral vectors. Tat binds to this region. |
| Sub-element: | | Sub-element: |
| TAR | | TAR; 2nd generation only; Trans-activating response element; located in the R region of the LTR and acts as a binding site for Tat. |
| U5 | | U5; Unique 5'; region at the 5' end of the viral genomic RNA (but found at both the 5' and 3' ends of the provirus). |
| 5' LTR | in cis | Acts as an RNA pol II promoter. The transcript begins, by definition, at the beginning of R, is capped, and proceeds through U5 and the rest of the provirus. Third generation vectors use a hybrid 5' LTR with a constitutive promoter such as CMV or RSV. |
| 3' LTR | in cis | Terminates transcription started by 5' LTR by the addition of a poly A tract just after the R sequence. |

In one example, an expression cassette is provided, comprising a RAG1 transgene operably linked to a promoter, wherein the expression cassette further comprises a nucleotide sequence encoding Woodchuck hepatitis virus (WHP) posttranscriptional regulatory element (WPRE). The sequence of WPRE is well known in the art; see for example Zanta-Boussif M A, Charrier S, Brice-Ouzet A, Martin S, Opolon P, Thrasher A J, Hope T J, Galy A. "Validation of a mutated PRE sequence allowing high and sustained transgene expression while abrogating WHV-X protein synthesis: application to the gene therapy of WAS." Gene Ther. 2009 May; 16(5):605-19. doi: 10.1038/gt.2009.3.

In other words, the expression cassette may comprise a RAG1 transgene operably linked to a MND promoter, wherein the expression cassette further comprises a nucleotide sequence encoding Woodchuck hepatitis virus (WHP) posttranscriptional regulatory element (WPRE). In one example, the expression cassette may comprise a (human) RAG1 transgene (or a codon optimised sequence thereof) operably linked to a MND promoter, wherein the expression cassette further comprises a nucleotide sequence encoding Woodchuck hepatitis virus (WHP) posttranscriptional regulatory element (WPRE). An example of a codon optimised sequence of human RAG 1 is shown in SEQ ID NO: 2 or SEQ ID NO:4.

In another example, the expression cassette may comprise a RAG1 transgene operably linked to a CMV promoter, wherein the expression cassette further comprises a nucleotide sequence encoding Woodchuck hepatitis virus (WHP) posttranscriptional regulatory element (WPRE). In one example, the expression cassette may comprise a (human) RAG1 transgene (or a codon optimised sequence thereof) operably linked to a CMV promoter, wherein the expression cassette further comprises a nucleotide sequence encoding Woodchuck hepatitis virus (WHP) posttranscriptional regulatory element (WPRE). An example of a codon optimised sequence of human RAG 1 is shown in SEQ ID NO: 2 or SEQ ID NO:4.

In another example, the expression cassette may comprise a RAG1 transgene operably linked to a RSV promoter, wherein the expression cassette further comprises a nucleotide sequence encoding Woodchuck hepatitis virus (WHP) posttranscriptional regulatory element (WPRE). In one example, the expression cassette may comprise a (human) RAG1 transgene (or a codon optimised sequence thereof) operably linked to a RSV promoter, wherein the expression cassette further comprises a nucleotide sequence encoding Woodchuck hepatitis virus (WHP) posttranscriptional regulatory element (WPRE). An example of a codon optimised sequence of human RAG 1 is shown in SEQ ID NO: 2 or SEQ ID NO:4.

In another example, the expression cassette may comprise a RAG1 transgene operably linked to a CAG promoter, wherein the expression cassette further comprises a nucleotide sequence encoding Woodchuck hepatitis virus (WHP) posttranscriptional regulatory element (WPRE). In one example, the expression cassette may comprise a (human) RAG1 transgene (or a codon optimised sequence thereof) operably linked to a CAG promoter, wherein the expression cassette further comprises a nucleotide sequence encoding Woodchuck hepatitis virus (WHP) posttranscriptional regulatory element (WPRE). An example of a codon optimised sequence of human RAG 1 is shown in SEQ ID NO: 2 or SEQ ID NO:4.

Advantageously, the expression product of the RAG1 transgene (when operably linked to a suitable promoter and when expressed in a cell (e.g. a recombinant human CD34+ haematopoietic stem cell), is at a level that is at least three-fold higher than a house keeping gene (such as ABL1) in the cell. This is particularly advantageous when the expression cassette is present in the cell at low copy numbers, such as when there are 5 or fewer copies of the expression cassette integrated into the genome of the cell (and the expression product of the RAG1 transgene (when operably linked to a suitable and when expressed in a cell (e.g. a recombinant human CD34+ haematopoietic stem cell), is still at a level that is at least three-fold higher than a house keeping gene (such as ABL1) in the cell).

Retroviral Plasmid

A retroviral plasmid is provided herein. The retroviral plasmid is also referred to as a transfer plasmid.

The retroviral plasmid comprises an expression cassette comprising a RAG1 transgene operably linked to a promoter. Suitable RAG1 transgenes are described elsewhere herein. For example, the RAG1 transgene may be a human RAG1 transgene. The human RAG1 transgene is codon optimised, as described elsewhere herein (see e.g. SEQ ID NO:2 or SEQ ID NO:4).

Suitable promoters are provided herein. As described elsewhere herein, the promoters described herein drive a high level of expression of the operably linked transgene in a cell. Advantageously, these promoters can drive the requisite level of expression of the RAG1 transgene even when the expression cassette is part of a low copy number retroviral plasmid. For example, the promoters described herein can drive expression of the operably linked RAG1 transgene in a cell such that the expression product of the RAG1 transgene in the cell is at a level that is at least x-fold higher than the corresponding expression product of a housekeeping gene (e.g. ABL1) in the cell (e.g. a recombinant human CD34+ haematopoietic stem cell). In this context, "x-fold higher" includes at least 2-fold, at least 3-fold, at least 4-fold, at least 5-fold, at least 6-fold, at least 7-fold, at least 8-fold, at least 9-fold, at least 10-fold higher than the corresponding expression product of a housekeeping gene (e.g. ABL1) in the cell (e.g. a recombinant human CD34+ haematopoietic stem cell).

The retroviral plasmid may comprise any of the expression cassettes described herein. For example, the retroviral plasmid may comprise an expression cassette comprising a RAG1 transgene operably linked to a MND promoter. Such expression cassettes are described in detail elsewhere herein.

In another example, the retroviral plasmid may comprise an expression cassette comprising a RAG1 transgene operably linked to a CMV promoter. In a further example, the retroviral plasmid may comprise an expression cassette comprising a RAG1 transgene operably linked to a CAG promoter. In an alternative example, the retroviral plasmid may comprise an expression cassette comprising a RAG1 transgene operably linked to a RSV promoter. Such expression cassettes are described in detail elsewhere herein.

Unless specifically specified otherwise, the terms "plasmid" and "vector" are used herein interchangeably.

The term "vector" is well known in the art, and refers to a nucleic acid molecule, e.g. DNA or RNA into which an expression cassette described herein may be inserted. A vector is used to transport an inserted nucleic acid molecule (in this case an expression cassette comprising a RAG1 transgene and operably linked promoter) into a suitable host cell. A vector typically contains all of the necessary elements that permit transcribing the insert nucleic acid molecule, and, preferably, translating the transcript into a polypeptide. A vector typically contains all of the necessary elements such that, once the vector is in a host cell, the vector can replicate independently of, or coincidental with, the host chromosomal DNA; several copies of the vector and its inserted nucleic acid molecule may be generated.

Vectors can be episomal vectors (i.e., that do not integrate into the genome of a host cell), or can be vectors that integrate into the host cell genome. Vectors can be non-viral or viral vectors. Non-viral vectors include but are not limited to plasmid vectors (e.g. pMA-RQ, pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Larger vectors such as artificial chromosomes (bacteria (BAC), yeast (YAC), or human (HAC)) may be used to accommodate larger inserts. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus. Another example encompasses viral plasmids mixed with cationic lipids.

The term “retroviral plasmid” is also well known in the art and as used herein refers to a plasmid derived from an RNA virus known as a retrovirus. Retroviruses have the ability to insert a copy or several copies of its genome into a host cell genome. Gamma retroviral and lentiviral plasmids are attractive for gene therapy purposes. They have been modified and developed to mediate stable genetic modification of treated cells by chromosomal integration of the transferred plasmid genomes. This technology has utility in research purposes and also clinical gene therapy which is aimed at long-term correction of genetic defects, e.g., in stem and progenitor cells. Retroviral plasmid particles with tropism for various target cells have been designed. Gamma retroviral and lentiviral plasmids have so far been used in more than 300 clinical trials, addressing treatment options for various diseases.

In one example, the retroviral plasmid described herein is a lentiviral plasmid. Alternative retroviral plasmids that may be used include MFG and MSCV.

The retroviral plasmid may be a self-inactivating (SIN) lentiviral plasmid. SIN lentiviral plasmids are useful because viral promoter/enhancer sequences are rendered inactive to significantly reduce the incidence of insertional mutagenesis.

In one example, the SIN lentiviral plasmid comprises a pCCL backbone. The pCCL backbone is well known in the art, and is advantageous because it is a third generation LV plasmid that allows virion particles to be produced at high titre and allows concentration of virion supernatant to even higher titres needed for clinical application. Alternative SIN lentiviral plasmids include pRRL, pRLL, and pCLL. These all are lentivirus transfer plasmids containing chimeric Rous sarcoma virus (RSV)-HIV or CMV-HIV 5' LTRs and plasmid backbones in which the simian virus 40 polyadenylation and (enhancerless) origin of replication sequences have been included downstream of the HIV 3' LTR, replacing most of the human sequence remaining from the HIV integration site. In pRRL, the enhancer and promoter (nucleotides −233 to −1 relative to the transcriptional start site; GenBank accession no. J02342) from the U3 region of RSV are joined to the R region of the HIV-1 LTR. In pRLL, the RSV enhancer (nucleotides −233 to −50) sequences are joined to the promoter region (from position −78 relative to the transcriptional start site) of HIV-1. In pCCL, the enhancer and promoter (nucleotides −673 to −1 relative to the transcriptional start site; GenBank accession no. K03104) of CMV were joined to the R region of HIV-1. In pCLL, the CMV enhancer (nucleotides −673 to −220) was joined to the promoter region (position −78) of HIV-1.

Therefore, as an example, the retroviral plasmid may comprise 1) an expression cassette comprising a RAG1 transgene (e.g. human RAG1 which may be codon optimised as described herein; see SEQ ID NO:2 or SEQ ID NO:4) operably linked to a MND promoter and 2) a SIN lentiviral backbone, for example with a pCCL backbone.

In another example, the retroviral plasmid may comprise 1) an expression cassette comprising a RAG1 transgene (e.g. human RAG1 which may be codon optimised as described herein; see SEQ ID NO:2 or SEQ ID NO:4) operably linked to a CMV promoter and 2) a SIN lentiviral backbone, for example with a pCCL backbone.

In another example, the retroviral plasmid may comprise 1) an expression cassette comprising a RAG1 transgene (e.g. human RAG1 which may be codon optimised as described herein; see SEQ ID NO:2 or SEQ ID NO:4) operably linked to a RSV promoter and 2) a SIN lentiviral backbone, for example with a pCCL backbone.

In another example, the retroviral plasmid may comprise 1) an expression cassette comprising a RAG1 transgene (e.g. human RAG1 which may be codon optimised as described herein; see SEQ ID NO:2 or SEQ ID NO:4) operably linked to a CAG promoter and 2) a SIN lentiviral backbone, for example with a pCCL backbone.

As described elsewhere herein, the expression cassettes provided herein may also have additional elements e.g. a nucleotide sequence encoding Woodchuck hepatitis virus (WHP) posttranscriptional regulatory element (WPRE).

For example, the retroviral plasmid may comprise the sequence of FIG. 9.

Compositions

A composition is also provided, comprising the expression cassette, plasmid or virion described herein, together with a pharmaceutically acceptable excipient, adjuvant, diluent and/or carrier. Compositions may routinely contain pharmaceutically acceptable concentrations of salt, buffering agents, preservatives, compatible carriers, supplementary immune potentiating agents such as adjuvants and cytokines and optionally other therapeutic agents or compounds.

As used herein, “pharmaceutically acceptable” refers to a material that is not biologically or otherwise undesirable, i.e., the material may be administered to an individual along with the selected binding protein without causing any undesirable biological effects or interacting in a deleterious manner with any of the other components of the pharmaceutical composition in which it is contained.

Excipients are natural or synthetic substances formulated alongside an active ingredient (e.g. an expression cassette, plasmid or virion), included for the purpose of bulking-up the formulation or to confer a therapeutic enhancement on the active ingredient in the final dosage form, such as facilitating drug absorption or solubility. Excipients can also be useful in the manufacturing process, to aid in the handling of the active substance concerned such as by facilitating powder flowability or non-stick properties, in addition to aiding in vitro stability such as prevention of denaturation over the expected shelf life. Pharmaceutically acceptable excipients are well known in the art. A suitable excipient is therefore easily identifiable by one of ordinary skill in the art. By way of example, suitable pharmaceutically acceptable excipients include water, saline, aqueous dextrose, glycerol, ethanol, and the like.

Adjuvants are pharmacological and/or immunological agents that modify the effect of other agents in a formulation. Pharmaceutically acceptable adjuvants are well known in the art. A suitable adjuvant is therefore easily identifiable by one of ordinary skill in the art.

Diluents are diluting agents. Pharmaceutically acceptable diluents are well known in the art. A suitable diluent is therefore easily identifiable by one of ordinary skill in the art.

Carriers are non-toxic to recipients at the dosages and concentrations employed and are compatible with other ingredients of the formulation. The term "carrier" denotes an organic or inorganic ingredient, natural or synthetic, with which the active ingredient is combined to facilitate the application. Pharmaceutically acceptable carriers are well known in the art. A suitable carrier is therefore easily identifiable by one of ordinary skill in the art.

Virion Production

The retroviral plasmids e.g. lentiviral plasmids described herein may be used to produce virions. To increase the safety of the virion, the components necessary for virion production are divided across multiple plasmids (three for 2nd-generation systems, four for 3rd-generation systems). The components of both systems are as follows:

- Lentiviral transfer plasmid encoding your insert of interest. The transgene sequence is flanked by long terminal repeat (LTR) sequences, which facilitate integration of the transfer plasmid sequences into the host genome. Typically, it is the sequences between and including the LTRs that is integrated into the host genome upon viral transduction. Many lentiviral transfer plasmids are based on the HIV-1 virus. For safety reasons, transfer plasmids are all replication incompetent and may contain an additional deletion in the 3'LTR, rendering the virus self-inactivating (SIN) after integration.
- Packaging plasmid(s) (can be one or two plasmids)
- Envelope plasmid In one example, SIN lentiviral plasmids are used herein as they are considered safer for gene therapy applications.

The most important component to consider and optimize is the transfer plasmid, which contains the expression cassette. 2nd generation lentiviral plasmids utilize the viral LTR promoter for gene expression, whereas 3rd-generation transfer plasmids utilize a hybrid LTR promoter. Additional or specialized promoters may also be included within a transfer plasmid: for example, the U6 promoter is included in the pSico plasmid to drive shRNA expression. Other features that can be included in transfer plasmids include: Tet- or Cre-based regulation and fluorescent fusions or reporters.

The 3rd generation system further improves on the safety of the 2nd generation in a few key ways. First, the packaging system is split into two plasmids: one encoding Rev and one encoding Gag and Pol. Second, Tat is eliminated from the 3rd generation system through the addition of a chimeric 5' LTR fused to a heterologous promoter on the transfer plasmid. Expression of the transgene from this promoter is no longer dependent on Tat transactivation. The 3rd generation transfer plasmid can be packaged by either a 2nd generation or 3rd generation packaging system.

Methods of producing transgenic retroviral (e.g. lentiviral) virions are widely known in the art (e.g. protocols such as Pike-Overzet, Leukemia, 2011). Briefly, 3-4 plasmids are transfected into A293T cells: after media change and a brief incubation period, supernatant containing the virion is removed and stored or centrifuged to concentrate virion. Crude or concentrated virion can then be used to transduce the cells of interest. Viral titres may then be determined.

Virions are therefore also provided herein which include an expression cassette comprising a RAG1 transgene operably linked to a promoter. Suitable expression cassette components are described elsewhere herein.

For the avoidance of doubt, the expression cassette present within a virion will comprise an RNA nucleic acid sequence. For example, the expression cassette present within a virion may comprise the RNA equivalent sequence to any one of SEQ ID NO:2, SEQ ID NO:3, SEQ ID NO:4, or SEQ ID NO:5.

"Transfection" in the present application refers broadly to any process of deliberately introducing nucleic acids into cells, and covers introduction of viral and non-viral vectors, and includes transformation, transduction and like terms and processes. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; whiskers-mediated transformation; and microprojectile bombardment (Klein et al. (1987) Nature 327:70).

Therapy

Methods for treating a patient without a functional Rag1 gene or RAG1 protein are provided herein. For example, provided herein are methods for treating a patient with RAG1 deficient severe combined immunodeficiency (RAG1-SCID) or Omenn Syndrome. Complete loss-of-function of RAG1 in humans produces a severe immunodeficiency in humans. Therefore, patients without a functional Rag1 gene of RAG1 protein are typically identified during infancy.

The methods provided herein are also for treating a patient with at least one mutation in the RAG1 protein. In other words, the method is for treating a disease caused by at least one mutation in the RAG1 protein. These diseases are characterised by a partial loss of functional RAG1 in a patient i.e. the patient may have a hypomorphic RAG1 variant. Diseases caused by hypomorphic RAG1 variants worsen at a slower rate than diseases caused by a complete loss-of-function of RAG1 because RAG1 variants can retain partial recombination activity. Consequently, life-threatening complications in diseases associated with hypomorphic RAG1 may not appear for several years. Said diseases are often underdiagnosed but are likely to be much more common than RAG1-SCID or OS. Next generation sequencing efforts in primary immune-deficiency patients have revealed many hypomorphic RAG1 mutations for which no curative treatment is currently available in the clinic. Indeed, 71 RAG1 variants have been functionally assayed to date. The phenotype associated with hypomorphic RAG1 variants is combined immunodeficiency with granuloma and/or autoimmunity (CID-G/A). RAG1 deficiency can be measured by in vitro quantification of recombination activity. Examples of diseases caused by hypomorphic RAG1 variants that can be treated by the methods described herein are atypical SCID or combined immunodeficiency (CID). CID is a set of diseases characterized by hypomorphic RAG1 mutations leading to diminished immune repertoire.

The methods provided herein are particularly useful when treating a patient with RAG1 deficient severe combined immunodeficiency (RAG1-SCID) or Omenn Syndrome. However, as stated above, they may also be useful in treating a patient with atypical SCID or combined immunodeficiency (CID). Accordingly, although the invention is predominantly described in the context of RAG1-SCID or Omenn Syndrome, all such aspects of the invention equally apply to atypical SCID or combined immunodeficiency (CID).

The method may include an ex vivo cell-based therapy. Suitable methodology for use in such methods is well known in the art; see for example:

"Improving Lentiviral Transduction of CD34+ Hematopoietic Stem and Progenitor Cells" April 2018 Human Gene Therapy Methods 29(2) DOI: 10.1089/hgtb.2017.085; or PLoS One. 2009 Jul. 30; 4(7):e6461. doi: 10.1371/journal.pone.0006461. "Towards a clinically relevant lentiviral transduction protocol for primary human CD34 hematopoietic stem/progenitor cells." Millington M1, Arndt A, Boyd M, Applegate T, Shen S.

For example, a hematopoietic progenitor cell, such as a HSC (e.g. a CD34+ HSC), may be isolated from the patient. Methods for doing so are described elsewhere herein. The genome of these cells can be altered by using the expression cassette, plasmids, virions or compositions and methods described herein. The recombinant cells may then be transplanted back into the patient.

The terms "hematopoietic progenitor cell" and "hematopoietic stem cell" refer to cells of a stem cell lineage that give rise to all the blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells).

Suitably; the hematopoietic progenitor cell, e.g. a HSC, expresses at least one of the following cell surface markers characteristic of hematopoietic progenitor cells: CD34+, CD59+, ThyI/CD90+, CD381 o/−, and C-kit/CDI 17+. Most preferably, the hematopoietic progenitors are CD34+ HSCs.

HSCs are an important target for gene therapy as they provide a prolonged source of the corrected cells. HSCs give rise to both the myeloid and lymphoid lineages of blood cells. Mature blood cells have a finite life-span and must be continuously replaced throughout life. Blood cells are continually produced by the proliferation and differentiation of a population of pluripotent HSCs that can replenished by self-renewal. Bone marrow (BM) is the major site of hematopoiesis in humans and a good source for hematopoietic stem and progenitor cells (HSPCs). HSPCs can be found in small numbers in the peripheral blood (PB). In some indications or treatments their numbers increase. The progeny of HSCs mature through stages, generating multi-potential and lineage-committed progenitor cells including the lymphoid progenitor cells giving rise to the cells expressing RAG1 B and T cell progenitors are the two cell populations requiring the activity of RAG1, so they could be transfected at the stages prior to re-arrangement, though correcting progenitors has the advantage of continuing to be a source of corrected cells.

The method may therefore include an ex vivo method of generating a recombinant CD34+ haematopoietic stem cell, the method comprising contacting a CD34+ haematopoietic stem cell with a virion as described herein under conditions in which the expression cassette is incorporated and expressed by the cell to generate the recombinant CD34+ haematopoietic stem cell. As used herein, "conditions in which the expression cassette is incorporated and expressed by the cell to generate the recombinant CD34+ haematopoietic stem cell" may include culturing the cells in the presence of appropriate media and growth factors, followed by incubation with a lentiviral virion described herein. Optionally, retronectin, proteamine sulphate or other compounds facilitating viral transduction (transduction enhancers) may be included.

In one example, CD34+ cells from patients' blood or bone marrow are isolated, cultured ex vivo under GMP grade conditions with media and growth factors, followed by an additional incubation with the lentiviral virion with retronectin, proteamine sulphate or other compounds facilitating viral transduction (transduction enhancers). Additional culturing and sometimes a second "hit" of virus may be included. At the end of the culture period cells may be harvested and collected in iv bags to be given to the patient (or frozen in liquid nitrogen until required, with subsequent thawing and iv injection).

The term "recombinant" cell refers to a cell that comprises at least one integrated expression cassette.

A recombinant CD34+ haematopoietic stem cell is therefore also provided herein, comprising an expression cassette comprising a RAG1 transgene operably linked to a promoter (the details of which are described elsewhere herein). Advantageously, when promoters described herein are used in combination with the transgenes described herein, the requisite level of transgene expression is achieved, even when a low copy number retroviral plasmid is used. In other words, using the expression cassettes, plasmids and virions described herein, the expression product of the RAG1 transgene in the resultant recombinant CD34+ haematopoietic stem cell is at a level that is at least three-fold higher than ABL1 in the cell when there are 5 or fewer copies of the expression cassette integrated into the genome of the recombinant human CD34+ haematopoietic stem cell.

Advantageously, the combination of the promoter and RAG1 transgene in the expression cassette drives RAG1 expression in each of the above cell types to a minimum threshold level that is therapeutic (due to the nature of the promoters being used; i.e. their ability to drive expression of the transgene such that the expression product of the transgene is at a level that is at least three fold higher than that of a housekeeping gene such as ABL1 in the cell (even when there are 5 or fewer copies of the expression cassette integrated into the genome of the cell, in other words, when a low copy number plasmid is used)).

In one example, a method of treating RAG1 deficient SCID or OS in a subject is therefore provided, the method comprising the steps of:

(i) extracting CD34+ haematopoietic stem cells from the subject;
(ii) contacting the cells from (i) with a virion described herein;
(iii) incubating the cells from (ii) for a period of time, preferably for 12 to 84 hours, further preferably for 12 to 72 hours; and
(iv) introducing the cells from (iii) back into the subject in need of treatment.

A biopsy or aspirate of tissue or fluid may be taken from the bone marrow of the subject in order to extract the CD34+ haematopoietic stem cells. A biopsy or aspirate may be performed according to any of the known methods in the art. For example, in a bone marrow aspirate, a large needle is used to enter the pelvis bone to collect bone marrow.

A hematopoietic progenitor cell may be extracted from the biopsy or aspirate by any method known in the art. For example, CD34+ cells may be enriched using CliniMACS® Cell Selection System (Miltenyi Biotec). CD34+ cells may also be weakly stimulated in serum-free medium (e.g., CellGrow SCGM media, CellGenix) with cytokines (e.g., SCF, rhTPO, rhFLT3).

The cells may then be contacted with the virion using methods well known in the art and incubated together for an appropriate period of time.

Clearance of bone-marrow niches may be required prior to transplantation of the recombinant cells back into the patient. Current methods rely on radiation and/or chemotherapy. Accordingly, the method may optionally include the step of administering chemotherapy to the subject prior to step (iv). Suitable chemotherapy regimens are well known to a person of skill in the art.

However, due to the limitations and adverse effects of radiation and/or chemotherapy, safer conditioning regimens have been and are being developed, such as immunodepletion of bone marrow cells by antibodies or antibody toxin conjugates directed against hematopoietic cell surface markers for example CD17, c-kit and others. Such methods may also form part of the methods described herein.

The methods then include a step of introducing the cells from back into the subject in need of treatment. It is also referred to herein as transplanting the recombinant cells back into the patient. This transplanting step may be accomplished using any method of transplantation known in the art. For example, the recombinant cells may be injected directly in the patient's blood or otherwise administered to the patient.

By introducing the expression cassette into autologous cells that are derived from and therefore already completely immunologically matched with the patient in need, it is possible to generate cells that can be safely re-introduced into the patient, and effectively give rise to a population of cells that will be effective in ameliorating one or more clinical conditions associated with the patient's disease.

The examples provided above refer to HSCs. However, alternatively, a white blood cell isolated from the patient could be used in the therapies described above.

A patient specific induced pluripotent stem cell (iPSC) may be created. Then, the genome of these iPS cells may be altered by using the expression cassette, plasmids, virions or compositions and methods described herein. The iPSCs may then be differentiated into hematopoietic progenitor cells or white blood cells. Finally, the hematopoietic progenitor cells or white blood cells may be implanted into the patient.

Alternatively, a mesenchymal stem cell is isolated from the patient and could be used in the therapies described above.

One advantage of ex vivo cell therapy is that a comprehensive analysis of the therapeutic agent can be conducted prior to administration. Furthermore, populations of specific cells, including clonal populations, can be isolated or enriched for prior to implantation.

A method for in vivo based therapy is also described. In this method, the chromosomal DNA of the cells in the patient is corrected using the materials and methods described herein. Suitably, the cells are white blood cells, bone marrow cells, hematopoietic progenitor cells, HSC or HSC CD34+ cells.

Although blood cells present an attractive target for ex vivo treatment and therapy, increased efficacy in delivery may permit direct in vivo delivery to the HSCs and/or other B and T cell progenitors, such as CD34+ cells. Ideally the targeting and incorporation of the expression cassette would be directed to the relevant cells.

An advantage of in vivo gene therapy is the ease of therapeutic production and administration. The same therapeutic approach and therapy will have the potential to be used to treat more than one patient, for example a number of patients who share the same or similar genotype or allele. In contrast, ex vivo cell therapy typically requires using a patient's own cells, which are isolated, manipulated and returned to the same patient.

Pharmaceutically Acceptable Carriers for Recombinant Cells

The ex vivo methods of administering the recombinant cells to a subject contemplated herein involve the use of therapeutic compositions comprising recombinant cells.

Therapeutic compositions contain a physiologically tolerable carrier together with the recombinant cell composition, and optionally at least one additional bioactive agent as described herein, dissolved or dispersed therein as an active ingredient. Suitably, the therapeutic composition is not substantially immunogenic when administered to a mammal or human patient for therapeutic purposes, unless so desired.

In general, the recombinant cells described herein are administered as a suspension with a pharmaceutically acceptable carrier. One of skill in the art will recognise that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising recombinant cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A recombinant cell composition can also be emulsified or presented as a liposome composition, provided that the emulsification procedure does not adversely affect cell viability. The recombinant cells and any other active ingredient can be mixed with excipients that are pharmaceutically acceptable and compatible with the active ingredient, and in amounts suitable for use in the therapeutic methods described herein.

Additional agents included in a recombinant cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the recombinant cell compositions that is effective in the treatment of a particular disorder or condition will depend on the nature of the disorder or condition, and can be determined by standard clinical techniques.

Administration & Efficacy of Recombinant Cells

The terms "administering," "introducing" and "transplanting" are used interchangeably in the context of the placement of recombinant cells, e.g., HPSC cells, into a subject, by a method or route that results in at least partial localisation of the introduced cells at a desired site, such as a site of injury or repair, such that a desired effect(s) is produced. The recombinant cells e.g., HPSC cells, can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e. long-term engraftment. For example, in some embodiments described herein, an effective amount of myogenic progenitor cells is administered via a systemic route of administration, such as an intraperitoneal or intravenous route.

The terms "individual", "subject," "host" and "patient" are used interchangeably herein and refer to any subject for whom diagnosis, treatment or therapy is desired. For the purposes of the present disclosure, the subject may be a primate, preferably a human, or another mammal, such as a dog, cat, horse, pig, goat, or bovine, and the like.

When provided prophylactically, recombinant cells described herein can be administered to a subject in advance of any symptom of SCID and/or Omenn Syndrome, e.g., prior to the development of alpha/beta T-cell lymphopenia with gamma/delta T-cell expansion, severe cytomegalovirus (CMV) infection, autoimmunity, chronic inflammation of the skin, eosinophilia, failure to thrive, swollen lymph nodes, swollen spleen, diarrhea and enlarged liver. Accordingly, the prophylactic administration of a hematopoietic progenitor cell population serves to prevent SCID and/or Omenn Syndrome.

When provided therapeutically, the HPSC are provided at (or after) the onset of a symptom or indication of SCID and/or Omenn Syndrome, e.g., upon the onset of disease.

Suitably, the HPSC population being administered according to the methods described herein comprises allogeneic HPSC obtained from one or more donors. "Allogeneic" refers to a HPSC or biological samples comprising HPSC obtained from one or more different donors of the same species, where the genes at one or more loci are not identical. For example, a HPSC population being administered to a subject can be derived from one more unrelated donor subjects, or from one or more non-identical siblings, Suitably, syngeneic hematopoietic progenitor cell populations can be used, such as those obtained from genetically identical animals, or from identical twins. Alternatively, the HPSC are autologous cells; that is, the HPSC are obtained or isolated from a subject and administered to the same subject, i.e. the donor and recipient are the same.

The term "effective amount" refers to the amount of a population of recombinant cells or their progeny needed to prevent or alleviate at least one or more signs or symptoms of SCID and/or Omenn Syndrome, and relates to a sufficient amount of a composition to provide the desired effect, e.g., to treat a subject having SCID and/or Omenn Syndrome. The term "therapeutically effective amount" therefore refers to an amount of recombinant cells or a composition comprising recombinant cells that is sufficient to promote a particular effect when administered to a typical subject, such as one who has or is at risk for SCID and/or Omenn Syndrome. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

Suitably, an effective amount of HPSC comprises at least $10^2$ HPSC, at least $5\times10^2$ HPSC, at least $10^3$ HPSC, at least $5\times10^6$ HPSC, at least $10^4$ HPSC, at least $5\times10^4$ HPSC, at least $10^5$ HPSC, at least $2\times10^5$ HPSC, at least $3\times10^5$ HPSC, at least $4\times10^5$ HPSC, at least $5\times10^5$ HPSC, at least $6\times10^5$ HPSC, at least $7\times10^5$ HPSC, at least $8\times10^5$ HPSC, at least $9\times10^5$ HPSC, at least $1\times10^6$ HPSC, at least $2\times10^6$ HPSC, at least $3\times10^6$ HPSC, at least $4\times10^6$ HPSC, at least $5\times10^6$ HPSC, at least $6\times10^6$ HPSC, at least $7\times10^6$ HPSC, at least $8\times10^6$ HPSC, at least $9\times10^6$ HPSC, or multiples thereof. The HPSC are derived from one or more donors, or are obtained from an autologous source, Suitably, the HPSC described herein are expanded in culture prior to administration to a subject in need thereof.

"Administered" refers to the delivery of HPSC composition into a subject by a method or route that results in at least partial localisation of the cell composition at a desired site, A cell composition can be administered by any appropriate route that results in effective treatment in the subject, i.e. administration results in delivery to a desired location in the subject where at least a portion of the composition delivered, i.e. at least $1\times10^4$ cells are delivered to the desired site for a period of time. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous. For the delivery of cells, administration by injection or infusion can be made.

Suitably, the cells are administered systemically. The phrases "systemic administration," "administered systemically", "peripheral administration" and "administered peripherally" refer to the administration of a population of progenitor cells other than directly into a target site, tissue, or organ, such that it enters, instead, the subject's circulatory system and, thus, is subject to metabolism and other like processes.

The efficacy of a composition for the treatment of SCID and/or Omenn Syndrome can be determined by the skilled clinician. A treatment is considered "effective" if any one or more of the signs or symptoms of disease are altered in a beneficial manner. As an example, a treatment is considered effective when the level of functional RAG1 protein of interest is at a level that is at least three-fold higher in a CD34+ cell than the level of an appropriate housekeeping gene (e.g. ABL1), Efficacy can also be measured by failure of an individual to worsen as assessed by hospitalisation or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

The treatment according to the present disclosure ameliorates one or more symptoms associated with SCID and/or Omenn Syndrome by increasing the amount of functional RAG1 in the individual. Early signs typically associated with SCID and/or Omenn Syndrome include for example, development of alpha/beta T-cell lymphopenia with gamma/delta T-cell expansion, severe cytomegalovirus (CMV) infection, autoimmunity, chronic inflammation of the skin, eosinophilia, failure to thrive, swollen lymph nodes, swollen spleen, diarrhoea and enlarged liver.

Kits

Also provided herein are kits for carrying out the methods of the invention. A kit can include one or more of an expression cassette of the invention, a plasmid of the invention or a virion of the invention, and/or any nucleic acid or proteinaceous molecule necessary to carry out the embodiments of the methods of the invention, or any combination thereof. Suitably, the kit may contain a reagent and/or for reconstitution and/or dilution of the plasmid(s). Suitably, the components of a kit may be in separate containers, or combined in a single container.

Suitably, a kit as described above further comprises one or more additional reagents, where such additional reagents are selected from a buffer, a buffer for introducing a polypeptide or polynucleotide into a cell, a wash buffer, a control reagent and the like. A buffer can be a stabilization buffer, a reconstituting buffer, a diluting buffer, or the like.

In addition to the above-mentioned components, a kit can further include instructions for using the components of the kit to practice the methods. The instructions for practicing the methods are generally recorded on a suitable recording medium. For example, the instructions may be printed on a substrate, such as paper or plastic, etc. The instructions may be present in the kits as a package insert, in the labelling of the container of the kit or components thereof (i.e., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this embodiment is a kit that includes a web address where the instructions can be viewed and/or from which the instructions can be downloaded. As with the instructions, this means for obtaining the instructions can be recorded on a suitable substrate.

General Definitions

"Complementary" or "complementarity", as used herein, refers to the Watson-Crick base-pairing of two nucleic acid sequences. For example, for the sequence 5'-AGT-3' binds to the complementary sequence 3'-TCA-5'. Complementarity between two nucleic acid sequences may be "partial", in which only some of the bases bind to their complement, or it may be complete as when every base in the sequence binds to its complementary base. The degree of complementarity between nucleic acid strands has significant effects on the efficiency and strength of hybridisation between nucleic acid strands.

The term "hybridising" means annealing to two at least partially complementary nucleotide sequences in a hybridization process. In order to allow hybridisation to occur complementary nucleic acid molecules are generally thermally or chemically denatured to melt a double strand into two single strands and/or to remove hairpins or other secondary structures from single-stranded nucleic acids. The stringency of hybridisation is influenced by conditions such as temperature, salt concentration and hybridisation buffer composition. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. High stringency conditions for hybridisation include high temperature and/or low sodium/salt concentration (salts include sodium as for example in NaCl and Na-citrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. By way of non-limiting example, representative salt and temperature conditions for stringent hybridization are: 1×SSC, 0.5% SDS at 65° C. The abbreviation SSC refers to a buffer used in nucleic acid hybridization solutions. One litre of a 20× (twenty times concentrate) stock SSC buffer solution (pH 7.0) contains 175.3 g sodium chloride and 88.2 g sodium citrate. A representative time period for achieving hybridisation is 12 hours.

The terms "identity" and "identical" and the like refer to the sequence similarity between two polymeric molecules, e.g., between two nucleic acid molecules, such as between two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250).

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, MD), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method. Typically, the percentage sequence identity is calculated over the entire length of the sequence.

For example, a global optimal alignment is suitably found by the Needleman-Wunsch algorithm with the following scoring parameters: Match score: +2, Mismatch score: −3; Gap penalties: gap open 5, gap extension 2. The percentage identity of the resulting optimal global alignment is suitably calculated by the ratio of the number of aligned bases to the total length of the alignment, where the alignment length includes both matches and mismatches, multiplied by 100.

While the making and using of various embodiments of the present invention are discussed in detail herein, it should be appreciated that the present invention provides many applicable inventive concepts that can be embodied in a wide variety of specific contexts. The specific embodiments discussed herein are merely illustrative of specific ways to make and use the invention and do not limit the scope of the invention.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Ausubel, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); U.S. Pat. No. 4,683,195; Nucleic Acid Hybridization (Harries and Higgins eds. 1984); Transcription and Translation (Hames and Higgins eds. 1984); Culture of Animal Cells (Freshney, Alan R. Liss, Inc., 1987); Immobilized Cells and Enzymes (IRL Press, 1986); Perbal, A Practical Guide to Molecular Cloning (1984); the series, Methods in Enzymology (Abelson and Simon, eds.-in-chief, Academic Press, Inc., New York), specifically, Vols. 154 and 155 (Wu et al. eds.) and Vol. 185, "Gene Expression Technology" (Goeddel, ed.); Gene Transfer Vectors For Mammalian Cells (Miller and Calos eds., 1987, Cold Spring Harbor Laboratory); Immunochemical Methods in Cell and Molecular Biology (Mayer and Walker, eds., Academic Press, London, 1987); Handbook of Experimental Immunology, Vols. I-IV (Weir and Blackwell, eds., 1986); and Manipulating the Mouse Embryo, (Cold Spring Harbor Laboratory Press, Cold Spring Harbor, N.Y., 1986).

Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

EXAMPLES

Results

MND Promoter as Most Optimal Vector to Correct Rag 1 Deficiency.

Figure 1:
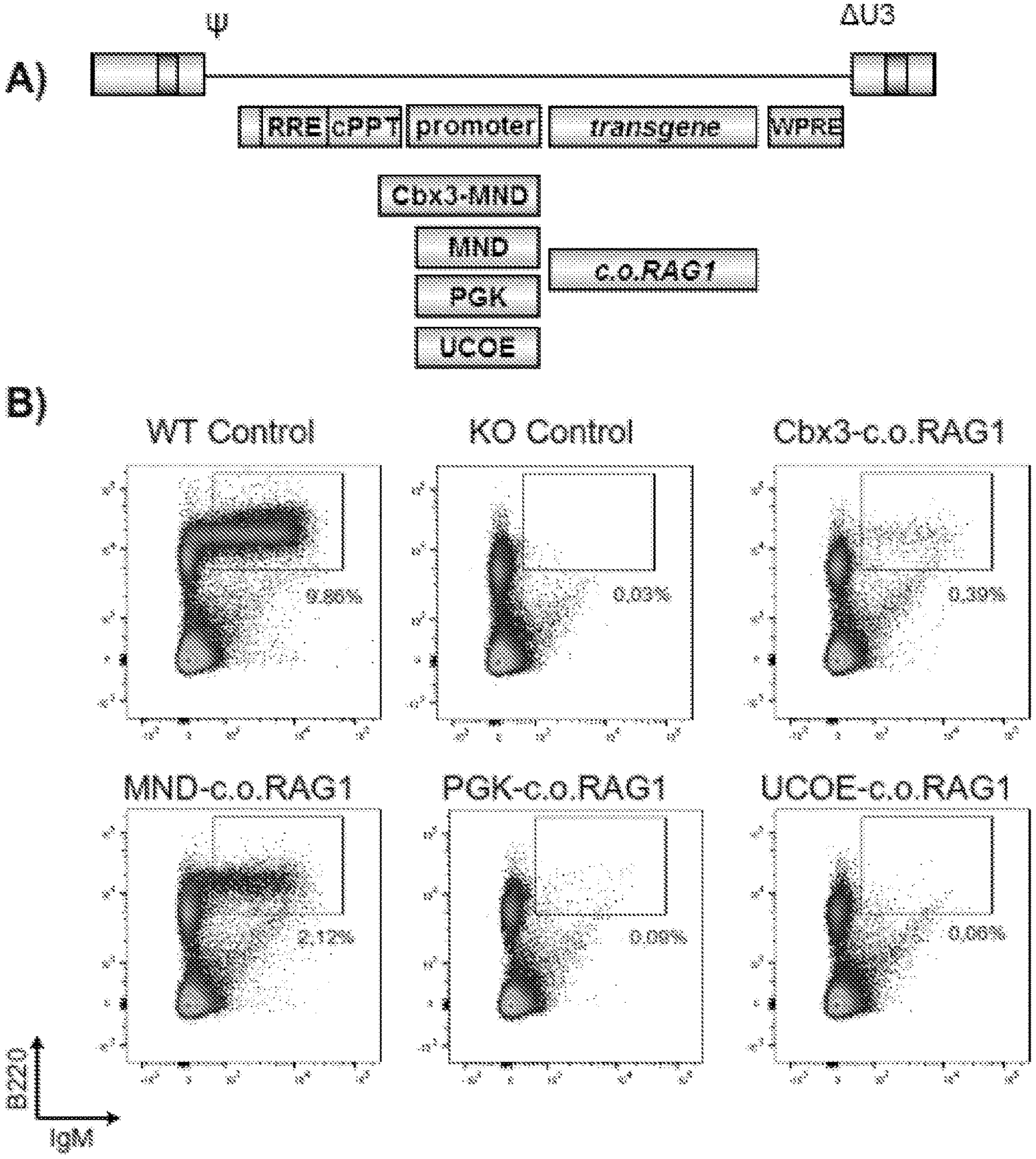
FIG. 1: Identifying the most optimal SIN LV plasmid to restore immune reconstitution of Rag1 deficiency. A) Four different SIN LV plasmids in the CCL backbone carrying different promoters (Cbx3-MND, MND, PGK and UCOE promoter) were tested to drive expression of a codon optimized version of RAG1. B) Representative FACS plots showing the restoration of $B220^{hi+}$ B cells in the BM. C) Total number of B cells ($B220^{hi+}$) in the PB (top panel) and total number of the different B cell subsets in the BM (bone marrow) (bottom panel) 16 weeks after SC transplantation. Graphs represent the means and standard deviation of a pilot experiment with 2-3 mice per group. (Mann-Withney test, one-tailed, *p≤0.05). ID) Representative FACS plots of the thymus reconstitution (CD4 vs CD8) with the different constructs. E) Total number of T cells ($CD3^+TCR\alpha\beta^+$) in PB (top panel) and total number of the different T cell subsets in the thymus (bottom panel) 16 weeks after transplantation. Graphs represent the means and standard deviation of a pilot experiment with 2-3 mice per group. (Mann-Withney test, one-tailed, *p≤0.05).
Figure 1:
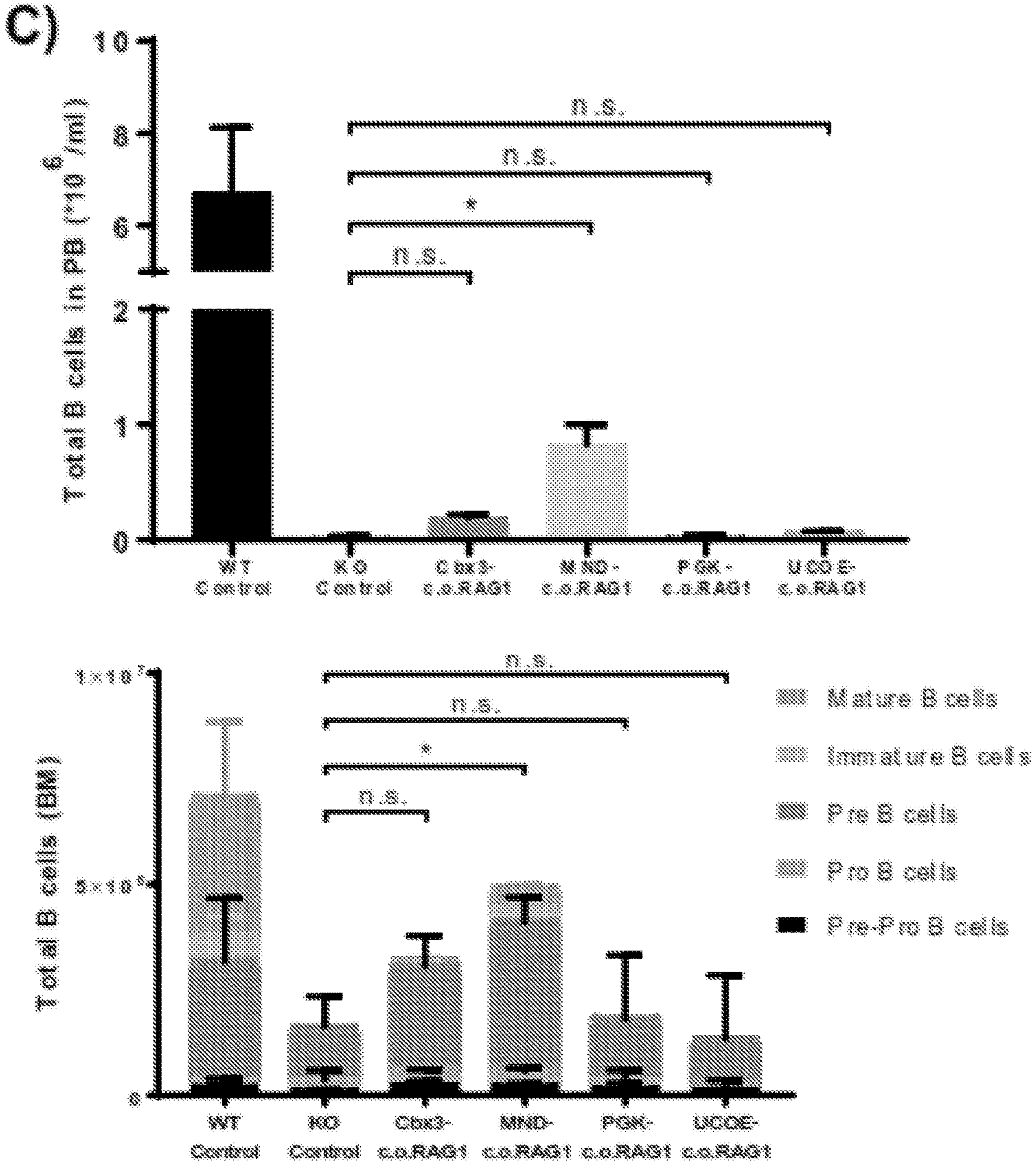
Figure 1:
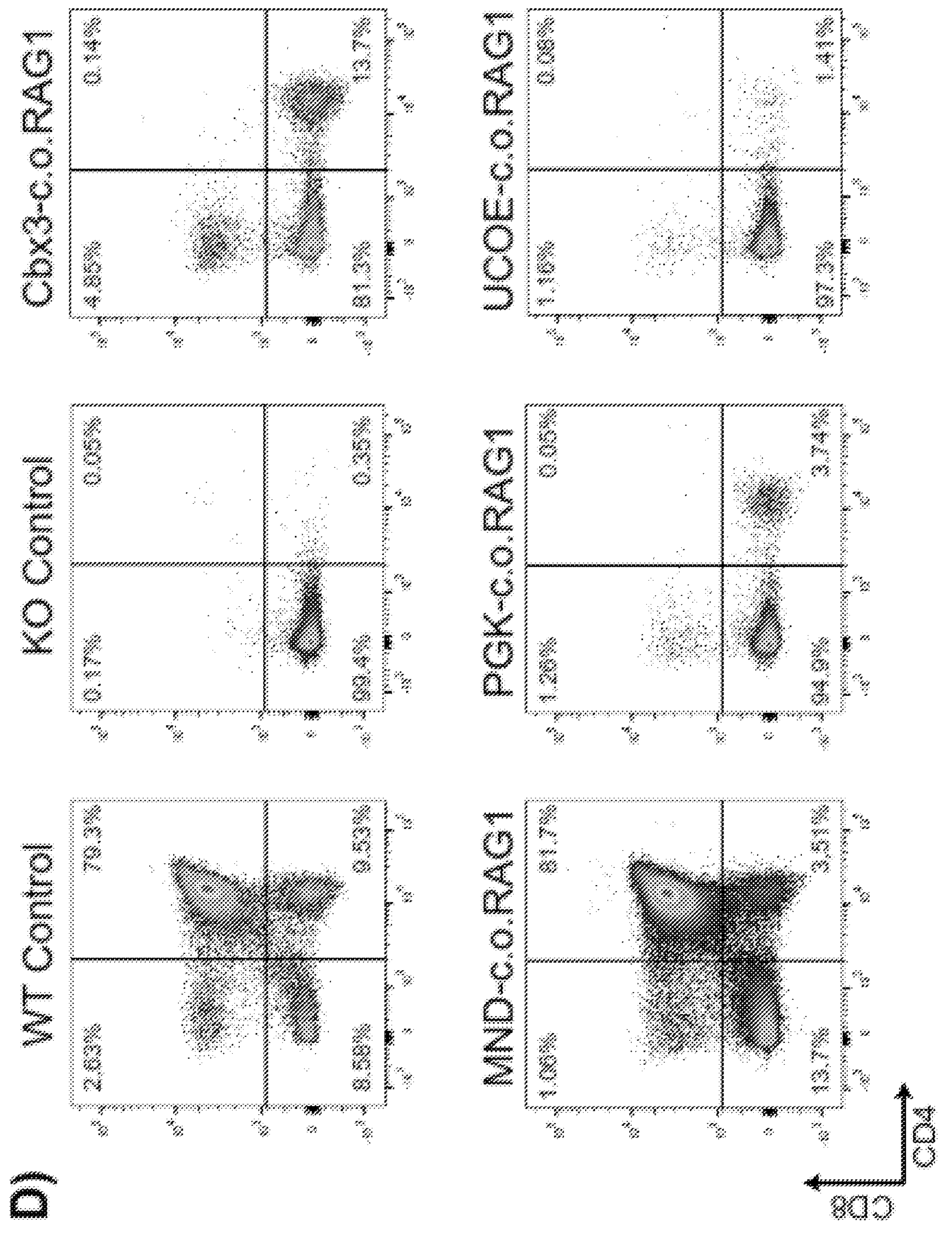
Figure 1:
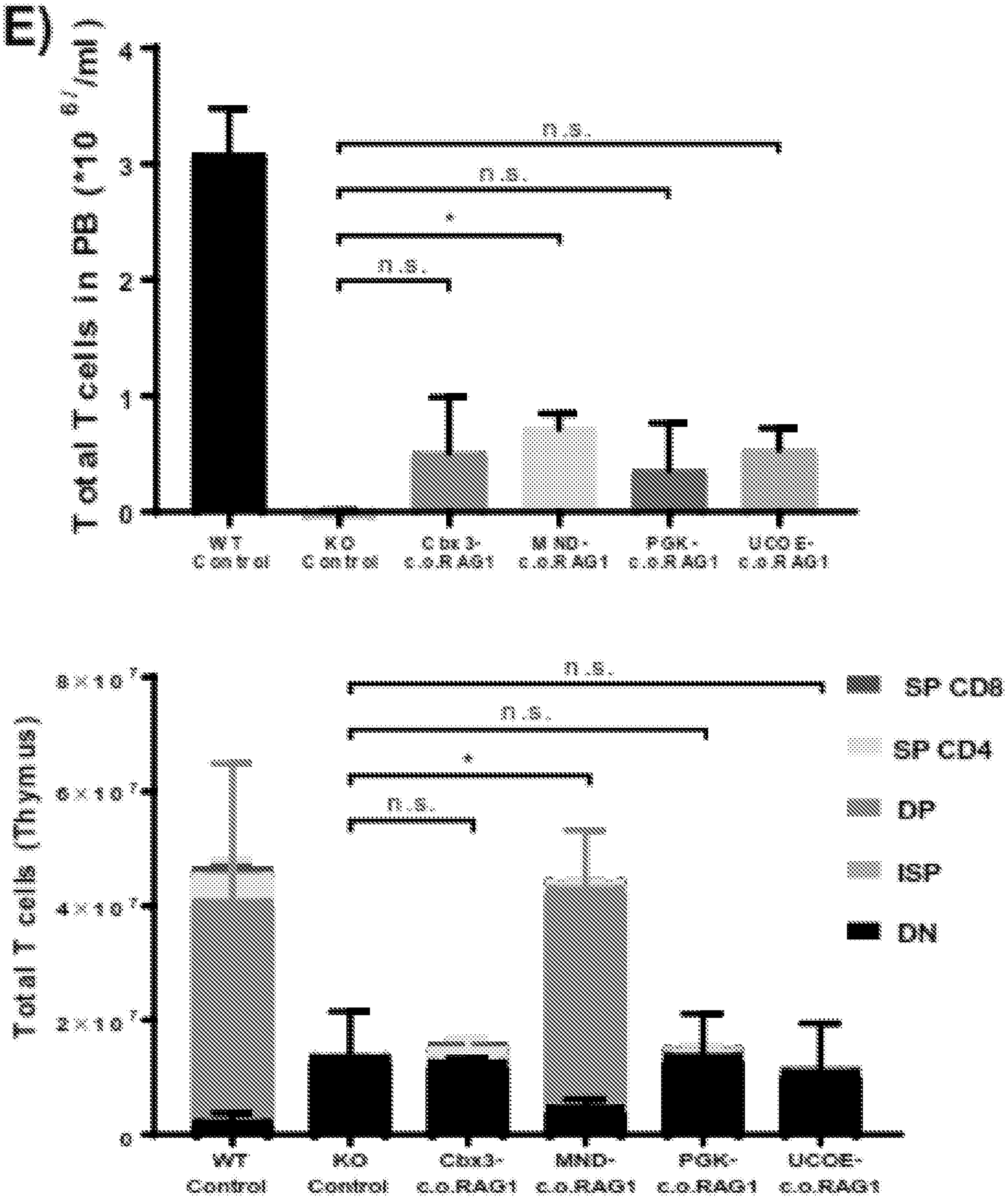

At the onset of this project the inventors constructed four different SIN LV plasmids in the CCL backbone and tested four different promoters that have been used in other clinical trials before: PGK (Phospho Glycerate Kinase), MND (myeloproliferative sarcoma virus enhancer, negative control region deleted, d1587rev primer binding site substituted), the chromatin-remodeling element (UCOE), and a combination of UCOE and MND (Cbx-MND) were used to drive expression of a codon optimized version of the RAG1 (FIG. 1A). Recombinant lentivirus were produced by transfecting the transfer vectors in conjunction with a GAG-Pol, REV and envelope (VSV-G) plasmid and subsequently used to transduce lineage negative BM cells from Rag1 deficient mice. Rag1 KO mice were transplanted with wild-type (WT) stem cells, mock transduced Rag1 KO stem cells or gene therapy treated stem cells using the four different promoters. Mice were bled every four weeks and sacrificed after 16 weeks, after which they were extensively analysed by flow cytometry and Q-PCR for viral copy number (VCN), WPRE (Woodchuck Hepatitis Virus Posttranscriptional Regulatory Element) and expression of the therapeutic gene RAG1 (FIG. 7A). Reflecting the known promoter strengths of these four vectors, a wide range of RAG1 expression was created in the initial experiments. Mice were sacrificed after 4 months, or if they showed signs of illness before that time and immune organs were analysed by flow cytometry. Restoration of IgM+B220+B cells (FIG. 1B) in the BM was seen in mice treated with wt stem cells and MND-c.o.RAG1 treated gene therapy mice and occasionally in mice with Cbx3-MND elements, but not with mice in which the PGK or UCOE promoter was used (FIG. 1B, C). Mock transduced Rag1 KO stem cells as expected did not restore B cell development, where cells were blocked at the pre B cell stage.

We next analysed the thymus for T cell expression, using (amongst other markers) CD4 and CD8. Proper T cell development with a full spectrum of DP and SP developmental stages was observed with wt and MND-c.o.RAG1 cells, but not in any of the other promoters used (FIG. 1D, E).

In the low c.o.RAG1 expression groups, inventors found a number of mice (n=4 out of 9) developed skin rashes, while the animals in the high c.o.RAG1 expression group as well as the animals that received wild-type cells or uncorrected Rag1 knock-out cells did not display any health problems.

Figure 2:
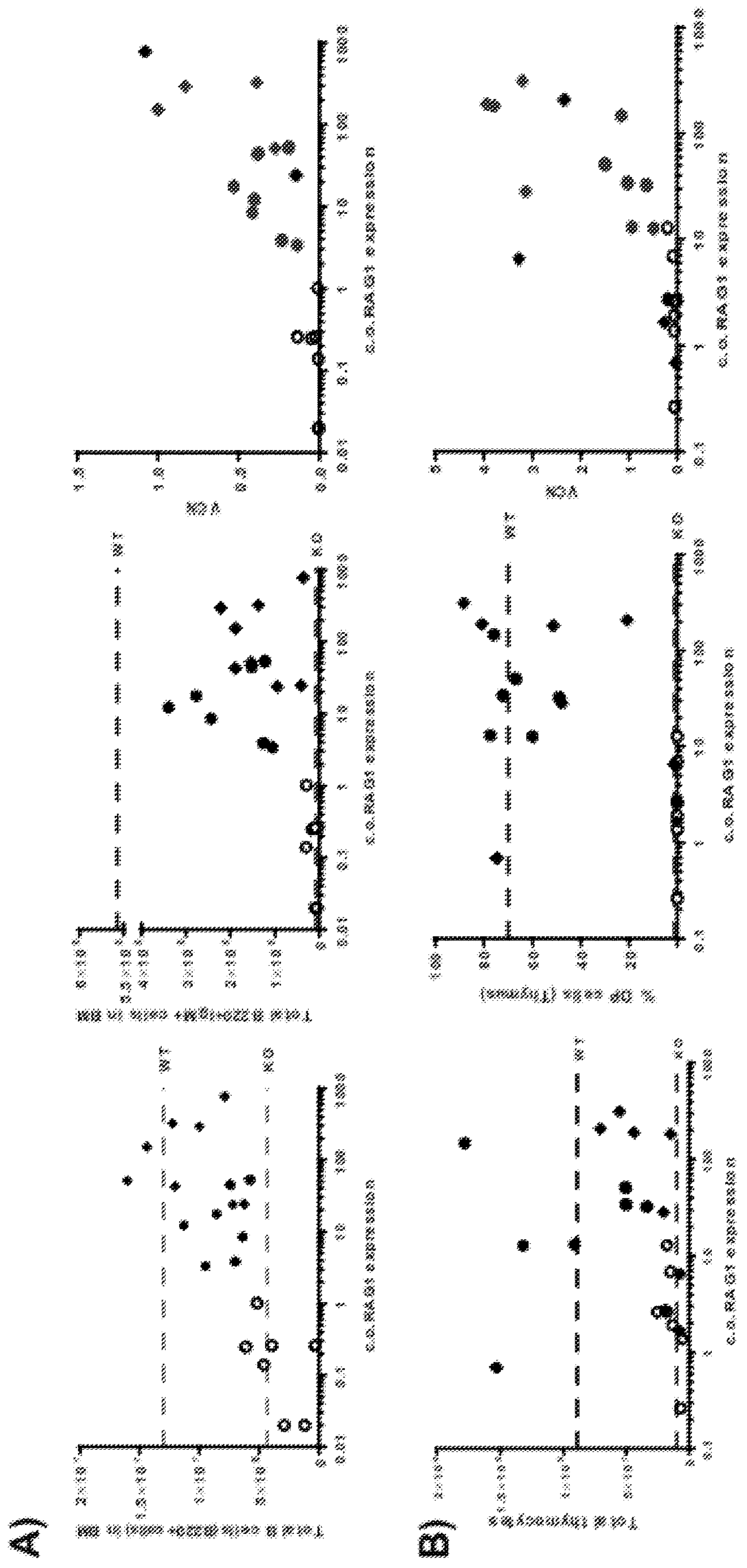
FIG. 2: Correlation of immune reconstitution with RAG1 expression and safety of the different vectors. A) total number of $B220^+$ cells (right panel) and total number of $B220^+IgM^+$ cells (middle panel) correlation with the expression of c.o.RAG1 in BM. Correlation between VCN (vector/plasmid copy number) and c.o.RAG1 expression in BM of immune reconstituted mice (left panel, red=immune reconstitution achieved). B) Correlation between total thymocytes (right panel) and DP cells (middle panel) with c.o.RAG1 expression in the thymus. Correlation between VCN and c.o.RAG1 expression in the thymus of immune reconstituted mice (left panel, red=immune reconstitution achieved). In all but one mouse immune reconstruction was received. Only with extremely high RAG1 levels reconstitution was low/minimal. Data shown represents 3 independent in vivo experiments (•, ⬢, ◆: filled=MND promoter; empty=other promoters). Each dot represents one mouse—in all but one mouse immune reconstitution was obtained C) IVIM assay was performed on the different constructs to assess their safety (mock cells as negative control; RSF91 gammaretroviral vector as a positive control). Data shows results form 3 complete IVIM assays. D) TCR Vβ repertoire analysis by GeneScan. A total of 24 Vβ families was analysed on spleen cells from 3 mice per group. Overall score of all the families was calculated for the different constructs. E) Representative samples of GeneScan plots are shown for four different families (x-axis indicates CDR3 length; y-axis shows the fluorescence intensity of the runoff products).
Figure 2:
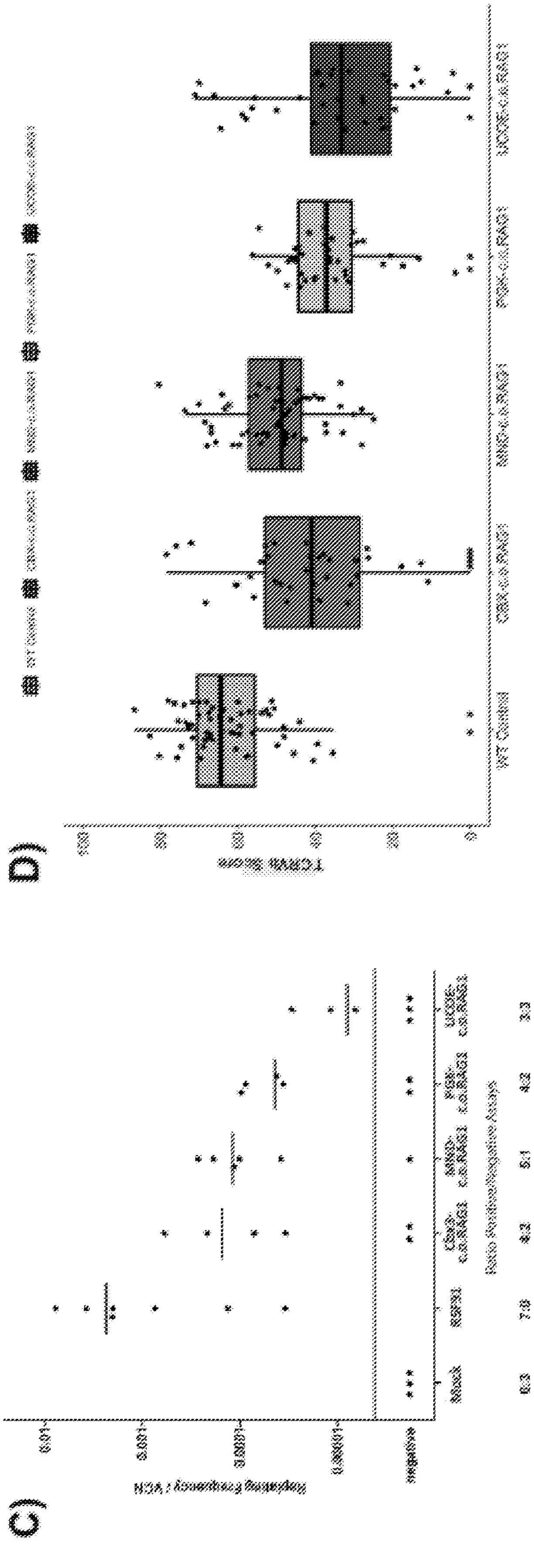
Figure 2:
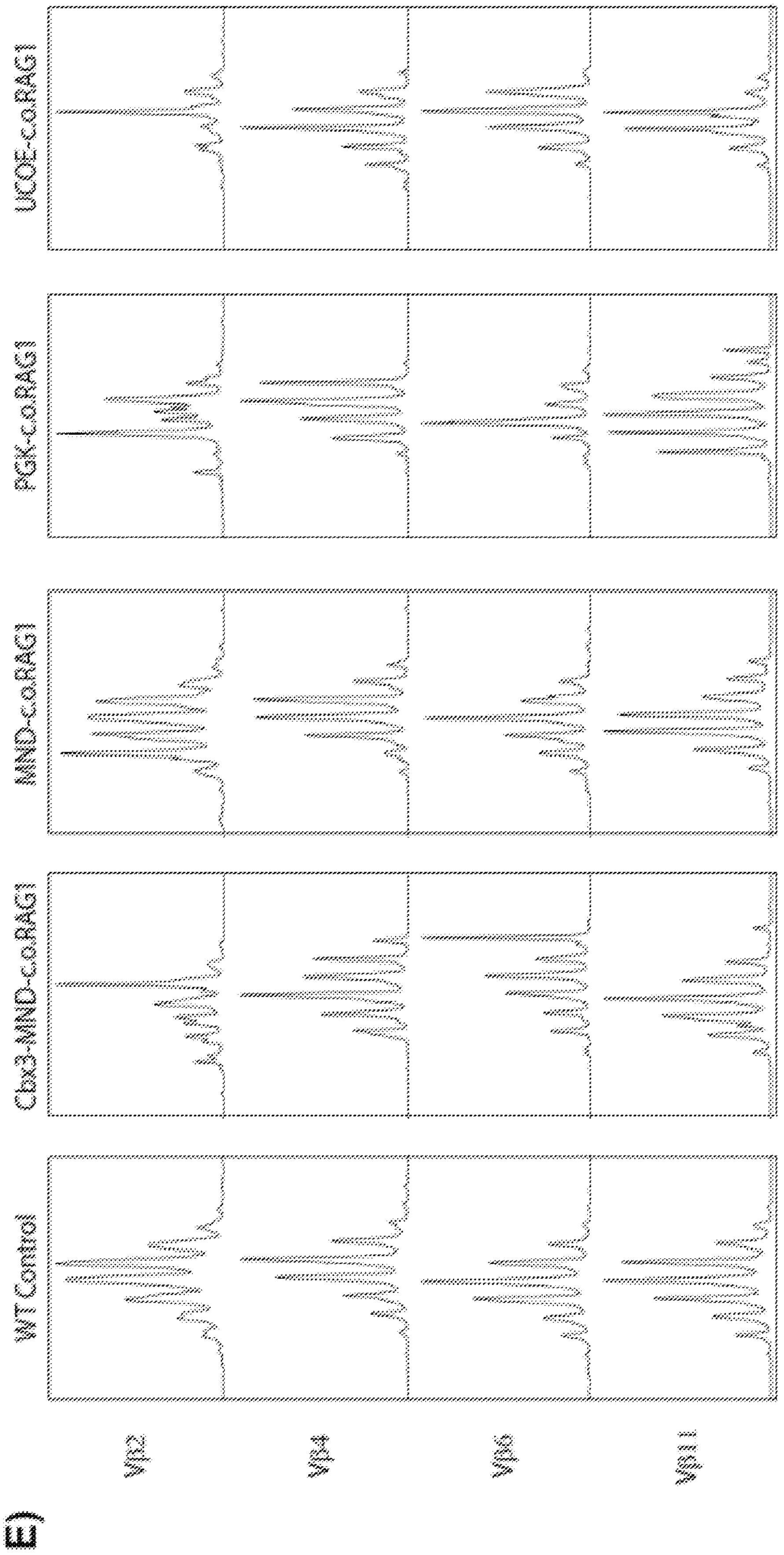

To gain better insight into the efficacy of the various promoters used, the inventors analysed the relationship between RAG1 expression and the number of B cells generated in the BM (FIG. 2A) and T cells (FIG. 2B) in the thymus, as these are the two primary lymphoid organs where RAG genes are active. For B cell development there was a clear linear correlation between RAG1 expression and B220+ cells in the BM up to ×10 fold the house keeping gene level. For T cells, the inventors observed that there was a threshold of minimal c.o.RAG1 expression, roughly at 10× the house keeping control level. Mice reconstituted with stem cells having lower c.o.RAG1 expression than this threshold did barely reconstitute thymic T cell development.

Besides efficacy, safety is an important aspect for clinical use of gene therapy vectors. As an additional selection criterion the inventors used the IVIM assay, which is the currently accepted standard for safety of viral vectors. All four vectors were shown to have a frequency of insertional mutagenic events that were at least 50 fold lower than classical RSF91 gamma-retroviral vectors (FIG. 2C) and only the UCOE vector had clearly lower replating efficiency than the other three promoters.

Finally, the inventors checked the diversity and plot clonality of the TCRβ repertoire generated in the gene therapy treated mice (FIG. 2D). the inventors used GeneScan analysis for 24 different Vb genes and calculated the cumulative complexity score. Again, as shown in the representative plots as well by the highest score, the MND promoter performed as well as wt treated mice.

The inventors therefore concluded that the pCCL-MND-c.o.RAG1 LV vector was the best vector of choice and proceeded to have the vector made GMP grade. All following experiments described are conducted with this clinical grade vector for further preclinical testing Extensive Preclinical Testing of the pCCL-MND-coRAG1 LV Vector in Rag 1 −/− Mice.

Figure 3:
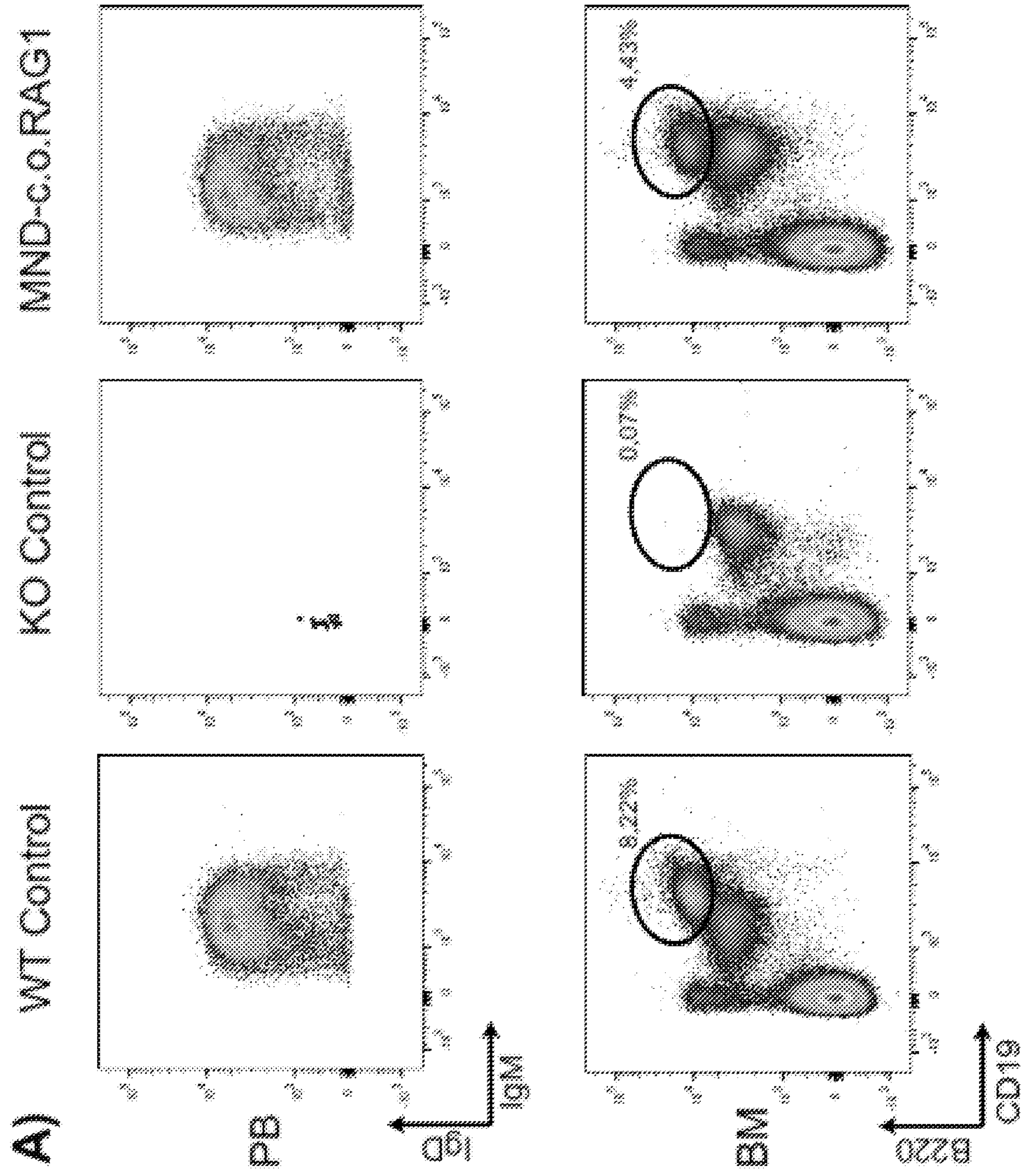
FIG. 3: Extensive immune reconstitution of mice receiving gene therapy SC with a clinical grade MND-c.o.Rag1 vector A) Representative plots of B cell reconstitution in the blood ($B220^+$IgM/IgD cells_top panel) and B cell development in the BM ($B220^+CD19^+$ cells_bottom panel) 24 weeks after transplantation. B) Total number of B cells ($B220^+CD11b/CD43^-$cells) in the PB. Mann-Whitney test (KO control vs MND-c.o.RAG1, one tailed, *p<0.05; p<0.01). C) Immature ($B220^+CD93^+$ cells; left panel) and mature ($B220^+CD93^-$cells; right panel) B cell subsets distribution in spleen. Two-way ANOVA test; *p<0.001; ****p<0.0001. D) Representative plots of T cell reconstitution in the blood ($CD3^+TCRab^+$ cells; top panels) and T cell development in the thymus (CD4 vs CD8 cells; bottom panels) 24 weeks after transplantation. E) Total number of T cells ($CD3^+TCRab^+$ cells) in PB at the end of the experiment (24 weeks). Mann-Whitney test (KO control vs MND-c.o.RAG1, one tailed; *p<0.05; **p<0.01). F) Naïve, effector and central memory subsets distribution for CD4 ($CD3^+TCRab^+CD4^+$; left panel) and CD8 ($CD3^+TCRab^+CD8^+$; right panel) T cells subsets distribution in spleen: Naïve cells ($CD44^-CD62L^+$), effector memory cells ($CD44^+CD62L^-$) and central memory cells ($CD44^+CD62L^+$) in PB 24 weeks after transplantation. G) Left panel: Hematoxylin and eosin staining of mesenteric lymph nodes (scale bar=200 μm) and spleen (scale bar=100 μm). R. Representative FoxP3 staining in spleen tissue (scale=100 μm). Representative image from one WT Control, KO Control and 1 MND-c.o.RAG1 GT. Arrows indicate positive FoxP3 in germinal centers.
Figure 3:
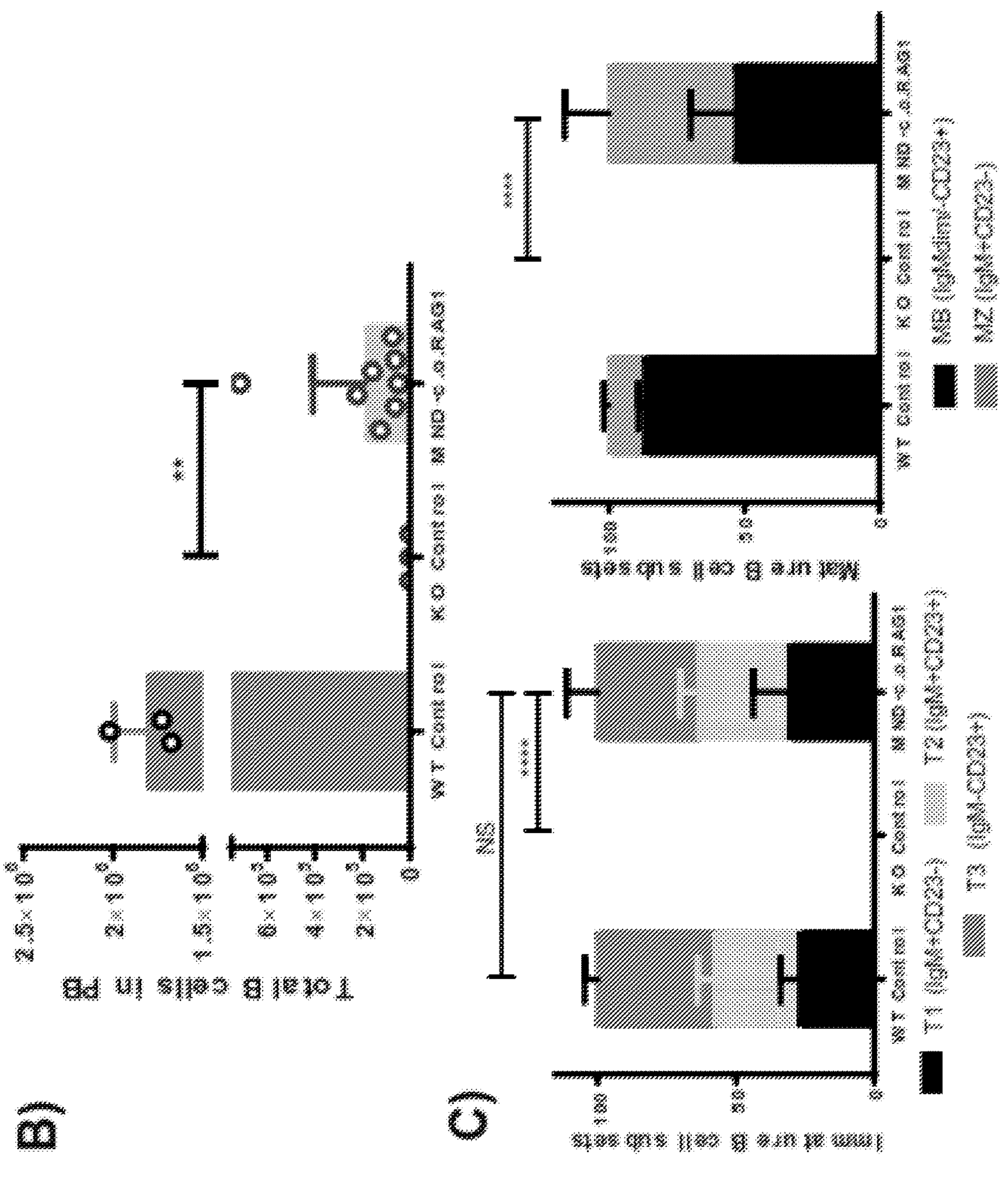
Figure 3:
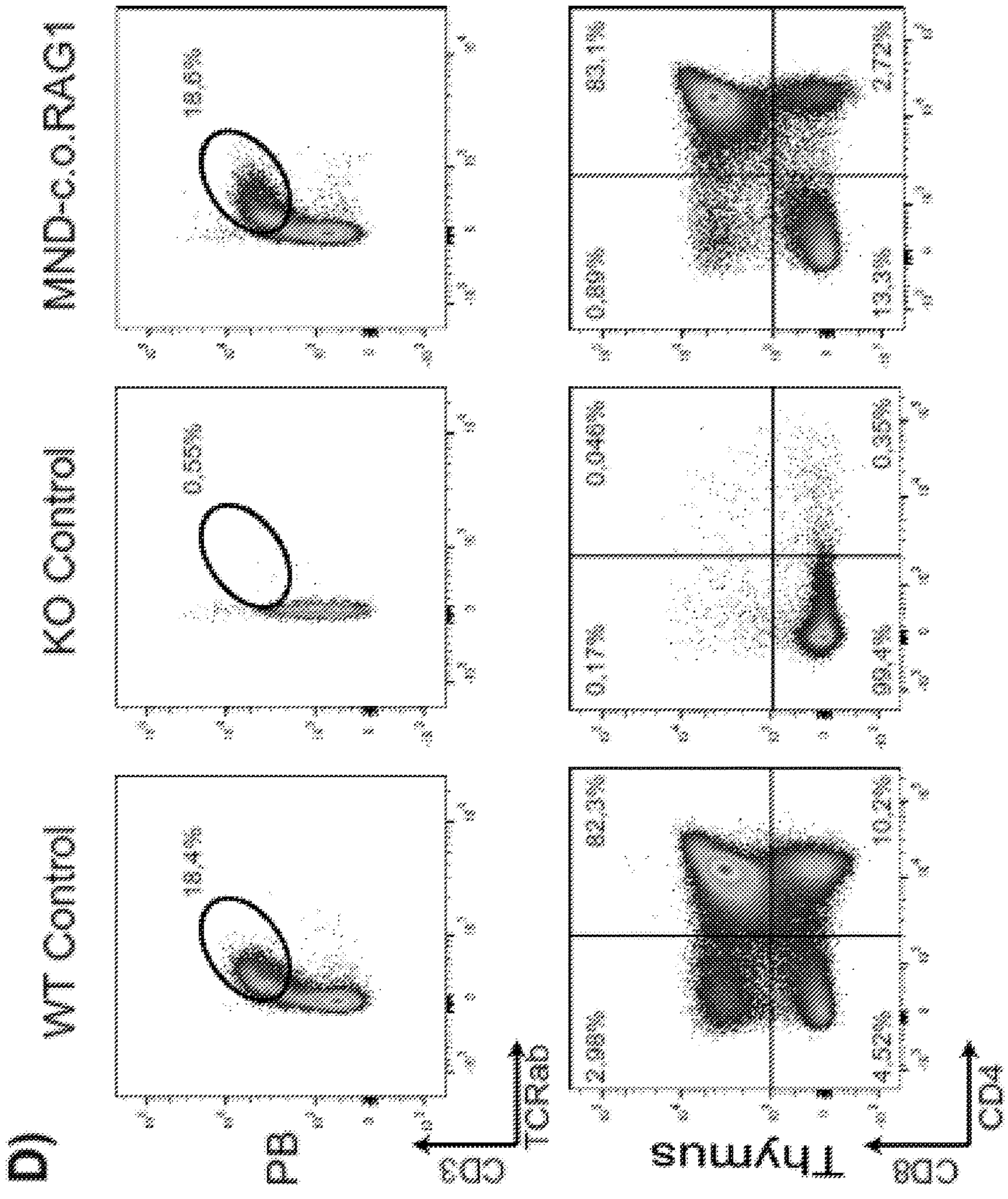
Figure 3:
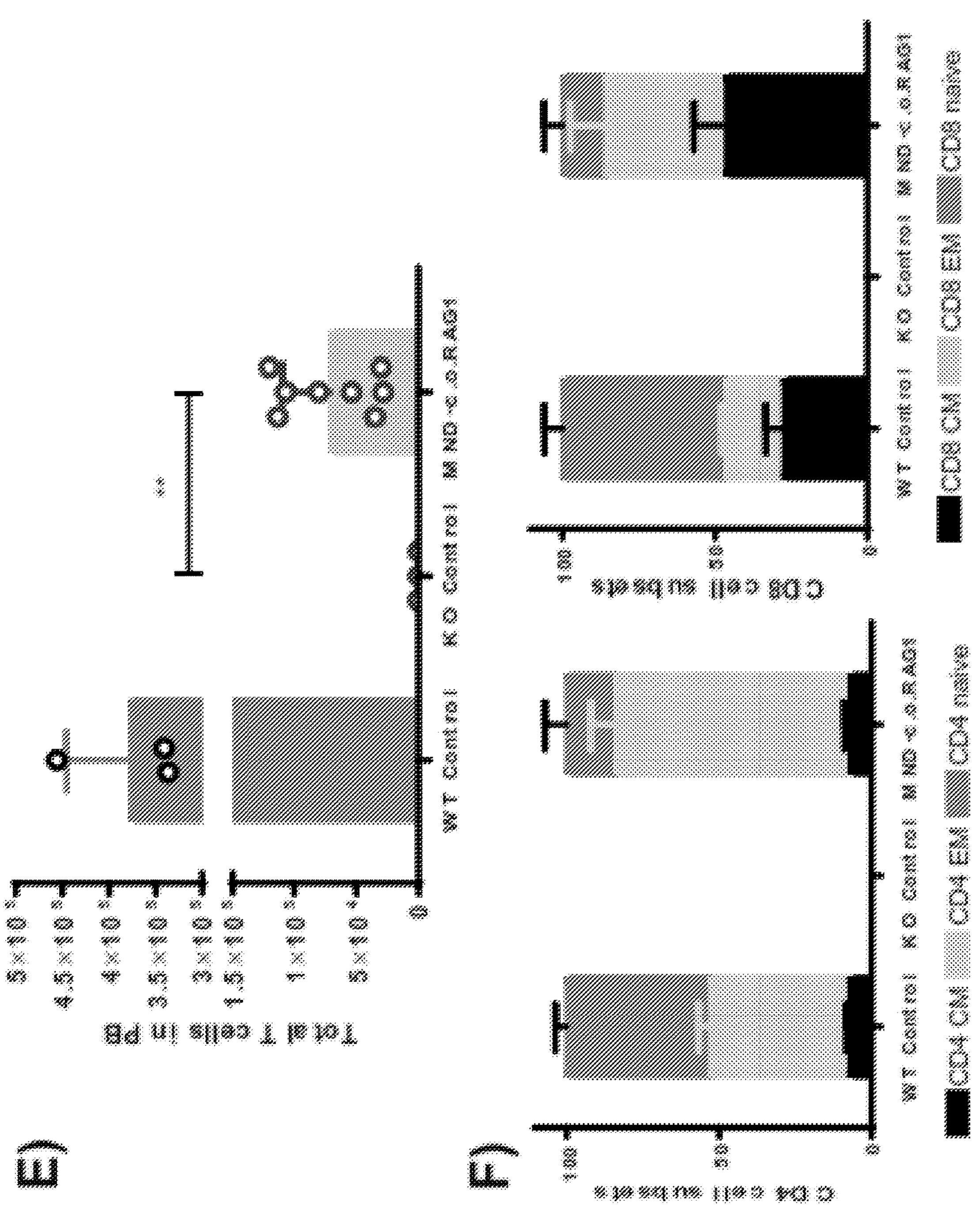
Figure 3:
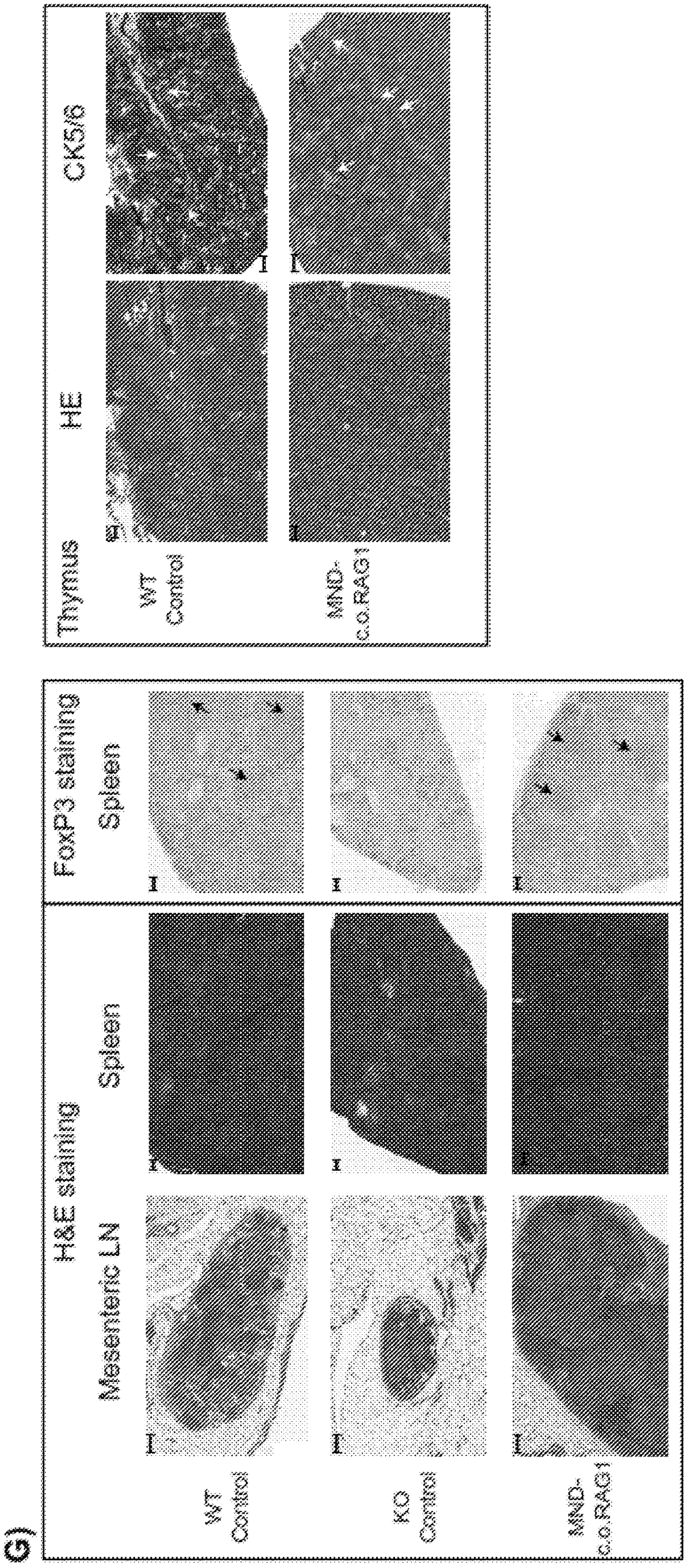

Initial analysis of 8 Rag1−/− mice treated with the MND vector, positive (wt stem cells) and negative controls (mock transduced Rag1−/− stem cells) confirmed good B cell reconstitution in the periphery (PB) and in BM (FIG. 3A), although the numbers remained lower than mice treated with wt stem cells (FIG. 3B and FIG. 7B), which could be due to partially arrested development from pre B to immature B cell stages originating from cells that were transduced with insufficient levels of c.o.RAG1 to support full Ig rearrangements (FIG. 7C). Alternatively, residual pro and pre B cells could inhibit B cell development by occupying important developmental niches. However, gene therapy mice showed same proportion of immature and mature B cell subsets in the spleen (FIG. 3.C). On the T cell site, most GT mice showed next to complete normal thymic T cell development with thymocyte numbers almost normal (FIG. 3D and FIG. 7C), although the T cell numbers in the periphery were restored to ~30% of normal levels (FIG. 3E), with somewhat lower proportion of naïve CD4 and CD8 T cells and increased effector memory subsets (FIG. 3F), most likely due to homeostatic proliferation from initial T cell that egressed from the thymus. Besides analysing the primary and secondary immunological organs by flow cytometry, the inventors also checked restoration of the immune system by histological analyses. Spleen, lymph nodes and thymus showed remarkably normal architecture after GT (FIG. 3G), comparable to mice treated with wt stem cells, and quite different from the negative control mice treated with mock transduced Rag1−/− cells. Importantly, restoration of FoxP3 expression which directs T cells into the CD4+ regulatory T cell lineage (T reg) was also observed in mice treated with MND-coRAG1 gene therapy (FIG. 3G).

Functional Reconstitution of Immunity after Rag 1 Gene Therapy

Next the inventors tested if the T and B cells that developed had a diverse repertoire and were capable of mounting an immune response against a T cell dependent neo-antigen. GeneScan analysis showed a diverse TCR Vb repertoire, that was slightly less complex before immunization than in mice reconstituted with wt stem cells (FIG. 4A), but after immunization there was no statistical difference in immune repertoire. Total IgM, IgG and IgE levels were also checked (FIG. 4B and FIG. 7E)) and reached close to normal levels in GT treated mice. The inventors used TNP-KLH as T cell specific antigen and measured the production of TNP specific IgG antibodies, thereby investigating whether the developed T and B cell could collaborate in an active immune response. The TNP-specific IgG levels in serum were similar between mice treated with wt stem cells and GT treated mice (FIG. 4C).

When checking individually TCR Vb families, it was shown that the MNDCoRAG1 construct provided a more comparable rearrangement pattern to WT control with polyclonal TCR Vb families, and with no perturbed TCR Vb usage or oligoclonal expansion (as was observed with other constructs). Importantly, with the clinical MND-c.o.RAG1 batch, the immunodiversity of the treated mice was comparable to the WT control mice, before and after immunization Importantly, while CID mouse models have a defective response to B cell dependent T-cell antigens, the inventors' TNP-KLH immunized MND-c.o.RAG1 gene therapy mice were able to successfully mount an immune response against the B cells dependent T-cell antigens at a comparable level to the control mice, suggesting that the mice treated with gene therapy do not present a CID phenotype but rather were able to overcome this immunodeficient phenotype.

Pre-Clinical Safety Tests of the Vector

As required by regulatory authorities the clinical grade vector was tested by external parties for the presence of replication competent virus (RCL). The vector tested negative in two independent tests (data not shown). Other safety tests that are commonly required included bio distribution of the vector in vivo, checking of vector insertion sites (especially on possible clonal outgrowth) and tests for insertional mutagenesis such as IVIM.

The inventors checked vector distribution on large number of perfused organs on all GT treated mice. (FIG. 5A) Perfusion was used to remove most of the blood cells, in which the leukocytes should carry the vector. As expected, given the positive selection for c.o.RAG1 transduced cells, high VCN was found in the thymus, followed by other immunological organs, spleen, bone marrow, lymph nodes and peripheral blood. All other organs had very low signals, except some rare positivity in stomach and lungs, possibly due to incomplete perfusion, or an ongoing infection in rare individual mice (FIG. 7D, Table 4).

TABLE 4 list of organs used for mice necropsy, FACs analysis and vector biodistribution

| Organs | Immune phenotyping | Pathology | Vector Biodistribution |
|---|---|---|---|
| Adrenal gland | | x | |
| Brain | | x | x |
| Cecum | | x | |
| Colon | | x | |
| Duodenum | | x | |
| Gastrocnemius | | x | x |
| Gonalds | | x | x |
| Head-Eyes | | x | |
| Heart | | x | x |
| Ileum | | x | |
| Jejunum | | x | x |
| Kidney | | x | x |
| Limb (front and back) | x | x | x |
| Liver | | x | x |
| Lung | | x | x |
| Lymph Node (iliac) | | | x |
| Lymph Node (Lumbar) | | x | |
| Lymph Node (mesenteric) | | x | |
| Lymph Node (sacral) | | x | |
| Lymph Node (submand.) | | x | |

TABLE 4-continued list of organs used for mice necropsy, FACs analysis and vector biodistribution

| Organs | Immune phenotyping | Pathology | Vector Biodistribution |
|---|---|---|---|
| Pancreas | | x | x |
| Rectum | | x | |
| Skin | | x | |
| Spinal Cord | | x | |
| Spleen | x | x | x |
| Sternum | | x | |
| Stomach | | x | x |
| Thymus | x | x | x |
| Urinary Bladder | | x | x |

Importantly, pathological examination of histology slides of 29 different organs per mouse did not show any abnormalities in mice treated with MNDCoRAG1 gene therapy. The most characteristic pathology of Omenn Syndrome (OS) and atypical SCID models is the severe phenotype with erythroderma, skin infiltrates, eosinophilia. The inventors conducted an extensive pathology of the mice treated with MNDCoRAG1 gene therapy vector, and no OS/atypical SCID features were detected. Indeed, in the FIG. 7D, the pathology from lungs and liver is shown and revealed normal phenotype like WT treated mice, without abnormal T-cell infiltrates. The inventors also checked the skin and small intestine to support that mice treated with MND-c.o.RAG1 vector do not show a phenotype of OS or atypical SCID. Altogether, clinical signs of skin diseases were absent in all groups (ulceration, crusts, redness, alopecia were not present) (FIG. 10). Besides, histological analysis of the skin in all groups confirmed that hallmarks of Omenn like syndrome such as severe alopecia, skin erythroderma, dense dermal inflammation composed of lymphocytes and eosinophils in skin are not present in the MND-c.o.RAG1 treated mice. The inventors extensively sampled the small (duodenum, jejunum and ileum) and large intestine (cecum colon and rectum); where severe inflammatory infiltrate resembling Omenn like syndrome was absent.

Next, the inventors checked viral insertion sites using nrLAM-PCR (FIG. 5B), a sensitive technique that can detect clonal insertions as discrete bands (which can then be sequenced if needed) (Gabriel et al., 2014). The inventors invariably found a smear of bands indicating polyclonal haematopoiesis with very little indication of oligoclonality, except for a few minor bands. The inventors conclude that there was no evidence of of vector-induced clonal selection. This is in line with findings by others on using SIN LV vectors in HSCs.

Safety of the clinical MND-c.o.RAG1 was also tested using the IVIM assay. The clinical vector showed no clonal outgrowth in different independent experiments, close to results from mock-transduced cells (FIG. 5C). This is better than the research grade vector presumably due to the higher purity resulting in a better functional titre leading to fewer side effects.

Restored B and T Cell Development in RAG1 SCID Patient Cells

The inventors have previously shown that transplantation of BM CD34+ cells from SCID patients in NSG mice is informative for identifying where T cell development is arrested in human SCID. This same model should also be suitable as preclinical efficacy model with patient cells. Hence the inventors purified CD34+ cells from cryopreserved BM cells from a RAG1-SCID patient. The patient was hypomorphic, with some residual B cells but no T cells. The inventors transplanted busulfan-conditioned mice with either mock transduced or MND-c.o.RAG1 transduced CD34+ cells and followed the development of T and B cells over time. Human cell engraftment was similar between mice transplanted with gene therapy treated cells and mock transduced cells, indicating that gene therapy did not affect the engraftment of human cells. As expected, B cells were observed in the mock transduced humanized mice, but much higher numbers of B cell were found with the spleen of GT treated CD34+ cells (FIG. 6A and FIG. 8B)). The B cells that were present also showed polyclonal Ig rearrangement (FIG. 8E) and produced immunoglobulins, as human IgM could be detected in the sera of the mice (FIG. 6D), with a tendency towards a more polyclonal repertoire after GT.

Remarkably, while no T cells developed in mice transplanted with mock transduced RAG1-SCID cells, the gene therapy mice showed clearly detectable T cell development (FIG. 6B and FIG. 8C). After sacrificing the mice, the inventors also checked their thymus. As the patient was hypomorphic, the inventors observed that some stages of T cell development were present, including all DN, ISP and the early CD3− DP stages (FIG. 6C). However, there were no cells that were CD3+ and no late CD3+DP thymocytes, nor any SP thymocytes, suggesting that especially the rearrangement of TCRα was affected by this RAG1 mutation. Finally, the inventors checked TCRB and TCRG rearrangements by Gene Scan analysis. Because of the very limited material, not all possible Vg and Vb genes could be analysed, but the selected gene segments showed many more in frame rearrangements in the gene therapy treated group, for TCRG, while for TCRB only in the GT group, rearrangements could be detected (FIG. 6E). nRLAM_PCR on spleen cells revealed a polyclonal pattern with no signs of clonal dominance (FIG. 6F).

Discussion

Patients with RAG1-SCID are hampered in the genetic assembly of TCRs and BCRs. Affected children typically experience a wide range of serious, life-threatening infections. Replacing the affected bone marrow with healthy, unmodified allogeneic stem cells is currently the only therapy for RAG1-SCID. Although overall survival is satisfactory in matched-donor SCT, the outcome in mismatched donor SCT, which represent the majority of cases, is significantly worse. Moreover, approximately 25% of allogeneic SCT-treated patients develop graft vs. host disease, which significantly impairs outcome in terms of morbidity, immune reconstitution, and transplant-related mortality (Gennery et al.). Additionally, transplant outcome in RAG-SCID (and other recombination-defective forms of T-B-SCID) is significantly worse than for SCID with B cells (i.e. T-B+ SCID) (Gennery et al.).

Transplantation of genetically corrected, autologous HSCs, eliminates the risks associated with allogeneic stem cell transplantation (GvHD and rejection) and would therefore provide a valuable alternative particularly for patients lacking a matched donor. Gene therapy for X-SCID with LV or RV SIN vectors has shown to be successful and to lack the xenotoxicity problems previously observed when using γ-retroviral vectors (Insertional mutagenesis combined with acquired somatic mutations causes leukemogenesis following gene therapy of SCID-X1 patients. Howe S J, Mansour M R, Schwarzwaelder K, Bartholomae C, Hubank M, Kempski H, Brugman M H, Pike-Overzet K, Chatters S J, de Ridder D, Gilmour K C, Adams S, Thornhill S I, Parsley K L, Staal F J, Gale R E, Linch D C, Bayford J, Brown L, Quaye M, Kinnon C, Ancliff P, Webb D K, Schmidt M, von Kalle C, Gaspar H B, Thrasher A J. J Clin Invest. 2008 September; 118(9):3143-50). For ADA-SCID, both RV vectors (currently marketed as approved therapy under the name Strimvelis) and LV vectors have shown excellent clinical results which are comparable to HSCT with matched donors reviewed in: Morgan, R. A., Gray, D., Lomova, A., and Kohn, D. B. (2017). Hematopoietic Stem Cell Gene Therapy: Progress and Lessons Learned. Cell stem cell 21, 574-590.

Unlike X-linked SCID and ADA-SCID, developing gene therapy for RAG-SCID has been notoriously difficult. Previous attempts (Lagresle-Peyrou et al., 2008) used gamma retroviral vectors in a preclinical Rag1$^{-/-}$ model, which carried a high risk of insertional mutagenesis. Although RAG1 gamma retroviral vectors were able to correct the deficiency more readily, SIN lentiviral vectors initially resulted in insufficient expression of the therapeutic RAG1 gene, leading to 'leaky' SCID or an Omenn-like phenotype. Here the inventors show that durable, functional immune reconstitution can be obtained at low VCN. The inventors also show that the human RAG1 deficiency can be functionally restored in patient cells, providing important additional efficacy data required for successful clinical implementation.

In our study a SIN LV vector using the MND promoter was chosen, because this fairly strong promoter is most efficacious in our preclinical models. The MND promoter has previously been used in gene therapy trials for ADA-SCID and Adrenoleukodystrophy (ALD), without any reports of insertional mutagenesis. In addition, our preclinical safety data indicate that the MND-coRAG1 vector is relatively safe. The inventors have found that SIN LV vector using the MND-coRAG1 is capable of restoring immunity without any gross abnormalities or histologic pathologies and therefore this vector has the ability to correct a wide range of RAG1 mediated diseases.

Clinical trials have shown that ADA-SCID and X-linked SCID gene therapies result in significant clinical benefit, as well as a significant reduction in healthcare-related costs. The inventors expect similar benefits from our approach to treat patients with RAG1-SCID, as it will reduce the suboptimal outcomes in (mismatched) allogeneic transplants, which are often associated with the need to administer immunoglobulins, and treat infectious and GvHD-related complications).

Material and Methods

Mice

C57BL/6 Rag1$^{-/-}$ mice were originally obtained from The Jackson Laboratory (USA). C57BL/6 wild-type mice and NOD.Cg-Prkdc$^{scid}$ Il2 rg$^{tm1wjl}$/SzJ (NSG) mice were purchased from Charles River (France). Mice were bred and maintained in the animal facility of Leiden University Medical Center (LUMC). All animal experiments were approved by the Dutch Central Commission for Animal experimentation (Centrale Commissie Dierproeven, CCD).

Lentiviral Vectors and Vector Production

The RAG1 gene sequence was optimized as described by Pike-Overzet et al (2011) resulting in 90% of the codons being adapted to the codon bias of *Homo sapiens* genes. Furthermore, the GC-content was raised from 48 to 61% and the number of cis-acting motifs was reduced from 21 to 0. The optimized RAG1 sequence was synthesized by GeneArt (Regensburg, Germany). Codon optimized RAG1 (c.o.RAG1) was cloned into self-inactivating lentiviral pCCL plasmid resulting in Cbx3.MND.coRAG1 (hereafter: Cbx3-c.o. RAG1), pCCL-MND-c.o.RAG1 (hereafter: MND-c.o.RAG1), pCCL-PG K-c.o.RAG1 (hereafter: PGK-c.o.RAG1) and pCCL-UCOE-c.o.RAG1 (hereafter: UCOE-c.o.RAG1). DNA sequencing of the transgene was performed to validate the gene transfer constructs. Helper plasmids pMDLg/pRRE, pRSV-Rev and pMD2.VSVG for lentiviral production were kindly provided by L. Naldini (San Raffaele Telethon Institute for Gene Therapy, Milan, Italy) (Dull et al., 1998). Large-scale helper-plasmid preparations were obtained through PlasmidFactory (Bielefeld, Germany).

293T cells were transiently transfected with the transfer and helper plasmids using X-tremeGene HP DNA transfection reagent (Sigma-Aldrich). Lentivirus was harvested 24 h, 30 h and 48 h after transfection, filtered through 0.22 μm pore filters (Whatmann) and stored at −80° C. Pooled lentiviral supernatant was concentrated by ultracentrifugation (Beckman Optima™ LE-80K, rotor SW32Ti) for 16 hours at 10.000 rpm and 4° C. under vacuum. Pellets were resuspended in StemSpan Serum-Free expansion medium (SFEM; Stemcell Technologies Inc) and aliquoted to avoid multiple freeze/thaw cycles. Since no suitable anti-RAG1 antibodies were available, the inventors determined the viral titer using qPCR as described later on. A clinical GMP-grade vector was generated by Batavia Biosciences (Leiden, The Netherlands) tested and validated on murine Rag1 deficient bone marrow cells, human CD34$^+$ cells, aliquoted in 200 ml vials and stored at −80 degrees until use.

Transduction of Murine Lineage Negative Bone Marrow Cells and Human CD34+ Cells Murine bone marrow (BM) cells were obtained from femurs and tibias of C57BL/6 wild-type and C57BL/6 Rag1$^{-/-}$ mice. The obtained bones were flushed or crushed, cells were passed through a 0.7 μm cell strainer (Falcon), washed and viable frozen. After thawing, lineage negative cells were isolated using mouse lineage depletion kit and AUTOMacs cell sorter (Miltenyi Biotech). Lineage negative cells were stimulated overnight in StemSpam-SFEM containing Penicilin/Steptamycin (5,000 units/5,000 ug/ml; Gibco) and supplemented with 50 ng/mL recombinant mouse FMS-related tyrosine kinase 3 ligand (rmFLT3L; R&D systems), 100 ng/mL recombinant mouse Stem-Cell Factor (rmSCF; R&D systems) and 10 ng/mL recombinant mouse thrombopoietin (rmTPO; R&D systems). Rag1$^{-/-}$ cells were subsequently transduced with the different lentiviruses using 4 ug/ml proteamine sulphate (Sigma-Aldrich) and by way of spin-occulation at 800×g and 32° C. for 1 hour. Cells were cultured at 37° C., 5% $CO_2$ for 24 h in medium supplemented with cytokines.

Human bone marrow from children diagnosed with SCID was obtained according to the Medical Ethical Committee and IRB guidelines at Leiden University Medical Center The patient was a compound heterozygote was the following confirmed mutations: RAG1 allele 1 C 256-257 deletion AA, allele 2 C 1677 G>T Mononuclear cells were separated by Ficoll gradient centrifugation, frozen in fetal calf serum (Grenier Bio-one)/10% DMSO (Sigma-Aldrich) and stored in liquid nitrogen. After thawing, human CD34$^+$ cells were isolated using CD34 MicroBead UltraPure Kit (Milteny Biotec). Enriched CD34$^+$ cells were stimulated overnight in X-VIV015 without Gentamycin and phenolred (Lonza)—1% human albumin (200 g/L; Sanquin)—Pen/Strep medium supplemented with 300 ng/ml huSCF (Milteny Biotec), 100 ng/ml huTPO (Milteny Biotec), 300 ng/ml huFlt3L (Milteny Biotec) and 10 ng/ml huIL3 (Milteny Biotec). Cells were transduced in X-VIVO-15 complete medium with 4 ug/mL proteamine sulphate as described previously and cultured for 24 h.

Transplantation of $Rag1^{-/-}$ and NSG Mice

Control mock-transduced cells (C57BL/6 wild-type cells referred as WT control and $Rag1^{-/-}$ cells referred as KO control) and transduced $Rag1^{-/-}$ murine cells (up to $5 \cdot 10^5$ cells/mouse) were mixed with supportive $Rag1^{-/-}$ spleen cells ($3 \cdot 10^6$ cells/mouse) in Iscove's Modified Dulbecco's Medium (IMDM) without phenol red (Gibco) and transplanted by tail vein injection into pre-conditioned $Rag1^{-/-}$ recipient mice. Recipient mice (8-12 week old mice) were conditioned with a total body single dose irradiation 24 h prior the transplantation using orthovoltage X-rays (8.08 Gy) or with two consecutive doses of 25 mg/kg Busulfan (Sigma-Aldrich) (48 h and 24 h prior transplantation). After overnight culture, 60.000 to 70.000 human CD34+ cells were resuspended in (IMDM) without phenol red (Gibco) and transplanted intravenously into busulfan pre-conditioned NSG recipient mice (5 week old mice, busulfan conditioning as described). Mice used for transplantation were kept in a specified pathogen-free section. The first four weeks after transplantation mice were fed with additional DietGel recovery food (Clear H2O) and antibiotic water containing 0.07 mg/mL Polymixin B (Bupha Uitgeest), 0.0875 mg/mL Ciprofloxacin (Bayer b.v.) and 0.1 mg/mL Amfotericine B (Bristol-Myers Squibb) and their welfare was monitored daily. Peripheral blood (PB) from the mice was drawn by tail vein incision every 4 weeks until the end of the experiment. PB, thymus, spleen and BM were obtained from $CO_2$ euthanized mice.

Immunization

Mice were immunized with synthetic TNP-KLH antigen 4 weeks before the end of the experiment. 100 ug TNP-KLH (Biosearch Technologies Inc.) in 50% Imject Alum (Thermo Scientific) was injected intraperitoneal (i.p.). 3 weeks later, mice were boosted i.p. with 100 ug TNP-KLH in PBS. Serum was collected before and 1 week after the boost injection.

Flow Cytometry

Single cell suspensions from thymus and spleen were prepared by squeezing the organs through a 70 μM cell strainer (BD Falcon) and single cell suspension from BM was made as described previously. Erythrocytes from PB and spleen were lysed using $NH_4Cl$ (8.4 g/L)/$KHCO_3$ (1 g/L) solution. Single cell suspensions were counted and stained with the antibodies listed in Table 1.

Briefly, cells were incubated for 30 min at 4° C. in the dark with the antibody-mix solution including directly conjugated antibodies at the optimal working solution in FACS buffer (PBS pH7.4, 0.1% azide, 0.2% BSA). After washing with FACS buffer, a second 30 min incubation step at 4° C. was performed with the streptavidin-conjugated antibody solution. When necessary, 7AAD (BD Biosciences) was used as viability dye. Cells were measured on FACS-Cantoll and LSR Fortessa X-20 (BD Biosciences) and the data was analysed using FlowJO software (Tree Star).

Determination Vector Copy Number (VCN) and c.o.Rag1 Expression by RT-qPCR qPCR was used for the quantitative analysis of genomic lentiviral RNA, proviral DNA copies and transgene mRNA expression using WPRE, c.o.RAG1, ABL1 and PTBP2 as targets. Total RNA from single cell suspensions was purified using RNeasy Mini kit (Qiagen) and reverse transcribed into cDNA using Superscript III kit (Invitrogen). Genomic DNA was extracted from single cell suspensions using the GeneElute Mammalian Genomic DNA kit (Sigma-Aldrich). Dneasy Blood and Tissue Kit (Qiagen) was used to isolate genomic DNA from murine organs and tissues. VCN was determined on DNA samples by the detection of WPRE and PTBP2. The levels of transgene expression were determined on cDNA samples, by normalizing c.o.RAG1 to the expression of the ABL1 gene. qPCR was performed using TaqMan Universal Master Mix II (Thermofisher) in combination with specific probes for indicated genes from Universal Probe Library (Roche). Primers and probes used are listed in Table 5 and 5. PCR reactions were performed on the StepOnePlus Real-Time PCR system (Thermofisher). All samples were run in triplicate.

TABLE 5

List of primers and probes used to determine VCN and c.o.RAG1 expression

| Description | Orientation | DNA sequence 5'-3' |
|---|---|---|
| ABL1 | FW | 5'-TGGAGATAACACTCTAAGCATAACTAAAGGT-3' (SEQ ID NO: 6) |
| | RV | 5'-GATGTAGTTGCTTGGGACCCA-3' (SEQ ID NO: 7) |
| | Probe | 5'FAM-CCATTTTTGGTTTGGGCTTCACACCATT- TAMRA 3' (SEQ ID NO: 8) |
| c.o.Rag1 | FW | 5' CAACTGCAAGCACGTGTTCTG 3' (SEQ ID NO: 9) |
| | RV | 5' GCAGTAGCTGCCCATCACTTT 3' (SEQ ID NO: 10) |
| | Probe | 5'FAM AGAGTGTGCATCCTGCGGTGCCT TAMRA 3' (SEQ ID NO: 11) |
| PTBP2 | FW | 5'-TCTCCATTCCCTATGTTCATGC-3' (SEQ ID NO: 12) |
| | RV | 5'-GTTCCCGCAGAATGGTGAGGTG-3' (SEQ ID NO: 13) |
| | Probe | [JOE]-ATGTTCCTCGGACCAACTTG-[BHQ1] (SEQ ID NO: 14) |
| WPRE | FW | 5'-GAGGAGTTGTGGCCCGTTGT-3' (SEQ ID NO: 15) |
| | RV | 5'-TGACAGGTGGTGGCAATGCC-3' (SEQ ID NO: 16) |
| | Probe | [6FAM]-CTGTGTTTGCTGACGCAAC-[BHQ1] (SEQ ID NO: 17) |

TABLE 6

List of primers and probes used in repertoire analysis (murine)

| Description | Orientation | DNA sequence |
|---|---|---|
| V gene segment-specific oligonucleotide | | (5'->3', coding strand) |
| mVβ1 | FW | CTGAATGCCCAGACAGCTCCAAGC (SEQ ID NO: 18) |
| mVβ2 | FW | TCACTGATACGGAGCTGAGGC (SEQ ID NO: 19) |
| mVβ3.1 | FW | CCTTGCAGCCTAGAAATTCAGT (SEQ ID NO: 20) |
| mVβ4 | FW | GCCTCAAGTCGCTTCCAACCTC (SEQ ID NO: 21) |
| mVβ5.1 | FW | CATTATGATAAAATGGAGAGAGAT (SEQ ID NO: 22) |
| mVβ5.2 | FW | AAGGTGGAGAGAGACAAAGGATTC (SEQ ID NO: 23) |
| mVβ5.3# | FW | AGAAAGGAAACCTGCCTGGTT (SEQ ID NO: 24) |
| mVβ6 | FW | CTCTCACTGTGACATCTGCCC (SEQ ID NO: 25) |
| mVβ7 | FW | TACAGGGTCTCACGGAAGAAGC (SEQ ID NO: 26) |
| mVβ8.1 | FW | CATTACTCATATGTCGCTGAC (SEQ ID NO: 27) |
| mVβ8.2 | FW | CATTATTCATATGGTGCTGGC (SEQ ID NO: 28) |
| mVβ8.3 | FW | TGCTGGCAACCTTCGAATAGGA (SEQ ID NO: 29) |
| mVβ9 | FW | TCTCTCTACATTGGCTCTGCAGGC (SEQ ID NO: 30) |
| mVβ10 | FW | ATCAAGTCTGTAGAGCCGGAGGA (SEQ ID NO: 31) |
| mVβ11 | FW | GCACTCAACTCTGAAGATCCAGAGC (SEQ ID NO: 32) |
| mVβ12 | FW | GATGGTGGGGCTTTCAAGGATC (SEQ ID NO: 33) |
| mVβ13 | FW | AGGCCTAAAGGAACTAACTCCCAC (SEQ ID NO: 34) |
| mVβ14 | FW | ACGACCAATTCATCCTAAGCAC (SEQ ID NO: 35) |
| mVβ15 | FW | CCCATCAGTCATCCCAACTTATCC (SEQ ID NO: 36) |
| mVβ16 | FW | CACTCTGAAAATCCAACCCAC (SEQ ID NO: 37) |
| mVβ17# | FW | AGTGTTCCTCGAACTCACAG (SEQ ID NO: 38) |
| mVβ18 | FW | CAGCCGGCCAAACCTAACATTCTC (SEQ ID NO: 39) |
| mVβ19# | FW | CTGCTAAGAAACCATGTACCA (SEQ ID NO: 40) |
| mVβ20 | FW | TCTGCAGCCTGGGAATCAGAA (SEQ ID NO: 41) |
| C gene segment specific oligonucleotide | | (5'->3', non-coding strand) |
| muTCB1-FAM | RV | FAM-CTTGGGTGGAGTCACATTTCTC (SEQ ID NO: 42) |

Serum Immunoglobulin Quantification

Murine IgG, IgM, IgE, TNP-specific IgG and human IgM were determined by a sandwich enzyme-linked immunosorbent assay (ELISA). NUNC Maxisop plates (Thermo Scientific) were coated with unlabeled anti-mouse IgG, IgM (11E10), IgE antibodies (SouthernBiotech) or unlabeled anti-human IgM antibody (Jackson Immuno Research laboratories, kindly provided by Dr. Karahan, LUMC). For detection of TNP-specific IgG, plates were coated with synthetic TNP-KLH (Biosearch Technologies Inc.). Blocking was done with 1% BSA/PBS (mouse) or 2% BSA/0.025Tween/PBS (human) for 1 h at room temperature (RT) and subsequently serial dilutions of the obtained sera were incubated for 3 h at RT. After washing, plates were incubated with biotin-conjugated anti-mouse IgG, IgM, IgE (SouthernBiotec) or anti-human IgM (Novex life technologies, kindly provided by Dr. Karahan, LUMC) for 30 min at RT. For detection, plates were incubated for 30 min at RT with streptavidin horseradish peroxidase (Jackson Immuno Research laboratories) and subsequently azino-bis-ethylbenzthiazoline sulfonic acid (ABTS, Sigma-Aldrich) was used as a substrate. Data was acquired at a wavelength of 415 nm using Bio-Rad iMark microplate reader and MPM 6 software (Bio-Rad). Antibody concentration was calculated by using purified IgG, IgM, IgE proteins (SouthernBiotech) and human reference serum (Bethyl Laboratories, kindly provided by Dr. Karahan, LUMC) as standards.

Repertoire Analysis

Total RNA was purified from murine spleen cells and reverse transcribed into cDNA as described previously. GeneScan analysis procedure of the murine T-cell repertoire was adapted from (Pannetier et al., 1993). cDNA was amplified using a FAM-labeled C gene segment-specific primer along with 24 TCR Vβ-specific primers (See Table 6. GeneScan™ 500 ROX™ (ThermoFisher) was used as internal size standard. Labeled PCR products were run on the ABI Prism® Genetic Analyzer (Applied Biosystems) for fragment analysis. Raw spectratrype data was analyzed, visualized and scored by ScoreSpec, a novel spectratype analysis algorithm for estimating immunodiversity (Cordes et al, manuscript in preparation). ScoreSpec identifies and scores individual spectratype peak patterns for overall (Gaussian) peak distribution; shape of individual peaks, while correcting for out-of-frame TCR transcripts. Scores range from 0 when no peaks detected, to 100 for a diverse TCR repertoire.

Human immunoglobulin and T-cell receptor repertoire generated in NSG mice was analyzed on DNA samples from BM and thymus (DNA was extracted as described previously). Rearrangements were analyzed using the EuroClonality/BOMED-2 multiplex PCR protocol (van Dongen et al., 2003). Amplification of IgH, IgK, TCRβ and TCRγ rearrangements were performed following the IGH+IGK B-Cell Clonality Assay (InvivoScribe) and TCRB+TCRG T-Cell Clonality Assay (InvivoScribe) instructions respectively. PCR products were analyzed by differential fluorescence detection using ABI-3730 instrument (Applied Biosystems) for fragment analysis. The output files were visualized and analyzed using ScoreSpec.

Non-Restrictive Linear Amplification Mediated PCR (nr-LAM-PCR)

Lentiviral insertion site was analysed by nrLAM-PCR on murine bone marrow DNA samples as described by (Gabriel et al., 2014); Schmidt M. et al (2014) J. Vis. Exp. (88), e51543.

In Vitro Immortalization Assay (IVIM)

Genotoxic potential of the viral vectors (Cbx3-c.o.RAG1, MND-c.o.RAG1, PGK-c.o.RAG1, UCOE-c.o.RAG1) was quantified as previously described by (Modlich et al., 2006) Baum et al. (2006) Blood 108:2545-2553.

Gross Pathology and Histopathology

A full necropsy was performed, organs were collected subjected to macroscopic and microscopic examination (list X of collected organs). The selection of organs to be examined for gross pathology and histopathology analyses followed the applicable European and international guidelines (EMEA 1995, WHO 2005) (WHO, 2005). For gross pathology, the external surface of the body, orifices, the thoracic abdominal and cavities were examined (Analyzed organs are listed in Table 4).

For histopathological examination organs were fixed in 4% neutral buffered formalin for 24 hours and paraffin embedded, 5 μm sections were processed for hematoxylin and eosin (HE) and for immunohistochemistry stainings according to standard procedures (Bancroft and Gamble, 2008). All slides were examined blindly by a European board certified pathologist (ECVP).

Statistics

Statistics were calculated and graphs were generated using GraphPad Prism6 (GraphPad Software). Statistical significance was determined by standard one-tailed Mann-Whitney U test or ANOVA test (*p<0.05, p<0.01, *p<0.001 and ****p<0.0001).

```
SEQUENCES
SEQ ID NO: 1:
RAG1 human protein sequence (1043 aa)
MAASFPPTLGLSSAPDEIQHPHIKFSEWKFKLFRVRSFEKTPEEAQKEKKDSFEGKPSLEQSPAVLDKAD

GQKPVPTQPLLKAHPKFSKKFHDNEKARGKAIHQANLRHLCRICGNSFRADEHNRRYPVHGPVDGKTLGL

LRKKEKRATSWPDLIAKVFRIDVKADVDSIHPTEFCHNCWSIMHRKFSSAPCEVYFPRNVTMEWHPHTPS

CDICNTARRGLKRKSLQPNLQLSKKLKTVLDQARQARQHKRRAQARISSKDVMKKIANCSKIHLSTKLLA

VDFPEHFVKSISCQICEHILADPVETNCKHVFCRVCILRCLKVMGSYCPSCRYPCFPTDLESPVKSFLSV

LNSLMVKCPAKECNEEVSLEKYNHHISSHKESKEIFVHINKGGRPRQHLLSLTRRAQKHRLRELKLQVKA

FADKEEGGDVKSVCMTLFLLALRARNEHRQADELEAIMQGKGSGLQPAVCLAIRVNTFLSCSQYHKMYRT

VKAITGRQIFQPLHALRNAEKVLLPGYHHFEWQPPLKNVSSSTDVGIIDGLSGLSSSVDDYPVDTIAKRF

RYDSALVSALMDMEEDILEGMRSQDLDDYLNGPFTVVVKESCDGMGDVSEKHGSGPVVPEKAVRFSFTIM

KITIAHSSQNVKVFEEAKPNSELCCKPLCLMLADESDHETLTAILSPLIAEREAMKSSELMLELGGILRT

FKFIFRGTGYDEKLVREVEGLEASGSVYICTLCDATRLEASQNLVFHSITRSHAENLERYEVWRSNPYHE

SVEELRDRVKGVSAKPFIETVPSIDALHCDIGNAAEFYKIFQLEIGEVYKNPNASKEERKRWQATLDKHL

RKKMNLKPIMRMNGNFARKLMTKETVDAVCELIPSEERHEALRELMDLYLKMKPVWRSSCPAKECPESLC
```

QYSFNSQRFAELLSTKFKYRYEGKITNYFHKTLAHVPEIIERDGSIGAWASEGNESGNKLFRRFRKMNAR

QSKCYEMEDVLKHHWLYTSKYLQKFMNAHNALKTSGFTMNPQASLGDPLGIEDSLESQDSMEF

SEQ ID NO: 2:
codon optimised nucleic acid sequence encoding human RAG1 catalytic domain
caagggcggcagaccccggcagcacctgctgtccctgaccagacgggcccagaagcaccggctgcgggagctgaagctcc aggtcaaggccttcgccgacaaagaggaaggcggcgacgtcaagagcgtgtgcatgaccctgtttctgctggccctgcgggcc aggaacgagcaccggcaggccgatgagctggaagccatcatgcagggcaagggcagcggcctccagcctgccgtgtgcct ggccatccgggtgaacacctttctgagctgtagccagtaccacaagatgtaccggaccgtgaaggccatcaccggcagacag atcttccagcctctgcacgccctgcggaacgccgagaaggtgctgctgcccggctaccaccacttcgagtggcagcccccctg aagaacgtgagcagcagcaccgacgtgggcatcatcgacggcctgagcggcctgtccagcagcgtggacgactaccctgtg gacaccatcgccaagcggttcagatacgacagcgccctggtgtccgccctgatggacatggaagaggacatcctggaaggca tgcggagccaggacctggacgattacctgaacggccccttcaccgtggtggtgaaagagtcctgcgacggcatgggcgacgtg agcgagaagcacggcagcggccctgtggtgcccgagaaggccgtgcggttcagcttcaccatcatgaagatcaccatcgccc acagcagccagaacgtgaaggtgttcgaggaagccaagcccaacagcgagctgtgctgcaagcccctgtgcctgatgctggc cgacgagagcgaccacgagaccctgaccgccatcctgagccccctgatcgccgagcgggaggccatgaagagcagcgaa ctgatgctggaactgggcggcatcctgaggaccttcaagttcatcttccggggcaccggctacgacgagaagctggtccgggag gtggagggcctggaagccagcggcagcgtgtacatctgcaccctgtgcgacgccacccggctggaagcc SEQ ID NO: 3:
RAG1 cDNA sequence
atggcagcctctttcccacccaccttgggactcagttctgccccagatgaaattcagcacccacatattaaattttcagaatggaaa tttaagctgttccgggtgagatcctttgaaaagacacctgaagaagctcaaaaggaaaagaaggattcctttgaggggaaaccc tctctggagcaatctccagcagtcctggacaaggctgatggtcagaagccagtcccaactcagccattgttaaaagcccacccta agttttcaaagaaatttcacgacaacgagaaagcaagaggcaaagcgatccatcaagccaaccttcgacatctctgccgcatct gtgggaattcttttagagctgatgagcacaacaggagatatccagtccatggtcctgtggatggtaaaaccctaggccttttacga aagaaggaaaagagagctacttcctggccggacctcattgccaaggttttccggatcgatgtgaaggcagatgttgactcgatcc accccactgagttctgccataactgctggagcatcatgcacaggaagtttagcagtgccccatgtgaggtttacttcccgaggaac gtgaccatggagtggcacccccacacaccatcctgtgacatctgcaacactgcccgtcggggactcaagaggaagagtcttca gccaaacttgcagctcagcaaaaaactcaaaactgtgcttgaccaagcaagacaagcccgtcagcgcaagagaagagctca ggcaaggatcagcagcaaggatgtcatgaagaagatcgccaactgcagtaagatacatcttagtaccaagctccttgcagtgg acttcccagagcactttgtgaaatccatctcctgccagatctgtgaacacattctggctgaccctgtggagaccaactgtaagcatg tcttttgccgggtctgcattctcagatgcctcaaagtcatgggcagctattgtccctcttgccgatatccatgcttccctactgacctgga gagtccagtgaagtcctttctgagcgtcttgaattccctgatggtgaaatgtccagcaaaagagtgcaatgaggaggtcagtttgg aaaaatataatcaccacatctcaagtcacaaggaatcaaaagagatttttgtgcacattaataaagggggccggccccgccaa catcttctgtcgctgactcggagagctcagaagcaccggctgagggagctcaagctgcaagtcaaagcctttgctgacaaaga agaaggtggagatgtgaagtccgtgtgcatgaccttgttcctgctggctctgagggcgaggaatgagcacaggcaagctgatga gctggaggccatcatgcagggaaagggctctggcctgcagccagctgtttgcttggccatccgtgtcaacaccttcctcagctgca gtcagtaccacaagatgtacaggactgtgaaagccatcacagggagacagatttttcagcctttgcatgcccttcggaatgctga gaaggtacttctgccaggctaccaccactttgagtggcagccacctctgaagaatgtgtcttccagcactgatgttggcattattgat gggctgtctggactatcatcctctgtggatgattacccagtggacaccattgcaaagaggttccgctatgattcagctttggtgtctgc tttgatggacatggaagaagacatcttggaaggcatgagatcccaagaccttgatgattacctgaatggccccttcactgtggtgg tgaaggagtcttgtgatggaatgggagacgtgagtgagaagcatgggagtgggcctgtagttccagaaaaggcagtccgtttttc attcacaatcatgaaaattactattgcccacagctctcagaatgtgaaagtatttgaagaagccaaacctaactctgaactgtgttg -continued caagccattgtgccttatgctggcagatgagtctgaccacgagacgctgactgccatcctgagtcctctcattgctgagagggagg ccatgaagagcagtgaattaatgcttgagctgggaggcattctccggactttcaagttcatcttcaggggcaccggctatgatgaa aaacttgtgcgggaagtggaaggcctcgaggcttctggctcagtctacatttgtactctttgtgatgccacccgtctggaagcctctc aaaatcttgtcttccactctataaccagaagccatgctgagaacctggaacgttatgaggtctggcgttccaacccttaccatgagt ctgtggaagaactgcgggatcgggtgaaaggggtctcagctaaacctttcattgagacagtcccttccatagatgcactccactgt gacattggcaatgcagctgagttctacaagatcttccagctagagataggggaagtgtataagaatcccaatgcttccaaagag gaaaggaaaaggtggcaggccacactggacaagcatctccggaagaagatgaacctcaaaccaatcatgaggatgaatgg caactttgccaggaagctcatgaccaaagagactgtggatgcagtttgtgagttaattccttccgaggagaggcacgaggctctg agggagctgatggatctttacctgaagatgaaaccagtatggcgatcatcatgccctgctaaagagtgcccagaatccctctgcc agtacagtttcaattcacagcgttttgctgagctcctttctacgaagttcaagtataggtatgagggaaaaatcaccaattattttcac aaaaccctggcccatgttcctgaaattattgagagggatggctccattggggcatgggcaagtgagggaaatgagtctggtaac aaactgtttaggcgcttccggaaaatgaatgccaggcagtccaaatgctatgagatggaagatgtcctgaaacaccactggttgt acacctccaaatacctccagaagtttatgaatgctcataatgcattaaaaacctctgggtttaccatgaaccctcaggcaagcttag gggacccattaggcatagaggactctctggaaagccaagattcaatggaattttaa SEQ ID NO: 4:
codon optimised RAG1 DNA sequence
atggccgccagcttccccccctaccctgggcctgagcagcgcccctgacgagatccagcacccccacatcaagttcagcgagtg gaagttcaagctgttcagagtgcggagcttcgagaaaacccccgaggaagcccagaaagagaagaaggacagcttcgagg gcaagcccagcctggaacagagccctgccgtgctggacaaggccgacggccagaaacccgtgcccacccagcccctgctg aaggcccaccccaagttcagcaagaagttccacgacaacgagaaggccaggggcaaggccatccaccaggccaacctgc ggcacctgtgccggatctgcggcaacagcttccgggccgacgagcacaaccggcgctaccccgtgcacggccccgtggacg gcaagacactgggcctgctgcggaagaaagagaaacgggccacctcctggcccgacctgatcgccaaggtgttccggatcg acgtgaaggccgacgtggacagcatccaccccaccgagttctgccacaactgctggtccatcatgcaccggaagttcagctcc gccccctgcgaggtgtacttcccccggaacgtgaccatggaatggcaccctcacacccccagctgcgacatctgcaacaccgc cagacggggcctgaagcggaagagcctccagcccaacctccagctgtccaagaaactgaaaaccgtgctggatcaggccc ggcaggccaggcagcggaagcggagagcccaggcccggatcagcagcaaggacgtgatgaagaagatcgccaactgta gcaagatccacctgagcaccaagctgctggccgtggacttccccgagcacttcgtgaagagcatcagctgccagatctgcgag cacatcctggccgaccccgtggagaccaactgcaagcacgtgttctgtagagtgtgcatcctgcggtgcctgaaagtgatgggc agctactgccccagctgtagataccccctgcttccccaccgacctggaaagccccgtgaagagcttcctgagcgtgctgaacagc ctgatggtgaagtgccccgccaaagagtgcaacgaggaagtcagcctggaaaagtacaaccaccacatcagcagccacaa agagagcaaagaaatcttcgtccacatcaacaagggcggcagaccccggcagcacctgctgtccctgaccagacgggccca gaagcaccggctgcgggagctgaagctccaggtcaaggccttcgccgacaaagaggaaggcggcgacgtcaagagcgtgt gcatgaccctgtttctgctggccctgcgggccaggaacgagcaccggcaggccgatgagctggaagccatcatgcagggcaa gggcagcggcctccagcctgccgtgtgcctggccatccgggtgaacacctttctgagctgtagccagtaccacaagatgtaccg gaccgtgaaggccatcaccggcagacagatcttccagcctctgcacgccctgcggaacgccgagaaggtgctgctgcccggc taccaccacttcgagtggcagccccccctgaagaacgtgagcagcagcaccgacgtgggcatcatcgacggcctgagcggc ctgtccagcagcgtggacgactaccctgtggacaccatcgccaagcggttcagatacgacagcgccctggtgtccgccctgatg gacatggaagaggacatcctggaaggcatgcggagccaggacctggacgattacctgaacggccccttcaccgtggtggtga aagagtcctgcgacggcatgggcgacgtgagcgagaagcacggcagcggccctgtggtgcccgagaaggccgtgcggttc agcttcaccatcatgaagatcaccatcgcccacagcagccagaacgtgaaggtgttcgaggaagccaagcccaacagcgag ctgtgctgcaagcccctgtgcctgatgctggccgacgagagcgaccacgagaccctgaccgccatcctgagcccccctgatcgc cgagcgggaggccatgaagagcagcgaactgatgctggaactgggcggcatcctgaggaccttcaagttcatcttccggggc -continued accggctacgacgagaagctggtccgggaggtggagggcctggaagccagcggcagcgtgtacatctgcaccctgtgcgac gccacccggctggaagcctcccagaacctggtgttccacagcatcaccagaagccacgccgagaacctggaaagatacgaa gtgtggcggagcaacccctaccacgagagcgtggaggaactgcgggaccgggtcaagggcgtgagcgccaagcccttcatc gagaccgtgcccagcatcgacgccctgcactgcgatatcggcaacgccgccgagttctacaagatctttcagctggaaatcggg gaggtgtacaagaaccccaacgccagcaaagaggaacggaagcgctggcaggccaccctggacaagcacctgaggaag aaaatgaacctgaagcccatcatgcggatgaacggcaacttcgctcggaagctgatgaccaaagaaaccgtggacgccgtgt gcgagctgatccccagcgaggaacggcacgaggccctgcgcgagctgatggacctgtacctgaagatgaagcccgtgtgga gaagcagctgtcctgccaaagaatgccccgagagcctgtgccagtacagcttcaacagccagcggttcgccgagctgctgtcc accaagttcaagtaccgctacgagggcaagatcaccaactacttccacaagaccctggcccacgtgcccgagatcatcgagc gggacggcagcatcggcgcctgggccagcgagggcaacgagagcggcaacaagctgttccggcggttcagaaagatgaat gccaggcagagcaagtgctacgagatggaagatgtgctgaagcaccactggctgtacaccagcaagtacctccagaaattca tgaacgcccacaacgccctgaaaaccagcggcttcaccatgaacccccaggccagcctgggcgaccctctgggcatcgagg actccctggaatcccaggacagcatggaattctga SEQ ID NO: 5:
MND promoter sequence
tttatttagt ctccagaaaa aggggggaat gaaagacccc acctgtaggt ttggcaagct aggatcaagg ttaggaacag agagacagca gaatatgggc caaacaggat atctgtggta agcagttcct gccccggctc agggccaaga acagttggaa cagcagaata tgggccaaac aggatatctg tggtaagcag ttcctgcccc ggctcagggc caagaacaga tggtccccag atgcggtccc gccctcagca gtttctagag aaccatcaga tgtttccagg gtgccccaag gacctgaaat gaccctgtgc cttatttgaa ctaaccaatc agttcgcttc tcgcttctgt tcgcgcgctt ctgctccccg agctcaataa aagagccca SEQ ID NO: 6:
primer
5'-TGGAGATAACACTCTAAGCATAACTAAAGGT-3'

SEQ ID NO: 7:
primer
5'-GATGTAGTTGCTTGGGACCCA-3'

SEQ ID NO: 8:
probe
5'FAM-CCATTTTTGGTTTGGGCTTCACACCATT- TAMRA 3'

SEQ ID NO: 9:
primer
5' CAACTGCAAGCACGTGTTCTG 3'

SEQ ID NO: 10:
primer
5' GCAGTAGCTGCCCATCACTTT 3'

SEQ ID NO: 11:
probe
5'FAM AGAGTGTGCATCCTGCGGTGCCT TAMRA 3'

For SEQ ID NO: 12 to 43, see Tables 5 and 6; and FIG. 9.

REFERENCE LIST

Beillard et al., Evaluation of candidate control genes for diagnosis and residual disease detection in leukemic patients using 'real-time' quantitative reverse-transcriptase polymerase chain reaction (RQ-PCR)—a Europe against cancer program—Leukemia volume 17, pages 2474-2486 (2003)

Bancroft, J. D., and Gamble, M. (2008). Theory and Practice of Histological Techniques (Churchill Livingstone).

Baum, C., Kustikova, O., Modlich, U., Li, Z., and Fehse, B. (2006). Mutagenesis and oncogenesis by chromosomal insertion of gene transfer vectors. Hum Gene Ther 17, 253-263.

Dull, T., Zufferey, R., Kelly, M., Mandel, R. J., Nguyen, M., Trono, D., and Naldini, L. (1998). A third-generation lentivirus vector with a conditional packaging system. J Virol 72, 8463-8471.

Gabriel, R., Kutschera, I., Bartholomae, C. C., von Kalle, C., and Schmidt, M. (2014). Linear amplification mediated PCR—localization of genetic elements and characterization of unknown flanking DNA. J Vis Exp, e51543.

Gennery, A. R., Slatter, M. A., Grandin, L., Taupin, P., Cant, A. J., Veys, P., Amrolia, P. J., Gaspar, H. B., Davies, E. G., Friedrich, W., et al. Transplantation of hematopoietic stem cells and long-term survival for primary immunodeficiencies in Europe: entering a new century, do we do better? The Journal of allergy and clinical immunology 126, 602-610 e601-611.

Howe, S. J., Mansour, M. R., Schwarzwaelder, K., Bartholomae, C., Hubank, M., Kempski, H., Brugman, M. H., Pike-Overzet, K., Chatters, S. J., de Ridder, D., et al. (2008). Insertional mutagenesis combined with acquired somatic mutations causes leukemogenesis following gene therapy of SCID-X1 patients. The Journal of clinical investigation 118, 3143-3150.

Lagresle-Peyrou, C., Benjelloun, F., Hue, C., Andre-Schmutz, I., Bonhomme, D., Forveille, M., Beldjord, K., Hacein-Bey-Abina, S., De Villartay, J. P., Charneau, P., et al. (2008). Restoration of human B-cell differentiation into NOD-SCID mice engrafted with gene-corrected CD34+ cells isolated from Artemis or RAG1-deficient patients. Molecular therapy: the journal of the American Society of Gene Therapy 16, 396-403.

Lagresle-Peyrou, C., Yates, F., Malassis-Seris, M., Hue, C., Morillon, E., Garrigue, A., Liu, A., Hajdari, P., Stockholm, D., Danos, O., et al. (2006). Long-term immune reconstitution in RAG-1-deficient mice treated by retroviral gene therapy: a balance between efficiency and toxicity. Blood 107, 63-72.

Modlich, U., Bohne, J., Schmidt, M., von Kalle, C., Knöss, S., Schambach, A., and Baum, C. (2006). Cell-culture assays reveal the importance of retroviral vector design for insertional genotoxicity. Blood 108, 2545-2553.

Pannetier, C., Cochet, M., Darche, S., Casrouge, A., Zöller, M., and Kourilsky, P. (1993). The sizes of the CDR3 hypervariable regions of the murine T-cell receptor beta chains vary as a function of the recombined germ-line segments. Proceedings of the National Academy of Sciences of the United States of America 90, 4319-4323.

Pike-Overzet, K., Baum, C., Bredius, R. G., Cavazzana, M., Driessen, G. J., Fibbe, W. E., Gaspar, H. B., Hoeben, R. C., Lagresle-Peyrou, C., Lankester, A., et al. (2014). Successful RAG1-SCID gene therapy depends on the level of RAG1 expression. The Journal of allergy and clinical immunology 134, 242-243.

Pike-Overzet, K., de Ridder, D., Weerkamp, F., Baert, M. R., Verstegen, M. M., Brugman, M. H., Howe, S. J., Reinders, M. J., Thrasher, A. J., Wagemaker, G., et al. (2006). Gene therapy: is IL2RG oncogenic in T-cell development? Nature 443, E5; discussion E6-7.

Pike-Overzet, K., Rodijk, M., Ng, Y. Y., Baert, M. R., Lagresle-Peyrou, C., Schambach, A., Zhang, F., Hoeben, R. C., Hacein-Bey-Abina, S., Lankester, A. C., et al. (2011). Correction of murine Rag1 deficiency by self-inactivating lentiviral vector-mediated gene transfer. Leukemia 25, 1471-1483.

Pike-Overzet, K., van der Burg, M., Wagemaker, G., van Dongen, J. J., and Staal, F. J. (2007). New insights and unresolved issues regarding insertional mutagenesis in X-linked SCID gene therapy. Molecular therapy: the journal of the American Society of Gene Therapy 15, 1910-1916.

van Dongen, J. J. M., Langerak, A. W., Brüggemann, M., Evans, P. A. S., Hummel, M., Lavender, F. L., Delabesse, E., Davi, F., Schuuring, E., Garcia-Sanz, R., et al. (2003). Design and standardization of PCR primers and protocols for detection of clonal immunoglobulin and T-cell receptor gene recombinations in suspect lymphoproliferations: Report of the BIOMED-2 Concerted Action BMH4-CT98-3936. Leukemia 17, 2257.

van Til, N. P., Sarwari, R., Visser, T. P., Hauer, J., Lagresle-Peyrou, C., van der Velden, G., Malshetty, V., Cortes, P., Jollet, A., Danos, O., et al. (2014). Recombination-activating gene 1 (Rag1)-deficient mice with severe combined immunodeficiency treated with lentiviral gene therapy demonstrate autoimmune Omenn-like syndrome. Journal of Allergy and Clinical Immunology 133, 1116-1123.

WHO (2005). WHO guidelines on nonclinical evaluation of vaccines, W.H. Organization, ed. (Tech Rep Ser), pp. 31-63.

The invention claimed is:

1. A self-inactivating (SIN) lentiviral plasmid comprising an expression cassette comprising a promoter operably linked to a RAG1 transgene that comprises the nucleic acid sequence set forth by SEQ ID NO: 4, wherein the promoter is the MND promoter.

2. The SIN lentiviral plasmid of claim 1, wherein, when the expression cassette is integrated in the genome of a human CD34+ haematopoietic stem cell at 5 or fewer copy numbers, the expression cassette generates RAG expression at a level at least three-fold higher than the expression of the housekeeping gene ABL.

3. The SIN lentiviral plasmid of claim 1, wherein the expression cassette further comprises a nucleotide sequence encoding Woodchuck hepatitis virus posttranscriptional regulatory element (WPRE).

4. The SIN lentiviral plasmid of claim 1, wherein the plasmid backbone is the pCCL backbone.

5. The SIN lentiviral plasmid of claim 1, comprising the pCLL backbone, a nucleotide sequence encoding WPRE, and the expression cassette.

6. A lentiviral virion comprising an expression cassette comprising a promoter operably linked to a RAG1 transgene that comprises the nucleic acid sequence set forth by SEQ ID NO:4, wherein the promoter is the MND promoter.

7. A recombinant CD34+ hematopoietic stem cell comprising the SIN lentiviral plasmid of claim 1.

8. An ex vivo method of generating a recombinant CD34+ haematopoietic stem cell, the method comprising contacting a CD34+ haematopoietic stem cell with the SIN lentiviral plasmid of claim 1 under conditions in which the expression cassette is incorporated and expressed by the CD34+ hematopoietic stem cell to generate the recombinant CD34+ haematopoietic stem cell.

9. A method for treating a subject in need thereof, comprising administering the subject a therapeutically effective amount of the SIN lentiviral plasmid of claim 1.

10. The method of claim 9, wherein the subject has RAG1 deficient SCID, Omenn syndrome (OS), atypical SCID or combined immunodeficiency (CID).

11. The method of claim 10, wherein the subject has RAG1 deficient SCID.

12. A method of treating RAG1 deficient SCID, Omenn syndrome (OS), atypical SCID or combined immunodeficiency (CID) in a subject in need thereof comprising the steps of:

(i) extracting CD34+ haematopoietic stem cells from said subject;

(ii) contacting the CD34+ haematopoietic stem cells from (i) with the lentiviral virion of claim 6;

(iii) incubating the CD34+ haematopoietic stem cells from (ii) for a period of time; and (iv) introducing the CD34+ haematopoietic stem cells from (iii) in said subject.

13. The method of claim 12, further comprising the step of administering chemotherapy to the subject prior to step (iv).

14. A composition comprising the SIN lentiviral plasmid of claim 1 and a pharmaceutically acceptable adjuvant, carrier, excipient or diluent.

15. A composition comprising the lentiviral virion of claim 6 and a pharmaceutically acceptable adjuvant, carrier, excipient or diluent.

16. An ex vivo method of generating a recombinant CD34+ haematopoietic stem cell, the method comprising contacting a CD34+ haematopoietic stem cell with the lentiviral virion of claim 6 under conditions in which the expression cassette is incorporated and expressed by the CD34+ hematopoietic stem cell to generate the recombinant CD34+ haematopoietic stem cell.

17. A method of treating RAG1 deficient SCID, Omenn syndrome (OS), atypical SCID or combined immunodeficiency (CID) in a subject in need thereof comprising the steps of:

(i) extracting CD34+ haematopoietic stem cells from said subject;

(ii) contacting the CD34+ haematopoietic stem cells from (i) with the SIN lentiviral plasmid of claim 1;

(iii) incubating the CD34+ haematopoietic stem cells from (ii) for a period of time; and (iv) introducing the CD34+ haematopoietic stem cells from (iii) in said subject.

18. A recombinant CD34+ hematopoietic stem cell comprising the expression cassette of the lentiviral virion of claim 6.

19. A method for treating a subject in need thereof, comprising administering a therapeutically effective amount of the recombinant CD34+ hematopoietic stem cells of claim 18 to the subject in need thereof.

20. A method for treating a subject in need thereof comprising administering a therapeutically effective amount of the recombinant CD34+hematopoietic stem cells of claim 7 to the subject in need thereof.

* * * * *

SEQUENCE LISTING

```
<160> NUMBER OF SEQ ID NOS: 44

<210> SEQ ID NO 1
<211> LENGTH: 1043
<212> TYPE: PRT
<213> ORGANISM: Homo sapiens

<400> SEQUENCE: 1

Met Ala Ala Ser Phe Pro Pro Thr Leu Gly Leu Ser Ser Ala Pro Asp
1               5                   10                  15

Glu Ile Gln His Pro His Ile Lys Phe Ser Glu Trp Lys Phe Lys Leu
            20                  25                  30

Phe Arg Val Arg Ser Phe Glu Lys Thr Pro Glu Glu Ala Gln Lys Glu
        35                  40                  45

Lys Lys Asp Ser Phe Glu Gly Lys Pro Ser Leu Glu Gln Ser Pro Ala
    50                  55                  60

Val Leu Asp Lys Ala Asp Gly Gln Lys Pro Val Pro Thr Gln Pro Leu
65                  70                  75                  80

Leu Lys Ala His Pro Lys Phe Ser Lys Lys Phe His Asp Asn Glu Lys
                85                  90                  95
```

```
Ala Arg Gly Lys Ala Ile His Gln Ala Asn Leu Arg His Leu Cys Arg
            100                 105                 110

Ile Cys Gly Asn Ser Phe Arg Ala Asp Glu His Asn Arg Arg Tyr Pro
        115                 120                 125

Val His Gly Pro Val Asp Gly Lys Thr Leu Gly Leu Leu Arg Lys Lys
    130                 135                 140

Glu Lys Arg Ala Thr Ser Trp Pro Asp Leu Ile Ala Lys Val Phe Arg
145                 150                 155                 160

Ile Asp Val Lys Ala Asp Val Asp Ser Ile His Pro Thr Glu Phe Cys
                165                 170                 175

His Asn Cys Trp Ser Ile Met His Arg Lys Phe Ser Ser Ala Pro Cys
            180                 185                 190

Glu Val Tyr Phe Pro Arg Asn Val Thr Met Glu Trp His Pro His Thr
        195                 200                 205

Pro Ser Cys Asp Ile Cys Asn Thr Ala Arg Arg Gly Leu Lys Arg Lys
    210                 215                 220

Ser Leu Gln Pro Asn Leu Gln Leu Ser Lys Lys Leu Lys Thr Val Leu
225                 230                 235                 240

Asp Gln Ala Arg Gln Ala Arg Gln His Lys Arg Arg Ala Gln Ala Arg
                245                 250                 255

Ile Ser Ser Lys Asp Val Met Lys Lys Ile Ala Asn Cys Ser Lys Ile
            260                 265                 270

His Leu Ser Thr Lys Leu Leu Ala Val Asp Phe Pro Glu His Phe Val
        275                 280                 285

Lys Ser Ile Ser Cys Gln Ile Cys Glu His Ile Leu Ala Asp Pro Val
    290                 295                 300

Glu Thr Asn Cys Lys His Val Phe Cys Arg Val Cys Ile Leu Arg Cys
305                 310                 315                 320

Leu Lys Val Met Gly Ser Tyr Cys Pro Ser Cys Arg Tyr Pro Cys Phe
                325                 330                 335

Pro Thr Asp Leu Glu Ser Pro Val Lys Ser Phe Leu Ser Val Leu Asn
            340                 345                 350

Ser Leu Met Val Lys Cys Pro Ala Lys Glu Cys Asn Glu Glu Val Ser
        355                 360                 365

Leu Glu Lys Tyr Asn His His Ile Ser Ser His Lys Glu Ser Lys Glu
    370                 375                 380

Ile Phe Val His Ile Asn Lys Gly Gly Arg Pro Arg Gln His Leu Leu
385                 390                 395                 400

Ser Leu Thr Arg Arg Ala Gln Lys His Arg Leu Arg Glu Leu Lys Leu
                405                 410                 415

Gln Val Lys Ala Phe Ala Asp Lys Glu Glu Gly Gly Asp Val Lys Ser
            420                 425                 430

Val Cys Met Thr Leu Phe Leu Leu Ala Leu Arg Ala Arg Asn Glu His
        435                 440                 445

Arg Gln Ala Asp Glu Leu Glu Ala Ile Met Gln Gly Lys Gly Ser Gly
    450                 455                 460

Leu Gln Pro Ala Val Cys Leu Ala Ile Arg Val Asn Thr Phe Leu Ser
465                 470                 475                 480

Cys Ser Gln Tyr His Lys Met Tyr Arg Thr Val Lys Ala Ile Thr Gly
                485                 490                 495

Arg Gln Ile Phe Gln Pro Leu His Ala Leu Arg Asn Ala Glu Lys Val
            500                 505                 510
```

```
Leu Leu Pro Gly Tyr His His Phe Glu Trp Gln Pro Pro Leu Lys Asn
        515                 520                 525

Val Ser Ser Ser Thr Asp Val Gly Ile Ile Asp Gly Leu Ser Gly Leu
    530                 535                 540

Ser Ser Ser Val Asp Asp Tyr Pro Val Asp Thr Ile Ala Lys Arg Phe
545                 550                 555                 560

Arg Tyr Asp Ser Ala Leu Val Ser Ala Leu Met Asp Met Glu Glu Asp
                565                 570                 575

Ile Leu Glu Gly Met Arg Ser Gln Asp Leu Asp Asp Tyr Leu Asn Gly
            580                 585                 590

Pro Phe Thr Val Val Val Lys Glu Ser Cys Asp Gly Met Gly Asp Val
        595                 600                 605

Ser Glu Lys His Gly Ser Gly Pro Val Val Pro Glu Lys Ala Val Arg
    610                 615                 620

Phe Ser Phe Thr Ile Met Lys Ile Thr Ile Ala His Ser Ser Gln Asn
625                 630                 635                 640

Val Lys Val Phe Glu Glu Ala Lys Pro Asn Ser Glu Leu Cys Cys Lys
                645                 650                 655

Pro Leu Cys Leu Met Leu Ala Asp Glu Ser Asp His Glu Thr Leu Thr
            660                 665                 670

Ala Ile Leu Ser Pro Leu Ile Ala Glu Arg Glu Ala Met Lys Ser Ser
        675                 680                 685

Glu Leu Met Leu Glu Leu Gly Gly Ile Leu Arg Thr Phe Lys Phe Ile
    690                 695                 700

Phe Arg Gly Thr Gly Tyr Asp Glu Lys Leu Val Arg Glu Val Glu Gly
705                 710                 715                 720

Leu Glu Ala Ser Gly Ser Val Tyr Ile Cys Thr Leu Cys Asp Ala Thr
                725                 730                 735

Arg Leu Glu Ala Ser Gln Asn Leu Val Phe His Ser Ile Thr Arg Ser
            740                 745                 750

His Ala Glu Asn Leu Glu Arg Tyr Glu Val Trp Arg Ser Asn Pro Tyr
        755                 760                 765

His Glu Ser Val Glu Glu Leu Arg Asp Arg Val Lys Gly Val Ser Ala
    770                 775                 780

Lys Pro Phe Ile Glu Thr Val Pro Ser Ile Asp Ala Leu His Cys Asp
785                 790                 795                 800

Ile Gly Asn Ala Ala Glu Phe Tyr Lys Ile Phe Gln Leu Glu Ile Gly
                805                 810                 815

Glu Val Tyr Lys Asn Pro Asn Ala Ser Lys Glu Glu Arg Lys Arg Trp
            820                 825                 830

Gln Ala Thr Leu Asp Lys His Leu Arg Lys Lys Met Asn Leu Lys Pro
        835                 840                 845

Ile Met Arg Met Asn Gly Asn Phe Ala Arg Lys Leu Met Thr Lys Glu
    850                 855                 860

Thr Val Asp Ala Val Cys Glu Leu Ile Pro Ser Glu Glu Arg His Glu
865                 870                 875                 880

Ala Leu Arg Glu Leu Met Asp Leu Tyr Leu Lys Met Lys Pro Val Trp
                885                 890                 895

Arg Ser Ser Cys Pro Ala Lys Glu Cys Pro Glu Ser Leu Cys Gln Tyr
            900                 905                 910

Ser Phe Asn Ser Gln Arg Phe Ala Glu Leu Leu Ser Thr Lys Phe Lys
        915                 920                 925

Tyr Arg Tyr Glu Gly Lys Ile Thr Asn Tyr Phe His Lys Thr Leu Ala
```

```
    930                 935                 940

His Val Pro Glu Ile Ile Glu Arg Asp Gly Ser Ile Gly Ala Trp Ala
945                 950                 955                 960

Ser Glu Gly Asn Glu Ser Gly Asn Lys Leu Phe Arg Arg Phe Arg Lys
                965                 970                 975

Met Asn Ala Arg Gln Ser Lys Cys Tyr Glu Met Glu Asp Val Leu Lys
            980                 985                 990

His His Trp Leu Tyr Thr Ser Lys  Tyr Leu Gln Lys Phe  Met Asn Ala
        995                 1000                1005

His Asn  Ala Leu Lys Thr Ser  Gly Phe Thr Met Asn  Pro Gln Ala
    1010                 1015                1020

Ser Leu  Gly Asp Pro Leu Gly  Ile Glu Asp Ser Leu  Glu Ser Gln
    1025                 1030                1035

Asp Ser  Met Glu Phe
    1040
```

<210> SEQ ID NO 2
<211> LENGTH: 1051
<212> TYPE: DNA
<213> ORGANISM: Artificial Sequence
<220> FEATURE:
<223> OTHER INFORMATION: codon optimised nucleic acid sequence encoding human RAG1 catalytic domain

<400> SEQUENCE: 2

```
caagggcggc agaccccggc agcacctgct gtccctgacc agacgggccc agaagcaccg     60

gctgcgggag ctgaagctcc aggtcaaggc cttcgccgac aaagaggaag gcggcgacgt    120

caagagcgtg tgcatgaccc tgtttctgct ggccctgcgg gccaggaacg agcaccggca    180

ggccgatgag ctggaagcca tcatgcaggg caagggcagc ggcctccagc ctgccgtgtg    240

cctggccatc cgggtgaaca cctttctgag ctgtagccag taccacaaga tgtaccggac    300

cgtgaaggcc atcaccggca gacagatctt ccagcctctg cacgccctgc ggaacgccga    360

gaaggtgctg ctgcccggct accaccactt cgagtggcag cccccccctga agaacgtgag    420

cagcagcacc gacgtgggca tcatcgacgg cctgagcggc ctgtccagca gcgtggacga    480

ctaccctgtg gacaccatcg ccaagcggtt cagatacgac agcgccctgg tgtccgccct    540

gatggacatg gaagaggaca tcctggaagg catgcggagc caggacctgg acgattacct    600

gaacggcccc ttcaccgtgg tggtgaaaga gtcctgcgac ggcatgggcg acgtgagcga    660

gaagcacggc agcggccctg tggtgcccga gaaggccgtg cggttcagct tcaccatcat    720

gaagatcacc atcgcccaca gcagccagaa cgtgaaggtg ttcgaggaag ccaagcccaa    780

cagcgagctg tgctgcaagc ccctgtgcct gatgctggcc gacgagagcg accacgagac    840

cctgaccgcc atcctgagcc ccctgatcgc cgagcgggag gccatgaaga gcagcgaact    900

gatgctggaa ctgggcggca tcctgaggac cttcaagttc atcttccggg gcaccggcta    960

cgacgagaag ctggtccggg aggtggaggg cctggaagcc agcggcagcg tgtacatctg   1020

caccctgtgc gacgccaccc ggctggaagc c                                  1051
```

<210> SEQ ID NO 3
<211> LENGTH: 3132
<212> TYPE: DNA
<213> ORGANISM: Artificial Sequence
<220> FEATURE:
<223> OTHER INFORMATION: RAG1 cDNA sequence

<400> SEQUENCE: 3

```
atggcagcct ctttcccacc caccttggga ctcagttctg ccccagatga aattcagcac     60
ccacatatta aattttcaga atggaaattt aagctgttcc gggtgagatc ctttgaaaag    120
acacctgaag aagctcaaaa ggaaaagaag gattcctttg aggggaaacc ctctctggag    180
caatctccag cagtcctgga caaggctgat ggtcagaagc cagtcccaac tcagccattg    240
ttaaaagccc accctaagtt ttcaaagaaa tttcacgaca acgagaaagc aagaggcaaa    300
gcgatccatc aagccaacct tcgacatctc tgccgcatct gtgggaattc ttttagagct    360
gatgagcaca acaggagata tccagtccat ggtcctgtgg atggtaaaac cctaggcctt    420
ttacgaaaga aggaaaagag agctacttcc tggccggacc tcattgccaa ggtttttccgg   480
atcgatgtga aggcagatgt tgactcgatc caccccactg agttctgcca taactgctgg    540
agcatcatgc acaggaagtt tagcagtgcc ccatgtgagg tttacttccc gaggaacgtg    600
accatggagt ggcaccccca cacaccatcc tgtgacatct gcaacactgc ccgtcgggga    660
ctcaagagga agagtcttca gccaaacttg cagctcagca aaaaactcaa aactgtgctt    720
gaccaagcaa gacaagcccg tcagcgcaag agaagagctc aggcaaggat cagcagcaag    780
gatgtcatga agaagatcgc caactgcagt aagatacatc ttagtaccaa gctccttgca    840
gtggacttcc cagagcactt tgtgaaatcc atctcctgcc agatctgtga acacattctg    900
gctgaccctg tggagaccaa ctgtaagcat gtcttttgcc gggtctgcat tctcagatgc    960
ctcaaagtca tgggcagcta ttgtccctct tgccgatatc catgcttccc tactgacctg   1020
gagagtccag tgaagtcctt tctgagcgtc ttgaattccc tgatggtgaa atgtccagca   1080
aaagagtgca atgaggaggt cagtttggaa aaatataatc accacatctc aagtcacaag   1140
gaatcaaaag agatttttgt gcacattaat aaagggggcc ggccccgcca acatcttctg   1200
tcgctgactc ggagagctca gaagcaccgg ctgagggagc tcaagctgca agtcaaagcc   1260
tttgctgaca aagaagaagg tggagatgtg aagtccgtgt gcatgacctt gttcctgctg   1320
gctctgaggg cgaggaatga gcacaggcaa gctgatgagc tggaggccat catgcaggga   1380
aagggctctg gcctgcagcc agctgtttgc ttggccatcc gtgtcaacac cttcctcagc   1440
tgcagtcagt accacaagat gtacaggact gtgaaagcca tcacagggag acagattttt   1500
cagcctttgc atgcccttcg gaatgctgag aaggtacttc tgccaggcta ccaccacttt   1560
gagtggcagc cacctctgaa gaatgtgtct tccagcactg atgttggcat tattgatggg   1620
ctgtctggac tatcatcctc tgtggatgat tacccagtgg acaccattgc aaagaggttc   1680
cgctatgatt cagctttggt gtctgctttg atggacatgg aagaagacat cttggaaggc   1740
atgagatccc aagaccttga tgattacctg aatggcccct tcactgtggt ggtgaaggag   1800
tcttgtgatg gaatgggaga cgtgagtgag aagcatggga gtgggcctgt agttccagaa   1860
aaggcagtcc gtttttcatt cacaatcatg aaaattacta ttgcccacag ctctcagaat   1920
gtgaaagtat ttgaagaagc caaacctaac tctgaactgt gttgcaagcc attgtgcctt   1980
atgctggcag atgagtctga ccacgagacg ctgactgcca tcctgagtcc tctcattgct   2040
gagagggagg ccatgaagag cagtgaatta atgcttgagc tgggaggcat tctccggact   2100
ttcaagttca tcttcagggg caccggctat gatgaaaaac ttgtgcggga agtggaaggc   2160
ctcgaggctt ctggctcagt ctacatttgt actctttgtg atgccacccg tctggaagcc   2220
tctcaaaatc ttgtcttcca ctctataacc agaagccatg ctgagaacct ggaacgttat   2280
gaggtctggc gttccaaccc ttaccatgag tctgtggaag aactgcggga tcgggtgaaa   2340
```

```
ggggtctcag ctaaaccttt cattgagaca gtcccttcca tagatgcact ccactgtgac   2400

attggcaatg cagctgagtt ctacaagatc ttccagctag agatagggga agtgtataag   2460

aatcccaatg cttccaaaga ggaaaggaaa aggtggcagg ccacactgga caagcatctc   2520

cggaagaaga tgaacctcaa accaatcatg aggatgaatg gcaactttgc caggaagctc   2580

atgaccaaag agactgtgga tgcagtttgt gagttaattc cttccgagga gaggcacgag   2640

gctctgaggg agctgatgga tctttacctg aagatgaaac cagtatggcg atcatcatgc   2700

cctgctaaag agtgcccaga atccctctgc cagtacagtt tcaattcaca gcgttttgct   2760

gagctccttt ctacgaagtt caagtatagg tatgagggaa aaatcaccaa ttattttcac   2820

aaaaccctgg cccatgttcc tgaaattatt gagagggatg gctccattgg ggcatgggca   2880

agtgagggaa atgagtctgg taacaaactg tttaggcgct tccggaaaat gaatgccagg   2940

cagtccaaat gctatgagat ggaagatgtc ctgaaacacc actggttgta cacctccaaa   3000

tacctccaga agtttatgaa tgctcataat gcattaaaaa cctctgggtt taccatgaac   3060

cctcaggcaa gcttagggga cccattaggc atagaggact ctctggaaag ccaagattca   3120

atggaatttt aa                                                       3132
```

<210> SEQ ID NO 4
<211> LENGTH: 3132
<212> TYPE: DNA
<213> ORGANISM: Artificial Sequence
<220> FEATURE:
<223> OTHER INFORMATION: codon optimised RAG1 DNA sequence

<400> SEQUENCE: 4

```
atggccgcca gcttcccccc taccctgggc ctgagcagcg cccctgacga gatccagcac     60

ccccacatca agttcagcga gtggaagttc aagctgttca gagtgcggag cttcgagaaa    120

acccccgagg aagcccagaa agagaagaag gacagcttcg agggcaagcc cagcctggaa    180

cagagccctg ccgtgctgga caaggccgac ggccagaaac ccgtgcccac ccagcccctg    240

ctgaaggccc accccaagtt cagcaagaag ttccacgaca acgagaaggc caggggcaag    300

gccatccacc aggccaacct gcggcacctg tgccggatct gcggcaacag cttccgggcc    360

gacgagcaca accggcgcta ccccgtgcac ggccccgtgg acggcaagac actgggcctg    420

ctgcggaaga aagagaaacg ggccacctcc tggcccgacc tgatcgccaa ggtgttccgg    480

atcgacgtga aggccgacgt ggacagcatc caccccaccg agttctgcca caactgctgg    540

tccatcatgc accggaagtt cagctccgcc ccctgcgagg tgtacttccc ccggaacgtg    600

accatggaat ggcaccctca cacccccagc tgcgacatct gcaacaccgc cagacggggc    660

ctgaagcgga agagcctcca gcccaacctc cagctgtcca agaaactgaa aaccgtgctg    720

gatcaggccc ggcaggccag gcagcggaag cggagagccc aggcccggat cagcagcaag    780

gacgtgatga agaagatcgc caactgtagc aagatccacc tgagcaccaa gctgctggcc    840

gtggacttcc ccgagcactt cgtgaagagc atcagctgcc agatctgcga gcacatcctg    900

gccgaccccg tggagaccaa ctgcaagcac gtgttctgta gagtgtgcat cctgcggtgc    960

ctgaaagtga tgggcagcta ctgccccagc tgtagatacc cctgcttccc caccgacctg   1020

gaaagccccg tgaagagctt cctgagcgtg ctgaacagcc tgatggtgaa gtgccccgcc   1080

aaagagtgca acgaggaagt cagcctggaa aagtacaacc accacatcag cagccacaaa   1140

gagagcaaag aaatcttcgt ccacatcaac aagggcggca gaccccggca gcacctgctg   1200

tccctgacca gacgggccca gaagcaccgg ctgcgggagc tgaagctcca ggtcaaggcc   1260
```

```
ttcgccgaca aagaggaagg cggcgacgtc aagagcgtgt gcatgaccct gtttctgctg   1320
gccctgcggg ccaggaacga gcaccggcag gccgatgagc tggaagccat catgcagggc   1380
aagggcagcg gcctccagcc tgccgtgtgc ctggccatcc gggtgaacac ctttctgagc   1440
tgtagccagt accacaagat gtaccggacc gtgaaggcca tcaccggcag acagatcttc   1500
cagcctctgc acgccctgcg gaacgccgag aaggtgctgc tgcccggcta ccaccacttc   1560
gagtggcagc ccccctgaa gaacgtgagc agcagcaccg acgtgggcat catcgacggc   1620
ctgagcggcc tgtccagcag cgtggacgac taccctgtgg acaccatcgc caagcggttc   1680
agatacgaca gcgccctggt gtccgccctg atggacatgg aagaggacat cctggaaggc   1740
atgcggagcc aggacctgga cgattacctg aacggcccct tcaccgtggt ggtgaaagag   1800
tcctgcgacg gcatgggcga cgtgagcgag aagcacggca gcggccctgt ggtgcccgag   1860
aaggccgtgc ggttcagctt caccatcatg aagatcacca tcgcccacag cagccagaac   1920
gtgaaggtgt tcgaggaagc caagcccaac agcgagctgt gctgcaagcc cctgtgcctg   1980
atgctggccg acgagagcga ccacgagacc ctgaccgcca tcctgagccc cctgatcgcc   2040
gagcgggagg ccatgaagag cagcgaactg atgctggaac tgggcggcat cctgaggacc   2100
ttcaagttca tcttccgggg caccggctac gacgagaagc tggtccggga ggtggagggc   2160
ctggaagcca gcggcagcgt gtacatctgc accctgtgcg acgccacccg gctggaagcc   2220
tcccagaacc tggtgttcca cagcatcacc agaagccacg ccgagaacct ggaaagatac   2280
gaagtgtggc ggagcaaccc ctaccacgag agcgtggagg aactgcggga ccgggtcaag   2340
ggcgtgagcg ccaagccctt catcgagacc gtgcccagca tcgacgccct gcactgcgat   2400
atcggcaacg ccgccgagtt ctacaagatc tttcagctgg aaatcgggga ggtgtacaag   2460
aaccccaacg ccagcaaaga ggaacggaag cgctggcagg ccaccctgga caagcacctg   2520
aggaagaaaa tgaacctgaa gcccatcatg cggatgaacg gcaacttcgc tcggaagctg   2580
atgaccaaag aaaccgtgga cgccgtgtgc gagctgatcc ccagcgagga acggcacgag   2640
gccctgcgcg agctgatgga cctgtacctg aagatgaagc ccgtgtggag aagcagctgt   2700
cctgccaaag aatgccccga gagcctgtgc cagtacagct tcaacagcca gcggttcgcc   2760
gagctgctgt ccaccaagtt caagtaccgc tacgagggca agatcaccaa ctacttccac   2820
aagaccctgg cccacgtgcc cgagatcatc gagcgggacg gcagcatcgg cgcctgggcc   2880
agcgagggca acgagagcgg caacaagctg ttccggcggt tcagaaagat gaatgccagg   2940
cagagcaagt gctacgagat ggaagatgtg ctgaagcacc actggctgta caccagcaag   3000
tacctccaga aattcatgaa cgcccacaac gccctgaaaa ccagcggctt caccatgaac   3060
ccccaggcca gcctgggcga ccctctgggc atcgaggact ccctggaatc ccaggacagc   3120
atggaattct ga                                                      3132
```

```
<210> SEQ ID NO 5
<211> LENGTH: 399
<212> TYPE: DNA
<213> ORGANISM: Artificial Sequence
<220> FEATURE:
<223> OTHER INFORMATION: MND promoter sequence

<400> SEQUENCE: 5

tttatttagt ctccagaaaa aggggggaat gaaagacccc acctgtaggt ttggcaagct     60
aggatcaagg ttaggaacag agagacagca gaatatgggc caaacaggat atctgtggta    120
```

```
agcagttcct gccccggctc agggccaaga acagttggaa cagcagaata tgggccaaac    180

aggatatctg tggtaagcag ttcctgcccc ggctcagggc caagaacaga tggtccccag    240

atgcggtccc gccctcagca gtttctagag aaccatcaga tgtttccagg gtgccccaag    300

gacctgaaat gaccctgtgc cttatttgaa ctaaccaatc agttcgcttc tcgcttctgt    360

tcgcgcgctt ctgctccccg agctcaataa aagagccca                           399


<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6

tggagataac actctaagca taactaaagg t                                    31


<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7

gatgtagttg cttgggaccc a                                               21


<210> SEQ ID NO 8
<211> LENGTH: 28
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (28)..(28)
<223> OTHER INFORMATION: TAMRA

<400> SEQUENCE: 8

ccatttttgg tttgggcttc acaccatt                                        28


<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9

caactgcaag cacgtgttct g                                               21


<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10

gcagtagctg cccatcactt t                                               21
```

<210> SEQ ID NO 11
<211> LENGTH: 23
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (23)..(23)
<223> OTHER INFORMATION: TAMRA

<400> SEQUENCE: 11
agagtgtgca tcctgcggtg cct 23

<210> SEQ ID NO 12
<211> LENGTH: 22
<212> TYPE: DNA
<213> ORGANISM: Artificial Sequence
<220> FEATURE:
<223> OTHER INFORMATION: forward primer - PTBP2

<400> SEQUENCE: 12
tctccattcc ctatgttcat gc 22

<210> SEQ ID NO 13
<211> LENGTH: 22
<212> TYPE: DNA
<213> ORGANISM: Artificial Sequence
<220> FEATURE:
<223> OTHER INFORMATION: reverse primer - PTBP2

<400> SEQUENCE: 13
gttcccgcag aatggtgagg tg 22

<210> SEQ ID NO 14
<211> LENGTH: 20
<212> TYPE: DNA
<213> ORGANISM: Artificial Sequence
<220> FEATURE:
<223> OTHER INFORMATION: Probe - PTBP2
<220> FEATURE:
<221> NAME/KEY: misc_feature
<222> LOCATION: (1)..(1)
<223> OTHER INFORMATION: JOE
<220> FEATURE:
<221> NAME/KEY: misc_feature
<222> LOCATION: (20)..(20)
<223> OTHER INFORMATION: BHQ1

<400> SEQUENCE: 14
atgttcctcg gaccaacttg 20

<210> SEQ ID NO 15
<211> LENGTH: 20
<212> TYPE: DNA
<213> ORGANISM: Artificial Sequence
<220> FEATURE:
<223> OTHER INFORMATION: forward primer - WPRE

<400> SEQUENCE: 15
gaggagttgt ggcccgttgt 20

<210> SEQ ID NO 16
<211> LENGTH: 20
<212> TYPE: DNA

<213> ORGANISM: Artificial Sequence
<220> FEATURE:
<223> OTHER INFORMATION: reverse primer - WPRE

<400> SEQUENCE: 16
tgacaggtgg tggcaatgcc 20

<210> SEQ ID NO 17
<211> LENGTH: 19
<212> TYPE: DNA
<213> ORGANISM: Artificial Sequence
<220> FEATURE:
<223> OTHER INFORMATION: Probe - WPRE
<220> FEATURE:
<221> NAME/KEY: misc_feature
<222> LOCATION: (1)..(1)
<223> OTHER INFORMATION: 6FAM
<220> FEATURE:
<221> NAME/KEY: misc_feature
<222> LOCATION: (19)..(19)
<223> OTHER INFORMATION: BHQ1

<400> SEQUENCE: 17
ctgtgtttgc tgacgcaac 19

<210> SEQ ID NO 18
<211> LENGTH: 24
<212> TYPE: DNA
<213> ORGANISM: Artificial Sequence
<220> FEATURE:
<223> OTHER INFORMATION: mVb1 forward primer

<400> SEQUENCE: 18
ctgaatgccc agacagctcc aagc 24

<210> SEQ ID NO 19
<211> LENGTH: 21
<212> TYPE: DNA
<213> ORGANISM: Artificial Sequence
<220> FEATURE:
<223> OTHER INFORMATION: mVb2 forward primer

<400> SEQUENCE: 19
tcactgatac ggagctgagg c 21

<210> SEQ ID NO 20
<211> LENGTH: 22
<212> TYPE: DNA
<213> ORGANISM: Artificial Sequence
<220> FEATURE:
<223> OTHER INFORMATION: mVb3.1 forward primer

<400> SEQUENCE: 20
ccttgcagcc tagaaattca gt 22

<210> SEQ ID NO 21
<211> LENGTH: 22
<212> TYPE: DNA
<213> ORGANISM: Artificial Sequence
<220> FEATURE:
<223> OTHER INFORMATION: mVb4 forward primer

<400> SEQUENCE: 21
gcctcaagtc gcttccaacc tc 22

<210> SEQ ID NO 22
<211> LENGTH: 24

<212> TYPE: DNA
<213> ORGANISM: Artificial Sequence
<220> FEATURE:
<223> OTHER INFORMATION: mVb5.1 forward primer

<400> SEQUENCE: 22
cattatgata aaatggagag agat 24

<210> SEQ ID NO 23
<211> LENGTH: 24
<212> TYPE: DNA
<213> ORGANISM: Artificial Sequence
<220> FEATURE:
<223> OTHER INFORMATION: mVb5.2 forward primer

<400> SEQUENCE: 23
aaggtggaga gagacaaagg attc 24

<210> SEQ ID NO 24
<211> LENGTH: 21
<212> TYPE: DNA
<213> ORGANISM: Artificial Sequence
<220> FEATURE:
<223> OTHER INFORMATION: mVb5.3 forward primer

<400> SEQUENCE: 24
agaaaggaaa cctgcctggt t 21

<210> SEQ ID NO 25
<211> LENGTH: 21
<212> TYPE: DNA
<213> ORGANISM: Artificial Sequence
<220> FEATURE:
<223> OTHER INFORMATION: mVb6 forward primer

<400> SEQUENCE: 25
ctctcactgt gacatctgcc c 21

<210> SEQ ID NO 26
<211> LENGTH: 22
<212> TYPE: DNA
<213> ORGANISM: Artificial Sequence
<220> FEATURE:
<223> OTHER INFORMATION: mVb7 forward primer

<400> SEQUENCE: 26
tacagggtct cacggaagaa gc 22

<210> SEQ ID NO 27
<211> LENGTH: 21
<212> TYPE: DNA
<213> ORGANISM: Artificial Sequence
<220> FEATURE:
<223> OTHER INFORMATION: mVb8.1 forward primer

<400> SEQUENCE: 27
cattactcat atgtcgctga c 21

<210> SEQ ID NO 28
<211> LENGTH: 21
<212> TYPE: DNA
<213> ORGANISM: Artificial Sequence
<220> FEATURE:
<223> OTHER INFORMATION: mVb8.2 forward primer

<400> SEQUENCE: 28
cattattcat atggtgctgg c 21

<210> SEQ ID NO 29
<211> LENGTH: 22
<212> TYPE: DNA
<213> ORGANISM: Artificial Sequence
<220> FEATURE:
<223> OTHER INFORMATION: mVb8.3 forward primer

<400> SEQUENCE: 29
tgctggcaac cttcgaatag ga 22

<210> SEQ ID NO 30
<211> LENGTH: 24
<212> TYPE: DNA
<213> ORGANISM: Artificial Sequence
<220> FEATURE:
<223> OTHER INFORMATION: mVb9 forward primer

<400> SEQUENCE: 30
tctctctaca ttggctctgc aggc 24

<210> SEQ ID NO 31
<211> LENGTH: 23
<212> TYPE: DNA
<213> ORGANISM: Artificial Sequence
<220> FEATURE:
<223> OTHER INFORMATION: mvb10 forward primer

<400> SEQUENCE: 31
atcaagtctg tagagccgga gga 23

<210> SEQ ID NO 32
<211> LENGTH: 25
<212> TYPE: DNA
<213> ORGANISM: Artificial Sequence
<220> FEATURE:
<223> OTHER INFORMATION: mvb11 forward primer

<400> SEQUENCE: 32
gcactcaact ctgaagatcc agagc 25

<210> SEQ ID NO 33
<211> LENGTH: 22
<212> TYPE: DNA
<213> ORGANISM: Artificial Sequence
<220> FEATURE:
<223> OTHER INFORMATION: mVb12 forward primer

<400> SEQUENCE: 33
gatggtgggg ctttcaagga tc 22

<210> SEQ ID NO 34
<211> LENGTH: 24
<212> TYPE: DNA
<213> ORGANISM: Artificial Sequence
<220> FEATURE:
<223> OTHER INFORMATION: mVb13 forward primer

<400> SEQUENCE: 34
aggcctaaag gaactaactc ccac 24

<210> SEQ ID NO 35
<211> LENGTH: 22
<212> TYPE: DNA
<213> ORGANISM: Artificial Sequence
<220> FEATURE:
<223> OTHER INFORMATION: mVb14 forward primer

<400> SEQUENCE: 35
acgaccaatt catcctaagc ac 22

<210> SEQ ID NO 36
<211> LENGTH: 24
<212> TYPE: DNA
<213> ORGANISM: Artificial Sequence
<220> FEATURE:
<223> OTHER INFORMATION: mVb15 forward primer

<400> SEQUENCE: 36
cccatcagtc atcccaactt atcc 24

<210> SEQ ID NO 37
<211> LENGTH: 21
<212> TYPE: DNA
<213> ORGANISM: Artificial Sequence
<220> FEATURE:
<223> OTHER INFORMATION: mVb16 forward primer

<400> SEQUENCE: 37
cactctgaaa atccaaccca c 21

<210> SEQ ID NO 38
<211> LENGTH: 20
<212> TYPE: DNA
<213> ORGANISM: Artificial Sequence
<220> FEATURE:
<223> OTHER INFORMATION: mVb17 forward primer

<400> SEQUENCE: 38
agtgttcctc gaactcacag 20

<210> SEQ ID NO 39
<211> LENGTH: 24
<212> TYPE: DNA
<213> ORGANISM: Artificial Sequence
<220> FEATURE:
<223> OTHER INFORMATION: mVb18 forward primer

<400> SEQUENCE: 39
cagccggcca aacctaacat tctc 24

<210> SEQ ID NO 40
<211> LENGTH: 21
<212> TYPE: DNA
<213> ORGANISM: Artificial Sequence
<220> FEATURE:
<223> OTHER INFORMATION: mVb19 forward primer

<400> SEQUENCE: 40
ctgctaagaa accatgtacc a 21

<210> SEQ ID NO 41
<211> LENGTH: 21
<212> TYPE: DNA
<213> ORGANISM: Artificial Sequence
<220> FEATURE:
<223> OTHER INFORMATION: mVb20 forward primer

<400> SEQUENCE: 41
tctgcagcct gggaatcaga a 21

<210> SEQ ID NO 42
<211> LENGTH: 22
<212> TYPE: DNA
<213> ORGANISM: Artificial Sequence
<220> FEATURE:
<223> OTHER INFORMATION: muTCB1-FAM reverse primer
<220> FEATURE:
<221> NAME/KEY: misc_feature
<222> LOCATION: (1)..(1)
<223> OTHER INFORMATION: FAM

<400> SEQUENCE: 42
cttgggtgga gtcacatttc tc 22

<210> SEQ ID NO 43
<211> LENGTH: 10111
<212> TYPE: DNA
<213> ORGANISM: Artificial Sequence
<220> FEATURE:
<223> OTHER INFORMATION: pCCL.MND.coRAG1 plasmid

<400> SEQUENCE: 43
ccattgcata cgttgtatcc atatcataat atgtacattt atattggctc atgtccaaca 60
ttaccgccat gttgacattg attattgact agttattaat agtaatcaat tacggggtca 120
ttagttcata gcccatatat ggagttccgc gttacataac ttacggtaaa tggcccgcct 180
ggctgaccgc ccaacgaccc ccgcccattg acgtcaataa tgacgtatgt tcccatagta 240
acgccaatag ggactttcca ttgacgtcaa tgggtggagt atttacggta aactgcccac 300
ttggcagtac atcaagtgta tcatatgcca agtacgcccc ctattgacgt caatgacggt 360
aaatggcccg cctggcatta tgcccagtac atgaccttat gggactttcc tacttggcag 420
tacatctacg tattagtcat cgctattacc atggtgatgc ggttttggca gtacatcaat 480
gggcgtggat agcggtttga ctcacgggga tttccaagtc tccaccccat tgacgtcaat 540
gggagtttgt tttggcacca aaatcaacgg gactttccaa aatgtcgtaa caactccgcc 600
ccattgacgc aaatgggcgg taggcgtgta cggtgggagg tctatataag cagagctcgt 660
ttagtgaacc ggggtctctc tggttagacc agatctgagc ctgggagctc tctggctaac 720
tagggaaccc actgcttaag cctcaataaa gcttgccttg agtgcttcaa gtagtgtgtg 780
cccgtctgtt gtgtgactct ggtaactaga gatccctcag acccttttag tcagtgtgga 840
aaatctctag cagtggcgcc cgaacaggga cttgaaagcg aaagggaaac cagaggagct 900
ctctcgacgc aggactcggc ttgctgaagc gcgcacggca agaggcgagg ggcggcgact 960
ggtgagtacg ccaaaaattt tgactagcgg aggctagaag gagagagatg ggtgcgagag 1020
cgtcagtatt aagcggggga gaattagatc gcgatgggaa aaaattcggt taaggccagg 1080
gggaaagaaa aaatataaat taaaacatat agtatgggca agcagggagc tagaacgatt 1140
cgcagttaat cctggcctgt tagaaacatc agaaggctgt agacaaatac tgggacagct 1200
acaaccatcc cttcagacag gatcagaaga acttagatca ttatataata cagtagcaac 1260
cctctattgt gtgcatcaaa ggatagagat aaaagacacc aaggaagctt tagacaagat 1320
agaggaagag caaaacaaaa gtaagaccac cgcacagcaa gcggccgctg atcttcagac 1380
ctggaggagg agatatgagg gacaattgga gaagtgaatt atataaatat aaagtagtaa 1440
aaattgaacc attaggagta gcacccacca aggcaaagag aagagtggtg cagagagaaa 1500
aaagagcagt gggaatagga gctttgttcc ttgggttctt gggagcagca ggaagcacta 1560
tgggcgcagc gtcaatgacg ctgacggtac aggccagaca attattgtct ggtatagtgc 1620

```
agcagcagaa caatttgctg agggctattg aggcgcaaca gcatctgttg caactcacag   1680
tctggggcat caagcagctc caggcaagaa tcctggctgt ggaaagatac ctaaaggatc   1740
aacagctcct ggggatttgg ggttgctctg gaaaactcat ttgcaccact gctgtgcctt   1800
ggaatgctag ttggagtaat aaatctctgg aacagatttg gaatcacacg acctggatgg   1860
agtgggacag agaaattaac aattacacaa gcttaataca ctccttaatt gaagaatcgc   1920
aaaaccagca agaaaagaat gaacaagaat tattggaatt agataaatgg gcaagtttgt   1980
ggaattggtt taacataaca aattggctgt ggtatataaa attattcata atgatagtag   2040
gaggcttggt aggtttaaga atagtttttg ctgtactttc tatagtgaat agagttaggc   2100
agggatattc accattatcg tttcagaccc acctcccaac cccgagggga cccgacaggc   2160
ccgaaggaat agaagaagaa ggtggagaga gagacagaga cagatccatt cgattagtga   2220
acggatctcg acggtatcgg ttaactttta aaagaaaagg ggggattggg gggtacagtg   2280
caggggaaag aatagtagac ataatagcaa cagacataca aactaaagaa ttacaaaaac   2340
aaattacaaa aattcaaaat tttatcgatc acgagactag cctcgacgcg tagcctcgag   2400
ctagcggtac cgatcaaggt taggaacaga gagacaggag aatatgggcc aaacaggata   2460
tctgtggtaa gcagttcctg ccccggctca gggccaagaa cagttggaac agcagaatat   2520
gggccaaaca ggatatctgt ggtaagcagt tcctgccccg gctcagggcc aagaacagat   2580
ggtccccaga tgcggtcccg ccctcagcag tttctagaga accatcagat gtttccaggg   2640
tgccccaagg acctgaaatg accctgtgcc ttatttgaac taaccaatca gttcgcttct   2700
cgcttctgtt cgcgcgcttc tgctccccga gctcaataaa agagcccaca acccctcact   2760
cggcgcgcca gtcctccgat agactgcgtc gcccgggatc caccggtgcc accatggccg   2820
ccagcttccc ccctaccctg ggcctgagca gcgcccctga cgagatccag caccccccaca   2880
tcaagttcag cgagtggaag ttcaagctgt tcagagtgcg gagcttcgag aaaacccccg   2940
aggaagccca gaaagagaag aaggacagct tcgagggcaa gcccagcctg gaacagagcc   3000
ctgccgtgct ggacaaggcc gacggccaga aacccgtgcc cacccagccc ctgctgaagg   3060
cccaccccaa gttcagcaag aagttccacg acaacgagaa ggccaggggc aaggccatcc   3120
accaggccaa cctgcggcac ctgtgccgga tctgcggcaa cagcttccgg gccgacgagc   3180
acaaccggcg ctaccccgtg cacggccccg tggacggcaa gacactgggc ctgctgcgga   3240
agaaagagaa acgggccacc tcctggcccg acctgatcgc caaggtgttc cggatcgacg   3300
tgaaggccga cgtggacagc atccacccca ccgagttctg ccacaactgc tggtccatca   3360
tgcaccggaa gttcagctcc gccccctgcg aggtgtactt cccccggaac gtgaccatgg   3420
aatggcaccc tcacaccccc agctgcgaca tctgcaacac cgccagacgg ggcctgaagc   3480
ggaagagcct ccagcccaac ctccagctgt ccaagaaact gaaaaccgtg ctggatcagg   3540
cccggcaggc caggcagcgg aagcggagag cccaggcccg gatcagcagc aaggacgtga   3600
tgaagaagat cgccaactgt agcaagatcc acctgagcac caagctgctg gccgtggact   3660
tccccgagca cttcgtgaag agcatcagct gccagatctg cgagcacatc ctggccgacc   3720
ccgtggagac caactgcaag cacgtgttct gtagagtgtg catcctgcgg tgcctgaaag   3780
tgatgggcag ctactgcccc agctgtagat accccctgctt ccccaccgac ctggaaagcc   3840
ccgtgaagag cttcctgagc gtgctgaaca gcctgatggt gaagtgcccc gccaaagagt   3900
gcaacgagga agtcagcctg gaaaagtaca accaccacat cagcagccac aaagagagca   3960
```

```
aagaaatctt cgtccacatc aacaagggcg gcagaccccg gcagcacctg ctgtccctga   4020
ccagacgggc ccagaagcac cggctgcggg agctgaagct ccaggtcaag gccttcgccg   4080
acaaagagga aggcggcgac gtcaagagcg tgtgcatgac cctgtttctg ctggccctgc   4140
gggccaggaa cgagcaccgg caggccgatg agctggaagc catcatgcag ggcaagggca   4200
gcggcctcca gcctgccgtg tgcctggcca tccgggtgaa cacctttctg agctgtagcc   4260
agtaccacaa gatgtaccgg accgtgaagg ccatcaccgg cagacagatc ttccagcctc   4320
tgcacgccct gcggaacgcc gagaaggtgc tgctgcccgg ctaccaccac ttcgagtggc   4380
agcccccccct gaagaacgtg agcagcagca ccgacgtggg catcatcgac ggcctgagcg   4440
gcctgtccag cagcgtggac gactaccctg tggacaccat cgccaagcgg ttcagatacg   4500
acagcgccct ggtgtccgcc ctgatggaca tggaagagga catcctggaa ggcatgcgga   4560
gccaggacct ggacgattac ctgaacggcc ccttcaccgt ggtggtgaaa gagtcctgcg   4620
acggcatggg cgacgtgagc gagaagcacg gcagcggccc tgtggtgccc gagaaggccg   4680
tgcggttcag cttcaccatc atgaagatca ccatcgccca cagcagccag aacgtgaagg   4740
tgttcgagga agccaagccc aacagcgagc tgtgctgcaa gcccctgtgc ctgatgctgg   4800
ccgacgagag cgaccacgag accctgaccg ccatcctgag ccccctgatc gccgagcggg   4860
aggccatgaa gagcagcgaa ctgatgctgg aactgggcgg catcctgagg accttcaagt   4920
tcatcttccg gggcaccggc tacgacgaga agctggtccg ggaggtggag ggcctggaag   4980
ccagcggcag cgtgtacatc tgcaccctgt gcgacgccac ccggctggaa gcctcccaga   5040
acctggtgtt ccacagcatc accagaagcc acgccgagaa cctggaaaga tacgaagtgt   5100
ggcggagcaa cccctaccac gagagcgtgg aggaactgcg ggaccgggtc aagggcgtga   5160
gcgccaagcc cttcatcgag accgtgccca gcatcgacgc cctgcactgc gatatcggca   5220
acgccgccga gttctacaag atctttcagc tggaaatcgg ggaggtgtac aagaacccca   5280
acgccagcaa agaggaacgg aagcgctggc aggccaccct ggacaagcac ctgaggaaga   5340
aaatgaacct gaagcccatc atgcggatga acggcaactt cgctcggaag ctgatgacca   5400
aagaaaccgt ggacgccgtg tgcgagctga tccccagcga ggaacggcac gaggccctgc   5460
gcgagctgat ggacctgtac ctgaagatga agcccgtgtg gagaagcagc tgtcctgcca   5520
aagaatgccc cgagagcctg tgccagtaca gcttcaacag ccagcggttc gccgagctgc   5580
tgtccaccaa gttcaagtac cgctacgagg gcaagatcac caactacttc cacaagaccc   5640
tggcccacgt gcccgagatc atcgagcggg acggcagcat cggcgcctgg gccagcgagg   5700
gcaacgagag cggcaacaag ctgttccggc ggttcagaaa gatgaatgcc aggcagagca   5760
agtgctacga gatggaagat gtgctgaagc accactggct gtacaccagc aagtacctcc   5820
agaaattcat gaacgcccac aacgccctga aaaccagcgg cttcaccatg aacccccagg   5880
ccagcctggg cgaccctctg ggcatcgagg actccctgga atcccaggac agcatggaat   5940
tctgatgagt cgacaatcaa cctctggatt acaaaatttg tgaaagattg actggtattc   6000
ttaactatgt tgctcctttt acgctatgtg gatacgctgc tttaatgcct ttgtatcatg   6060
ctattgcttc ccgtatggct ttcattttct cctccttgta taaatcctgg ttgctgtctc   6120
tttatgagga gttgtggccc gttgtcaggc aacgtggcgt ggtgtgcact gtgtttgctg   6180
acgcaacccc cactggttgg ggcattgcca ccacctgtca gctcctttcc gggactttcg   6240
ctttccccct ccctattgcc acggcggaac tcatcgccgc ctgccttgcc cgctgctgga   6300
caggggctcg gctgttgggc actgacaatt ccgtggtgtt gtcggggaaa tcatcgtcct   6360
```

-continued

```
ttccttggct gctcgcctgt gttgccacct ggattctgcg cgggacgtcc ttctgctacg   6420
tcccttcggc cctcaatcca gcggaccttc cttcccgcgg cctgctgccg gctctgcggc   6480
ctcttccgcg tcttcgcctt cgccctcaga cgagtcggat ctccctttgg gccgcctccc   6540
cgcctggaat tcgagctcgg tacctttaag accaatgact tacaaggcag ctgtagatct   6600
tagccacttt ttaaaagaaa aggggggact ggaagggcta attcactccc aacgaagaca   6660
agatctgctt tttgcttgta ctgggtctct ctggttagac cagatctgag cctgggagct   6720
ctctggctaa ctagggaacc cactgcttaa gcctcaataa agcttgcctt gagtgcttca   6780
agtagtgtgt gcccgtctgt tgtgtgactc tggtaactag agatccctca gaccctttta   6840
gtcagtgtgg aaaatctcta gcagtagtag ttcatgtcat cttattattc agtatttata   6900
acttgcaaag aaatgaatat cagagagtga gaggaacttg tttattgcag cttataatgg   6960
ttacaaataa agcaatagca tcacaaattt cacaaataaa gcattttttt cactgcattc   7020
tagttgtggt ttgtccaaac tcatcaatgt atcttatcat gtctggctct agctatcccg   7080
cccctaactc cgcccatccc gcccctaact ccgcccagtt ccgcccattc tccgccccat   7140
ggctgactaa ttttttttat ttatgcagag gccgaggccg cctcggcctc tgagctattc   7200
cagaagtagt gaggaggctt ttttggaggc ctagggacgt acccaattcg ccctatagtg   7260
agtcgtatta cgcgcgctca ctggccgtcg ttttacaacg tcgtgactgg gaaaaccctg   7320
gcgttaccca acttaatcgc cttgcagcac atcccccttt cgccagctgg cgtaatagcg   7380
aagaggcccg caccgatcgc ccttcccaac agttgcgcag cctgaatggc gaatgggacg   7440
cgccctgtag cggcgcatta agcgcggcgg gtgtggtggt tacgcgcagc gtgaccgcta   7500
cacttgccag cgccctagcg cccgctcctt tcgctttctt cccttccttt ctcgccacgt   7560
tcgccggctt tccccgtcaa gctctaaatc gggggctccc tttagggttc cgatttagtg   7620
ctttacggca cctcgacccc aaaaaacttg attagggtga tggttcacgt agtgggccat   7680
cgccctgata gacggttttt cgccctttga cgttggagtc cacgttcttt aatagtggac   7740
tcttgttcca aactggaaca acactcaacc ctatctcggt ctattctttt gatttataag   7800
ggattttgcc gatttcggcc tattggttaa aaaatgagct gatttaacaa aaatttaacg   7860
cgaattttaa caaaatatta acgcttacaa tttaggtggc acttttcggg gaaatgtgcg   7920
cggaacccct atttgtttat ttttctaaat acattcaaat atgtatccgc tcatgagaca   7980
ataaccctga taaatgcttc aataatattg aaaaaggaag agtatgagta ttcaacattt   8040
ccgtgtcgcc cttattccct tttttgcggc attttgcctt cctgtttttg ctcacccaga   8100
aacgctggtg aaagtaaaag atgctgaaga tcagttgggt gcacgagtgg gttacatcga   8160
actggatctc aacagcggta agatccttga gagttttcgc cccgaagaac gttttccaat   8220
gatgagcact tttaaagttc tgctatgtgg cgcggtatta tcccgtattg acgccgggca   8280
agagcaactc ggtcgccgca tacactattc tcagaatgac ttggttgagt actcaccagt   8340
cacagaaaag catcttacgg atggcatgac agtaagagaa ttatgcagtg ctgccataac   8400
catgagtgat aacactgcgg ccaacttact tctgacaacg atcggaggac cgaaggagct   8460
aaccgctttt ttgcacaaca tgggggatca tgtaactcgc cttgatcgtt gggaaccgga   8520
gctgaatgaa gccataccaa acgacgagcg tgacaccacg atgcctgtag caatggcaac   8580
aacgttgcgc aaactattaa ctggcgaact acttactcta gcttcccggc aacaattaat   8640
agactggatg gaggcggata aagttgcagg accacttctg cgctcggccc ttccggctgg   8700
```

ctggtttatt gctgataaat ctggagccgg tgagcgtggg tctcgcggta tcattgcagc 8760
actggggcca gatggtaagc cctcccgtat cgtagttatc tacacgacgg ggagtcaggc 8820
aactatggat gaacgaaata gacagatcgc tgagataggt gcctcactga ttaagcattg 8880
gtaactgtca gaccaagttt actcatatat actttagatt gatttaaaac ttcattttta 8940
atttaaaagg atctaggtga agatcctttt tgataatctc atgaccaaaa tcccttaacg 9000
tgagttttcg ttccactgag cgtcagaccc cgtagaaaag atcaaaggat cttcttgaga 9060
tccttttttt ctgcgcgtaa tctgctgctt gcaaacaaaa aaaccaccgc taccagcggt 9120
ggtttgtttg ccggatcaag agctaccaac tctttttccg aaggtaactg gcttcagcag 9180
agcgcagata ccaaatactg ttcttctagt gtagccgtag ttaggccacc acttcaagaa 9240
ctctgtagca ccgcctacat acctcgctct gctaatcctg ttaccagtgg ctgctgccag 9300
tggcgataag tcgtgtctta ccgggttgga ctcaagacga tagttaccgg ataaggcgca 9360
gcggtcgggc tgaacggggg gttcgtgcac acagcccagc ttggagcgaa cgacctacac 9420
cgaactgaga tacctacagc gtgagctatg agaaagcgcc acgcttcccg aagggagaaa 9480
ggcggacagg tatccggtaa gcggcagggt cggaacagga gagcgcacga gggagcttcc 9540
agggggaaac gcctggtatc tttatagtcc tgtcgggttt cgccacctct gacttgagcg 9600
tcgatttttg tgatgctcgt caggggggcg gagcctatgg aaaaacgcca gcaacgcggc 9660
ctttttacgg ttcctggcct tttgctggcc ttttgctcac atgttctttc ctgcgttatc 9720
ccctgattct gtggataacc gtattaccgc ctttgagtga gctgataccg ctcgccgcag 9780
ccgaacgacc gagcgcagcg agtcagtgag cgaggaagcg gaagagcgcc caatacgcaa 9840
accgcctctc cccgcgcgtt ggccgattca ttaatgcagc tggcacgaca ggtttcccga 9900
ctggaaagcg ggcagtgagc gcaacgcaat taatgtgagt tagctcactc attaggcacc 9960
ccaggcttta cactttatgc ttccggctcg tatgttgtgt ggaattgtga gcggataaca 10020
atttcacaca ggaaacagct atgaccatga ttacgccaag cgcgcaatta accctcacta 10080
aagggaacaa aagctggagc tgcaagcttg g 10111

<210> SEQ ID NO 44
<211> LENGTH: 286
<212> TYPE: PRT
<213> ORGANISM: Artificial Sequence
<220> FEATURE:
<223> OTHER INFORMATION: beta lactamase from pCCL.MND.coRAG1 plasmid

<400> SEQUENCE: 44

Met Ser Ile Gln His Phe Arg Val Ala Leu Ile Pro Phe Phe Ala Ala
1 5 10 15

Phe Cys Leu Pro Val Phe Ala His Pro Glu Thr Leu Val Lys Val Lys
20 25 30

Asp Ala Glu Asp Gln Leu Gly Ala Arg Val Gly Tyr Ile Glu Leu Asp
35 40 45

Leu Asn Ser Gly Lys Ile Leu Glu Ser Phe Arg Pro Glu Glu Arg Phe
50 55 60

Pro Met Met Ser Thr Phe Lys Val Leu Leu Cys Gly Ala Val Leu Ser
65 70 75 80

Arg Ile Asp Ala Gly Gln Glu Gln Leu Gly Arg Arg Ile His Tyr Ser
85 90 95

Gln Asn Asp Leu Val Glu Tyr Ser Pro Val Thr Glu Lys His Leu Thr
100 105 110

-continued

```
Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```